(12) United States Patent
Matousek et al.

(10) Patent No.: US 10,669,250 B2
(45) Date of Patent: *Jun. 2, 2020

(54) HYPERVALENT IODINE $CF_2CF_2X$ REAGENTS AND THEIR USE

(71) Applicants: ETH Zurich, Zurich (CH); INSTITUTE OF ORGANIC CHEMISTRY AND BIOCHEMISTRY ACADEMY OF SCIENCES OF THE CZECH REPUBLIC, Prague (CZ)

(72) Inventors: Vaclav Matousek, Zliv (CZ); Petr Beier, Podebrad (CZ); Antonio Togni, Zurich (CH)

(73) Assignees: ETH ZURICH, Zurich (CH); INSTITUTE OF ORGANIC CHEMISTRY AND BIOCHEMISTRY ACADEMY OF SCIENCES OF THE CZECH REPUBLIC

( * ) Notice: Subject to any disclaimer, the term of this patent is extended or adjusted under 35 U.S.C. 154(b) by 0 days.

This patent is subject to a terminal disclaimer.

(21) Appl. No.: 16/055,629

(22) Filed: Aug. 6, 2018

(65) Prior Publication Data
US 2019/0040036 A1 Feb. 7, 2019

Related U.S. Application Data

(63) Continuation-in-part of application No. 15/501,872, filed as application No. PCT/CH2015/000113 on Aug. 3, 2015, now Pat. No. 10,040,812.

(30) Foreign Application Priority Data

Aug. 7, 2014 (EP) ..................................... 14180136

(51) Int. Cl.
*C07D 347/00* (2006.01)
*C07D 421/06* (2006.01)
(52) U.S. Cl.
CPC ......... *C07D 347/00* (2013.01); *C07D 421/06* (2013.01)
(58) Field of Classification Search
CPC .................................................. C07D 347/00
See application file for complete search history.

(56) References Cited

PUBLICATIONS

Mizuta S. et al: "Trifluoromethylation of allylsilanes under photoredox catalysis", Organic Letters, vol. 15, No. 5, Mar. 6, 2013 (Mar. 6, 2013), pp. 1250-1253.
Zhang B. et al:"6-Trifluoromethyl-phenanthridines through radical trifluoromethylation of isonitriles", Angewandte Chemie International Edition, vol. 52, No. 41, Oct. 4, 2013 (Oct. 4, 2013), pp. 10792-10795.
Li Y. et al: "Transition-metal-free trifluoromethylaminoxylation of alkenes", Angewandte Chemie International Edition, vol. 51, No. 33, Aug. 13, 2012 (Aug. 13, 2012),pp. 8221-8224.
Carboni A. et al: "Photoredox-induced three-component oxy-, amino-, and carbotrifluoromethylation of enecarbamates", Organic Letters, vol. 16, No. 4, Feb. 12, 2014(Feb. 12, 2014), pp. 1240-1243.
He et al. Angewandte Chemie, International Edition (2012), 51(16), 3944-3947.

*Primary Examiner* — Bruck Kifle
(74) *Attorney, Agent, or Firm* — JMB Davis Ben-David

(57) ABSTRACT

Described herein are hypervalent iodine reagents.

18 Claims, 2 Drawing Sheets

Fig. 2

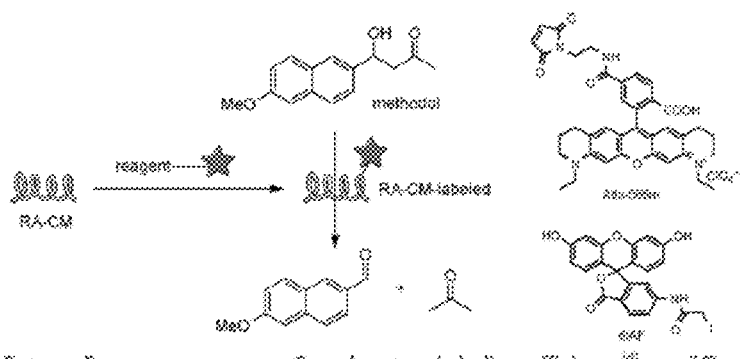

| Entry | Enzyme | Co-solvent | Labeling efficiency[d] [%] | $v_0/[E]_0$ [min$^{-1}$] |
|---|---|---|---|---|
| 1 | RA-CM | -- | -- | 5.15 |
| 2 | RA-CM-Atto-565m | -- | 146 | 0 |
| 3 | RA-CM-6IAF | 10% MeCN | 92 | 1.08 |
| 4 | RA-CM-8k | 30% DMSO | 67 | 1.89 |
| 5[c] | RA-CM-9c | 30% DMSO | 61 | 4.25 |
| 6 | RA-CM-10a | 10% MeCN | 40 | 2.20 |

[a] Conditions for the labeling: c(RA-CM) = 25 μM, c(reagent) = 250 μM, degassed buffer (25 mM HEPES, 100 mM NaCl, pH 7.5), 18 h at rt, quenched with 10 mM 2-mercaptoethanol. [b] The reactions were carried out at 29 °C in degassed buffer (25 mM HEPES, 100 mM NaCl, pH 7.5) containing acetonitrile (2.7%). [c] Reaction time for labeling was reduced to 4 h. [d] Labeling efficiency signifies the average number of chromophores attached to one protein.

HYPERVALENT IODINE $CF_2CF_2X$ REAGENTS AND THEIR USE

CROSS-REFERENCE TO RELATED APPLICATIONS

This is a Continuation-in-Part of U.S. patent application Ser. No. 15/501,872 filed on Feb. 6, 2017, which is the US National Stage of International Application No. PCT/CH2015/000113 filed on Aug. 3, 2015, which was published in English under PCT Article 21(2), and which in turn claims the priority of European patent application no. 14 180 136.5, filed Aug. 7, 2014, the disclosure of which is incorporated herein by reference in its entirety.

TECHNICAL FIELD

The present invention relates to hypervalent iodine reagents.

BACKGROUND

Fluoroalkylation reagents based on hypervalent iodine are widely used to transfer fluoroalkyl moieties to various nucleophiles such as S-, P-, O-, N-, and C-nucleophilic functionalities. Thiols, in particular, exhibit excellent reactivity and selectivity in such fluoroalkylation reactions, which has been demonstrated by selective S-trifluoromethylation of, for example, coenzyme A and Sandostatin. However, the transferred groups have so far been limited to simple structural motifs. The present invention provides reagents useful in the transfer of a tetrafluoralkyl moiety coupled to various functional groups such as affinity tags or fluorescent dyes.

The hypervalent cyclic $CF_3$-iodine reagents[1]

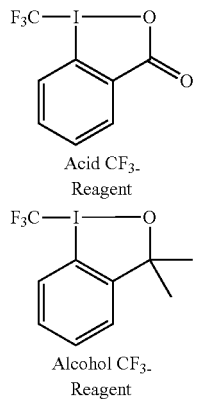

Acid $CF_3$-Reagent

Alcohol $CF_3$-Reagent known as Togni reagents (herein referred to as acid $CF_3$ reagent and alcohol $CF_3$ reagent) turned out to be extremely versatile donors of the formally electrophilic $CF_3$-synthon. The success story of the Togni reagents also inspired other research groups to develop other fluoroalkylated analogues of them and explore their potential in electrophilic fluoroalkylation.

In 2008, Hu et al. reported a synthesis of a related (phenylsulfonyl)difluoromethyl hypervalent iodine reagent, utilizing the Umpolung concept known from the Togni reagents. The (phenylsulfonyl)difluoromethyl trimethylsilane, which has shown competence in several examples of nucleophilic difluorosulfonylation and indirect difluoromethylation,[2] was subjected to Umpolung with acetoxyiodane to give (phenylsulfonyl)difluoromethyl hypervalent iodine reagent in good yield.[3]

In their original report, the stable alcohol $PhSO_2CF_2$-reagent could be employed in electrophilic (phenylsulfonyl)difluoromethylation of a variety of thiol substrates in up to 87% yield.

In 2012, Hu et al. demonstrated that the (phenylsulfonyl)difluoromethylation hypervalent iodine reagent can be used for electrophilic (phenylsulfonyl)difluoromethylation of α,β-unsaturated carboxylic acids in the presence of catalytic amounts of an in-situ formed copper complex. Under the applied reaction conditions, acrylate substrates underwent decarboxylation followed by phenylsulfonyldifluoromethylation.[4]

In a publication that followed very soon, the same research group could show that β,γ-unsaturated carboxylic acids undergo decarboxylation/phenysulfonyldifluoromethylation to give allylic phenylsulfonyldifluoromethylated products in good yields. The resulting products could be further transformed into useful difluoromethylated and difluoromethylenated products.[5]

Apart from the (phenylsulfonyl)difluoromethylation hypervalent iodine reagent, perfluoroethyl analogue of acid $CF_3$ reagent was synthetized by Studer et al. who showcased that the resulting reagent can be used similarly as acid CF3 reagent in tandem radical fluoroalkylation/aminoxylation.[6]

Perfluoroethylation is also mentioned in further documents. Mizuta et al. disclose trifluoromethylation of allylsilanes under photoredox catalysis with an indication that also some perfluoroethylation at the allylic position was successful.[13] Zhang et al. discuss mechanistic aspects of perfluoroalkylation. In particular trifluoromethylation.[14] Carboni et al. also deal with perfluoroalkylation, in particular trifluoromethylation, of enecarbamates with one example concerning perfluoroethylation.[15]

While the (phenylsulfonyl)difluoromethyl substituted reagent has been shown suitable for producing some trifluoromethylated and difluoromethylenated olefins, there is still a need for further fluoroalkylated products.

DISCLOSURE OF THE INVENTION

Hence, it is a general object of the invention to provide a reagent that is suitable for fluoroalkylating a broad variety of compounds and having broad applicability.

Now, in order to implement these and still further objects of the invention, which will become more readily apparent as the description proceeds, the fluoroalkylation reagent of the present invention is a hypervalent iodine of formula (I) and/or formula (II)

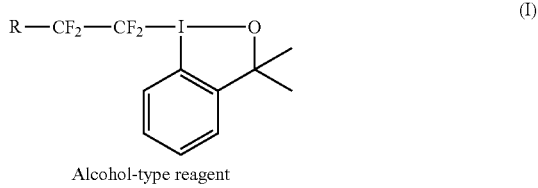

Alcohol-type reagent

Acid-type reagent wherein R is a nucleophile other than fluorine or perfluoroalkyl.

Compounds of formula (I) or formula (II) with a specific R will later on be termed (specific R)-I or (specific R)-II, i.e. for e.g. R=PhS the compounds will be termed PhS-I and PhS-II.

Compounds with the basic structure

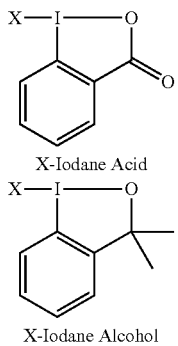

X-Iodane Acid

X-Iodane Alcohol wherein X may be any group are also termed iodanes or more specific X-iodane acid and X-iodane alcohol.

In the compounds of formula (I) or formula (II) preferred nucleophiles are selected from the group consisting of unsubstituted or substituted imidazoles, unsubstituted or substituted pyrazoles, unsubstituted or substituted benzimidazoles, unsubstituted or substituted thiophenols, unsubstituted or substituted phenols, like 4-methoxyphenols, ethyl-4-hydroxybenzoates, 4-bromophenols, unsubstituted or substituted pyridine-thiols, unsubstituted or substituted 2-mercaptobenzothiazoles, potassium cyanide and diethylphosphite, more preferred imidazole, pyrazole, benzimidazole, thiophenol, 4-methoxyphenol, ethyl-4-hydroxybenzoate, 4-bromophenols, pyridine-2-thiol, 2-mercaptobenzothiazoles, potassium cyanide and diethylphosphite, even more preferred imidazole, pyrazole, benzimidazole, thiophenol, 4-methoxyphenol, ethyl-4-hydroxybenzoate, 4-bromophenols and pyridine-2-thiol.

Suitable substituents can independently from each other be small groups like halogens, linear or branched, unsubstituted or halogen substituted C1 to C4 alkyl or C1 to C4 alkenyl or C1 to C4 alkinyl or C1 to C4 alkoxy or C1 to C4 alkyl carboxylate groups. In specific cases a substituent can also be a linker or spacer coupled to a desired group such as a functional group, said linker preferably being an optionally halogen substituted aliphatic group.

In general the R listed above will be unsubstituted (i.e. the —R will not be further substituted than explicitly indicated above).

A preferred synthesis involves an intermediate compound of type R—$CF_2$—$CF_2$—$SiPh_x(C_1\text{-}C_3\text{-alkyl})_{3-x}$ wherein Ph is phenyl and x is 0 to 3, preferred R—$CF_2$—$CF_2$—$SiMe_3$. This intermediate can be produced via different routes. One of these routes uses 1,2,-dibromo-1,1,2,2-tetrafluoroethane (also termed Halon 2402) that can be readily prepared but that for its ozone depleting potential is not easily commercially available in high amounts.

Starting from R—H and Br—$CF_2$—$CF_2$—Br, in a first step R—$CF_2$—$CF_2$—Br is formed, possibly via a mechanism as follows:

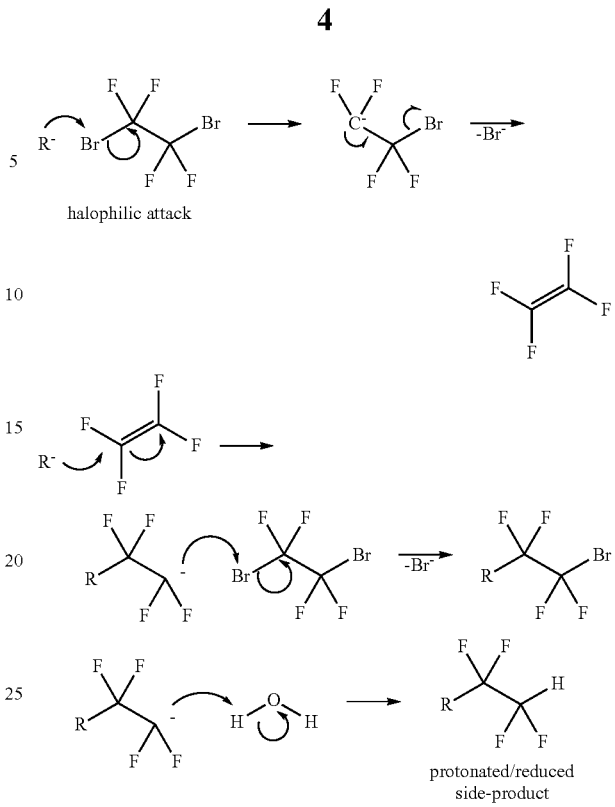

halophilic attack protonated/reduced side-product

In a second step, R—$CF_2$—$CF_2$—Br is reacted to R—$CF_2$—$CF_2$—$SiPh_x(C_1\text{-}C_3\text{-alkyl})_{3-x}$ using Hal-$SiPh_x(C_1\text{-}C_3\text{-alkyl})_{3-x}$ as reagent wherein the halogen (Hal) suitably is Cl.

In an alternative method avoiding Br—$CF_2$—$CF_2$—Br a nucleophile R—H is reacted with tetrafluoroethylene ($CF_2$=$CF_2$) in the presence of a catalyst, e.g. NaH/n-Bu4NI, to yield X—$CF_2$—$CF_2$—H that—in a second step—is reacted to X—$CF_2$—$CF_2$—$SiPhx(C_1\text{-}C_3\text{-alkyl})_{3-x}$ using Hal-$SiPh_x(C_1\text{-}C_3\text{-alkyl})_{3-x}$ as reagent in the presence of a base.

X—$CF_2$—$CF_2$—$SiPhx(C_1\text{-}C_3\text{-alkyl})_{3-x}$ or its use in the preparation of hypervalent iodine-fluoroalkyl reagents and in the preparation of fluoroalkyl and fluoroalkylene compounds is also an object of the present invention.

In a final step, R—$CF_2$—$CF_2$—$SiPhx(C_1\text{-}C_3\text{-alkyl})_{3-x}$ is reacted with an "iodane" alcohol or acid such as

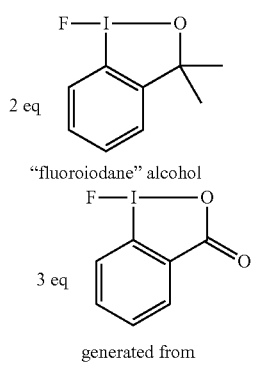

2 eq

"fluoroiodane" alcohol 3 eq generated from

In-situ generated "fluoroiodane" acid

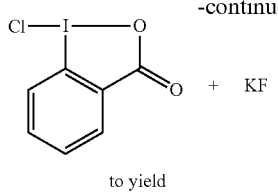

+ KF to yield

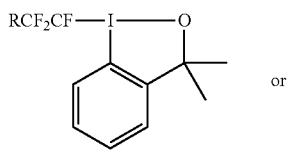

(I)

or

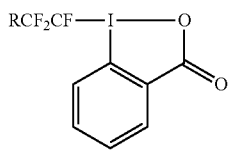

(II)

For the same or similar R groups, the compounds of formula (I) usually distinguish from the reagents of formula (II) in that those of formula (I) have better solubility and higher basicity while those of formula (II) are the better oxidants.

Since R must be a nucleophile, it may be necessary to provide a desired group with a nucleophilic substituent such as —SH or —OH, possibly via a linker in order to retain the original features of the desired group. In this case R in compounds of formula (I) or formula (II) is "desired group—linker—nucleophilic substituent". In e.g. biological applications such desired groups can e.g. be fluorescent groups or biotin.

Some examples of compounds of formula (I) and/or formula (II) are azole-tetrafluoroethyl-based reagents, phenoxytetrafluoroethyl and thiophenoxytetrafluoroethyl-substituted reagents. These represent the families that can be most easily tuned and functionalized. Halogen or heteoatom substitution on the aromatic nuclei of fluoroalkylated moieties can provide additional vectors for further functionalization in carbon-carbon and carbon-heteroatom bond-forming reactions.

Some of such compounds are illustrated below:

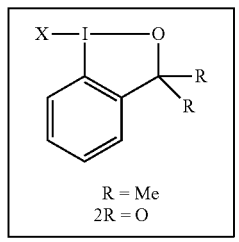

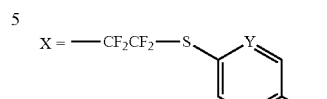

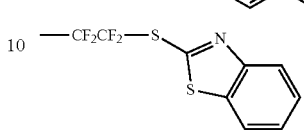

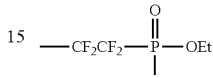

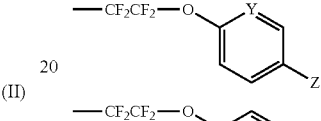

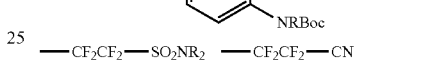

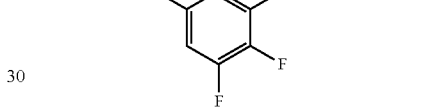

Y = CH, N
Z = H, Br

Compounds of formula (I) and/or formula (II) can be used for producing a broad variety of R—$CF_2$—$CF_2$-substituted compounds like compounds of all classes that have already been trifluoromethylated, e.g. by reacting compounds of formula (I) and/or compounds of formula (II) with reactive groups such as reactive groups of the following types:

sulfur centered nucleophiles, like —SH, carbon-centered nucleophiles, like silyl enolethers, silyl ketene imines and active methylene compounds, such as 1,3-dicarbonyl compounds, oxygen-centered nucleophiles, like —OH, hydroxylamines such as N-monosubstituted or preferably N,N-disubstituted hydroxylamines and sulfonic acids, nitrogen-centered nucleophiles, like cyclic aromatic heterocycles with at least 2 nitrogens, such as imidazoles, pyrazoles and triazole derivatives, phosphorous centered nucleophiles, like primary phosphines and secondary phosphines.

One preferred group to be reacted with the compounds of formula (I) or formula (II) are cysteins in any biological environment.

For example a cysteine group can be labelled with a fluorescent group in a very selective and close to quantitative manner according to the reaction scheme

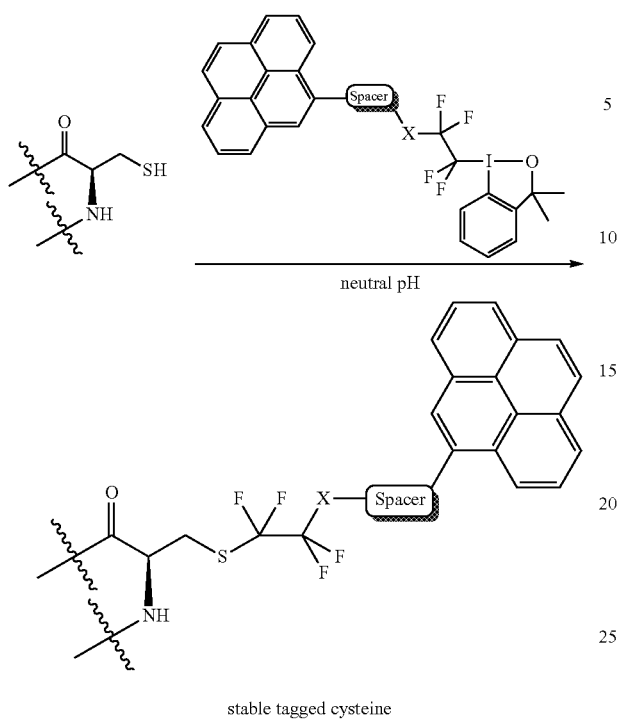

neutral pH stable tagged cysteine

Such stable adduct can be used for the determination of reduced glutathione (GSH). In combination with HPLC fluorimetry GSH can be determined in blood plasma. The method allows the detection of free cysteine, homocystein, coenzyme A etc. in one single analysis.

In another application R comprises a biotinyl group

The introduction of the biotin moiety into cysteine comprising peptides and in cysteine rich domains allows use of Pull-Down Assays due to the high affinity of biotin to streptavidin.

MODES FOR CARRYING OUT THE INVENTION

One method for producing compounds of formula (I) and compounds of formula (II) is via the following synthetic approach (below R=Nu):

1. Bromotetrafluoroethylation

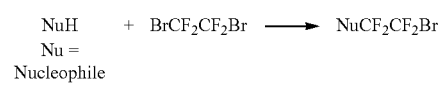

NuH + BrCF$_2$CF$_2$Br ⟶ NuCF$_2$CF$_2$Br
Nu = Nucleophile

2. Reduction/Trimethylsilylation

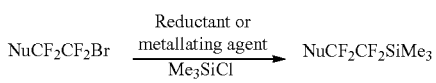

NuCF$_2$CF$_2$Br $\xrightarrow[\text{Me}_3\text{SiCl}]{\text{Reductant or metallating agent}}$ NuCF$_2$CF$_2$SiMe$_3$

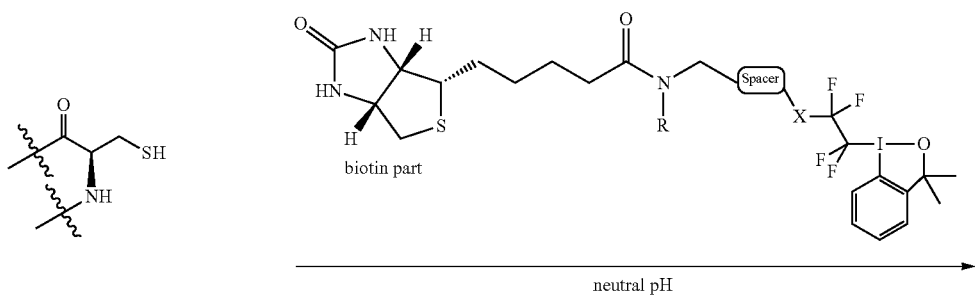

neutral pH

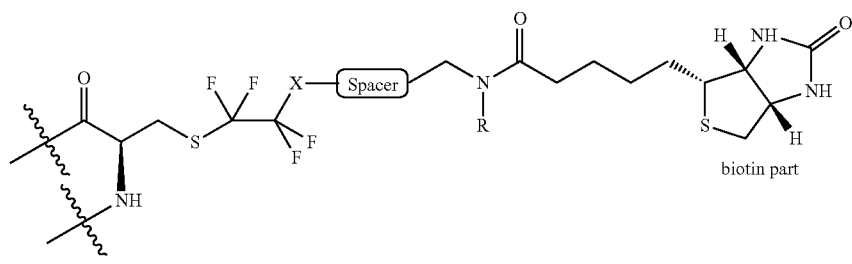

stable tagged cysteine

3. Umpolung a) alcohol reagent:

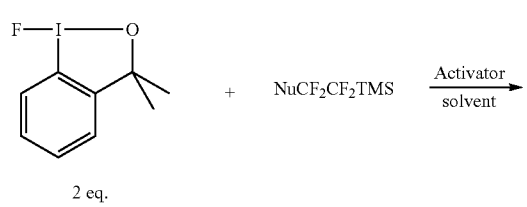

2 eq.

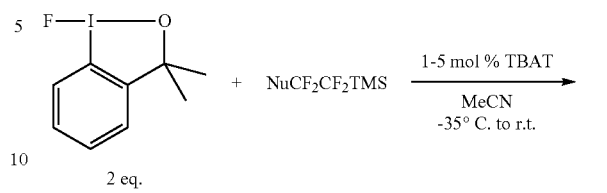

2 eq.

b) acid reagent:

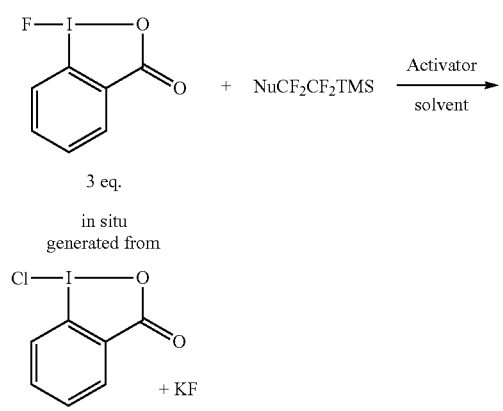

3 eq.

in situ generated from

+ KF

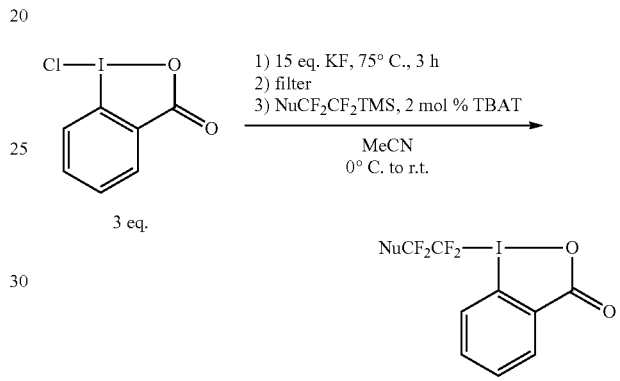

3 eq.

In preferred embodiments, the following more detailed reaction conditions are used:

1. Bromotetrafluoroethylation

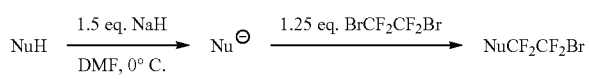

2. Reduction/Trimethylsilylation

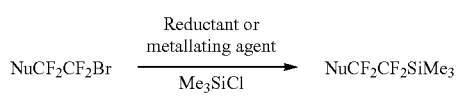

TBAT=tetrabutylammonium triphenyldifluorosilicate
r.t.=20° C. to 25° C.

Suitable reducing or metallating agents/methods are e.g. metallic magnesium, metallic aluminum, metallic zinc, tris-dialkylaminophosphines, tetrakis-dialkylaminoethylenes,i-propylmagnesium chloride-lithium chloride complex, Grignard reagents, alkyl, alkenyl and aryl lithiums, and cathodic electroreduction.

Other activators that can be used are generally ate complexes of fluoride anion and an inorganic or organic Lewis acidic organic acceptor, sources of naked anhydrous fluoride anion, such as tetraalkylammonium fluorides, tetraalkylphosphonium or tetraarylphosphonium fluorides, cesium fluoride, combination of alkali metal fluorides and alkali metal chelators such as crown ethers or related structures.

Solvents other than acetonitrile are THF, higher nitrile analogues of acetonitrile, halogenated aliphatic and aromatic solvents, tertiary carboxamides.

The Umpolung of the alcohol compound of formula (I) can be performed at temperatures up to 25° C. In general, however, it is performed at temperatures of at most 0° C. Often improved purity is obtained at temperatures significantly below 0° C. such as below −10° C. or even below −20° C. such as −35° C. Due to its lower reactivity, the Umpolung of the acid compound usually is performed at higher temperature, usually at temperatures from about 0° C. up to ambient temperature (rt), usually 20° C. to 25° C.

Experimental Part:

In the following experimental part trimethylsilanes are used as $Phx(C_1-C_3-alkyl)_{3-x}$ silanes. Trimethylsilanes are preferred silanes because they are comparably cheap and readily available.

I. Synthesis of R—CF$_2$CF$_2$—X Reagents

I.1. Optimization of the Synthesis of Compound of Formula (I) with R=—SPh

Using PhSCF$_2$CF$_2$SiMe$_3$, an optimum protocol for smooth and high yielding Umpolung reaction was elaborated.

The comparison of the result of Umpolung of Ruppert-Prakash reagent with chloroiodane acid and fluoroiodane alcohol indicated that chloroiodane acid is not sufficiently reactive and that even in situ formation of fluoroiodane acid as mere intermediate results in poorer yields than starting from isolated fluoroiodane alcohol.

The best result was obtained with the combined use of excess fluoroiodane alcohol and a well soluble fluoride source (e.g. tetrabutylammonium triphenyldifluorosilicate (TBAT)(see Table 1) as activator.

TABLE 1

Results of the Umpolung of PhSCF$_2$CF$_2$SiMe$_3$ with fluoroiodane alcohol

| entry | activator | equiv. of PhSCF2CF2SiMe3 | equiv. fluoro-iodane alcohol | solvent | t [° C.] reaction time | yield$^e$ | scale |
|---|---|---|---|---|---|---|---|
| 1 | excess of spray dried KF | 1.2 | 1 eq. = 0.25M | MeCN | 0° C. to 25° C. 6 h | 22% (18%) | 100 mg |
| 2$^a$ | 10 mol % TBAT | 1 | 2 eq. = 0.25M | THF | −10° C. to 25° C. 3 h | (40%) | 100 mg |
| 3b | 10 mol % TBAT | 1 | 2 eq. = 0.33M | THF | 0° C. | 26% | 100 mg |
| 3$^c$ | 1 mol % TBAT | 1 | 2 eq. = 0.4M | MeCN | −20° C. to 0° C. 2 h | 69% (68%) | 100 mg |
| 4$^d$ | 1 mol % TBAT | 1 | 2 eq. = 0.4M | MeCN | −35° C. to 0° C. 1 h | 93% (85%) | 1 g |

$^a$PhSCF$_2$CF$_2$SiMe$_3$ was added in three portions during 1 h.
bPhSCF$_2$CF$_2$SiMe$_3$ was added with syringe pump within 8 h.
$^c$PhSCF$_2$CF$_2$SiMe$_3$ was added at once at −20° C.
$^d$PhSCF$_2$CF$_2$SiMe$_3$ was added within 10 minutes
$^e$the yields not in parenthesis are NMR yields measured with internal standard PhCF$_3$, those in parenthesis are isolated yields.
TBAT = tetrabutylammonium triphenyldifluorosilicate The worst result was obtained with KF. The Umpolung was slow and incomplete (entry 1). Switching to the use of isolated fluoroiodane alcohol in THF in combination with 10 mol % TBAT improved the yield to 40% (entry 2). During the conditions of entry 2, an instanteous color change to orange was observed after the addition of the first portion of PhSCF$_2$CF$_2$SiMe$_3$ to the mixture of fluoroiodane alcohol and TBAT. This rapid color change might possibly be interpreted as an accompanying decomposition of PhSCF$_2$CF$_2$SiMe$_3$ in the presence of highly reactive fluoride activator. Therefore, in a next approach the reaction temperature was lowered to −20° C. and less activator was used (entry 3). This appeared to be a fruitful intervention leading to 69% NMR yield of PhS-I. Pleasingly, performing the reaction on a 1 g scale, lowering the reaction temperature to −35° C. and adding PhSCF$_2$CF$_2$SiMe$_3$ within 10 minutes gave 93% NMR yield of PhS-I. A quick TLC analysis of the reaction mixture revealed that the reaction was essentially complete in 5 minutes after the silane PhSCF$_2$CF$_2$SiMe$_3$ had been added.

These observations support the following hypothesis that, however, shall not be construed as limiting the invention in any way:

(i) highly soluble fluoride source is the best activator (ii) fluoroiodane alcohol is the best acceptor of the fluoroalkylated carbanion (iii) catalysis is mediated only by the fast dissolving fluoride such as TBAT throughout the whole catalytic Umpolung process ("pure fluoride catalysis") (This is astonishing since in a number of fluoride-catalyzed nucleophilic fluoroalkylations, for example additions of fluoroalkylated silanes to benzaldehydes, the catalytically relevant activator responsible for major part of the conversion is the intermediate alkoxide and not the fluoride.)

(iv) instability of activated fluoroalkylated silanes can be minimized by using excess of the acceptor fluoroiodane alcohol.

Optimized synthesis of PhS-I

I.2. Optimization of the Synthesis of PhS-II

Having optimized the synthesis of PhS-I, also the synthesis of the related "acid" reagent PhS-II was further investigated.

First the potential of acetoxyiodane acid as the precursor for synthesis of PhS-II was explored. However, the acetate of the acetoxyiodane acid proved to have insufficient activating power.

Thus, the poorly stable fluoroiodane acid was chosen. The fluoroiodane acid in pure form an only be obtained in solution, preferably as a solution in MeCN. Treatment of 2 equivalents of 1-chloro-benziodoxol-3-one (chloroiodane acid) with 10 equivalents of spray-dried KF in MeCN at 75° C. provided a suspension of KCl, KF and dissolved fluoroiodane acid. The solution of fluoroiodane acid was carefully canula-filtered under Ar from one into another Schlenk flash and treated with 10 mol % TBAT and 1 equivalent of $PhSCF_2CF_2SiMe_3$ at 5° C. Formation of PhS-II in 59% NMR yield together with 28% protodesilylation product of $PhSCF_2CF_2SiMe_3$ was observed.

In the next experiment, 3 equivalents of in-situ formed fluoroiodane acid together with 1 mol % TBAT was used. First the Umpolung of $PhSCF_2CF_2SiMe_3$ was performed at 0° C., but even after 1 h, only low conversion of the silane $PhSCF_2CF_2SiMe_3$ was detected. After warming up to 20° C. to 25° C., much faster progress of the reaction was observed; within 3 h, the starting material could no longer be detected on TLC anymore. $^{19}F$ NMR examination of the crude reaction mixture revealed formation of PhS-II in 60% NMR yield together with 17% $PhSCF_2CF_2H$. PhS-II could be then isolated by flash chromatography in 60% yield, with chromatographic behaviour similar to the related acid $CF_3$ reagent.

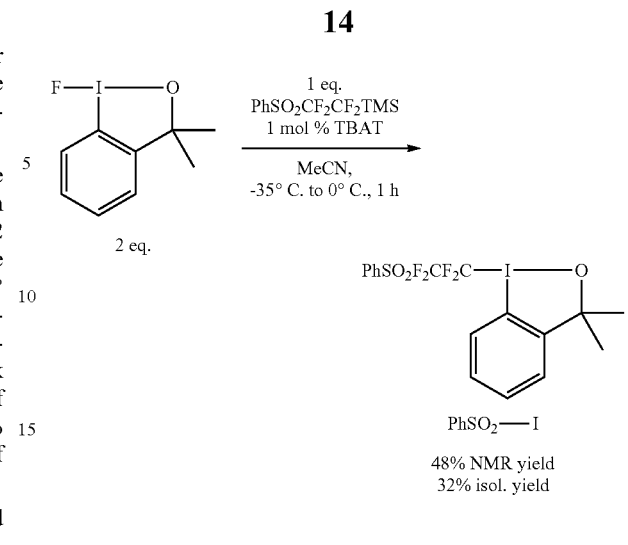

Preparation of $PhSO_2CF_2CF_2$—Acid-Reagent $PhSO_2$—II

When $PhSO_2CF_2CF_2SiMe_3$ was subjected to 3 equivalents of in-situ formed fluoroiodane acid in the presence of 1 mol % TBAT, formation of the desired reagent $PhSO_2$—II could be detected only in 8% NMR yield after 3 h at ambient temperature (20° C. to 25° C.). The lower nucleophilicity of the silane in combination with lower purity of $PhSO_2CF_2CF_2SiMe_3$ used is assumed to the reason of failure. The silane used in these experiments, namely, was contaminated with 15%

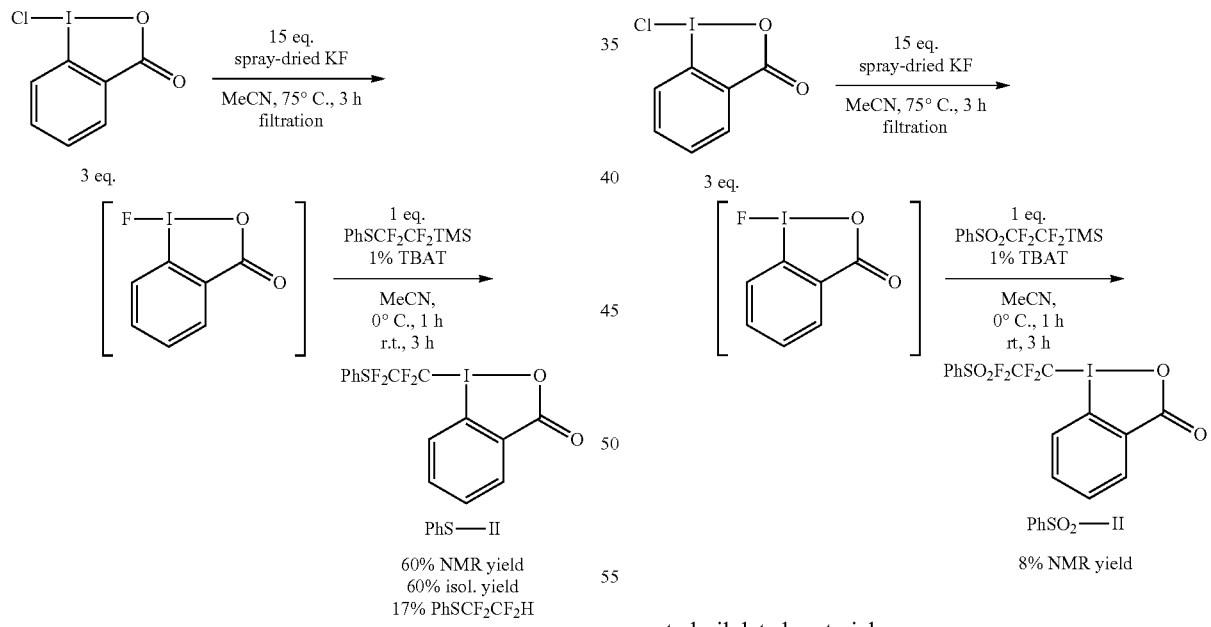

Preparation of $PhSO_2CF_2CF_2$—Alcohol-Reagent $PhSO_2$—I

The reaction of $PhSO_2CF_2CF_2TMS$ with 2 equivalents of fluoroiodane alcohol in the presence of 1 mol % TBAT at −35° C. in MeCN gave 48% NMR yield of $PhSO_2$—I. Pure $PhSO_2$—I could be obtained in 32% isolated yield.

protodesilylated material.

Synthesis of $PhSO_2$—II

I.4 Synthesis of 1-[(1,1,2,2-Tetrafluoro-2-bromo]-1H-imidazole and respective trimethylsilane Nitrogen-based heterocyclic functionalities are of high importance in medicinal chemistry and agrochemistry. Therefore compounds of formula (I) and formula (II) with R comprising nitrogen-containing heterocyclic groups are of high interest in these fields.

Im-I and Im-II were used as representatives of this class.

The synthesis of the desired reagents required access to the corresponding 1-[(1,1,2,2-Tetrafluoro-2-trimethylsilyl)ethyl]-1H-imidazole. Following the synthesis reported by Petko et al.[7 ENREF 13], imidazole was deprotonated with 1.05 equivalents of sodium hydride in DMF and treated with 2 equivalents BrCF$_2$CF$_2$Br (see also [8 ENREF 14]) in the presence of 2 mol % TBAT to give 1-[(1,1,2,2-Tetrafluoro-2-bromo]-1H-imidazole in 42% yield (Lit. 68% yield). In a second experiment, in order to need less dibromotetrafluoroethane, its excess was reduced to 1.5 equivalents and simultaneously the reactivity of the imidazolide anion was increased by increasing the amount of phase transfer catalyst (activator) to 7 mol %. Combination of these two adjustments provided 1-[(1,1,2,2-Tetrafluoro-2-bromo]-1H-imidazole in 68% yield which represents a certain improvement in comparison to the synthesis reported in the literature.

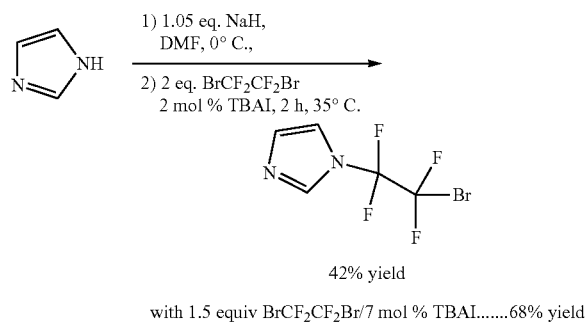

Synthesis of 1-[(1,1,2,2-Tetrafluoro-2-bromo]-1H-imidazole by Reaction of Imidazolyl Sodium with BrCF$_2$CF$_2$Br Under PTC Catalysis Although the bromotetrafluoroethylation of imidazole formally represents a nucleophilic substitution, it actually comprises a combination of several elementary steps. The generally accepted mechanism is depicted in the Scheme below. The overall process is initiated by bromophilic attack of the nucleophile on BrCF$_2$CF$_2$Br, providing the brominated nucleophile and the highly unstable bromotetrafluoroethyl anion Int1 which quickly loses bromide anion to give the intermediate tetrafluoroethylene (Int2). Tetrafluoroethylene then behaves as the actual acceptor of the nucleophile, forming fluoroalkylated carbanion Int3. This carbanion is then finally brominated by a further bromophilic attack of BrCF$_2$CF$_2$Br, initiating a new reaction cycle with the release of new Int1.

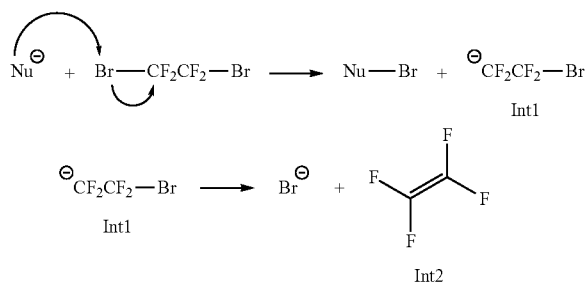

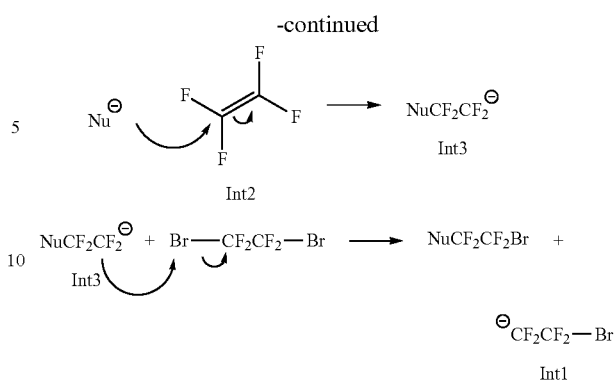

Mechanism of Bromotetrafluoroalkylation of Nucleophiles with BrCF$_2$CF$_2$Br

The next step in the synthesis of 1-[(1,1,2,2-Tetrafluoro-2-trimethylsilyl)ethyl]-1H-imidazole was a debrominative reductive silylation under Barbier conditions. 1-[(1,1,2,2-Tetrafluoro-2-bromo]-1H-imidazole was treated with 1.5 equivalents Mg grit and 4 equivalents of TMSCl in THF to provide the corresponding 1-[(1,1,2,2-Tetrafluoro-2-trimethylsilyl)ethyl]-1H-imidazole in 71% yield after Kugelrohr distillation. During the aqueous workup of the silane, care had to be taken to work under neutral conditions and in the cold, otherwise extensive protodesilylation of 1-[(1,1,2,2-Tetrafluoro-2-trimethylsilyl)ethyl]-1H-imidazole was observed.

Reductive silylation of 1-[(1,1,2,2-Tetrafluoro-2-bromo]-1H-imidazole under Barbier conditions I.5 Synthesis of Imidazole-I (Im-I)

1 equivalent of 1-[(1,1,2,2-Tetrafluoro-2-trimethylsilyl)ethyl]-1H-imidazole was treated with 2 equivalents of fluoroiodane alcohol in the presence of 1 mol % TBAT in acetonitrile at a temperature of −35° C. to 0° C. for 1 hour providing Im-I in 77-80% isolated yield. Similarly as in the case of synthesis of PhS-I, the Umpolung of 1-[(1,1,2,2-Tetrafluoro-2-trimethylsilyl)ethyl]-1H-imidazole with fluoroiodane alcohol was essentially finished within 10 minutes after addition of silane was complete (as evidenced by TLC analysis). Reagent Im-I was obtained as a viscous yellowish liquid that soon crystallized at ambient temperature (20° C. to 25° C.).

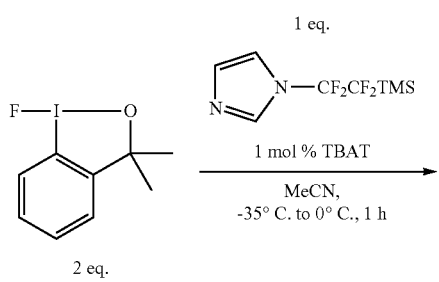

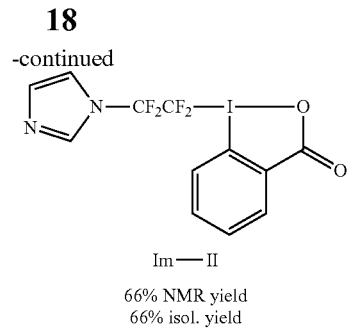

66% NMR yield
66% isol. yield

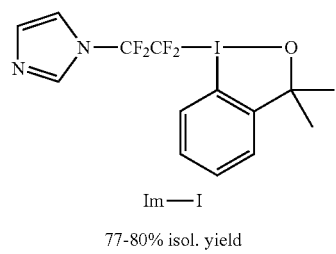

77-80% isol. yield

Synthesis of "Alcohol-$CF_2CF_2$-Im Reagent" imidazole-I (Im-I)

I.6 Synthesis of Imidazole-II (Im-II)

The synthesis of the related "acid-type" reagent Im-II was conducted along the lines of the previously optimized protocol. Reaction of 1 equivalent of 1-[(1,1,2,2-Tetrafluoro-2-trimethylsilyl)ethyl]-1H-imidazole with 3 equivalents of an in-situ formed fluoroiodane acid in the presence of 1 mol % TBAT gave Im-II in 66% NMR yield. The compound could be isolated by flash chromatography in 66% isolated yield.

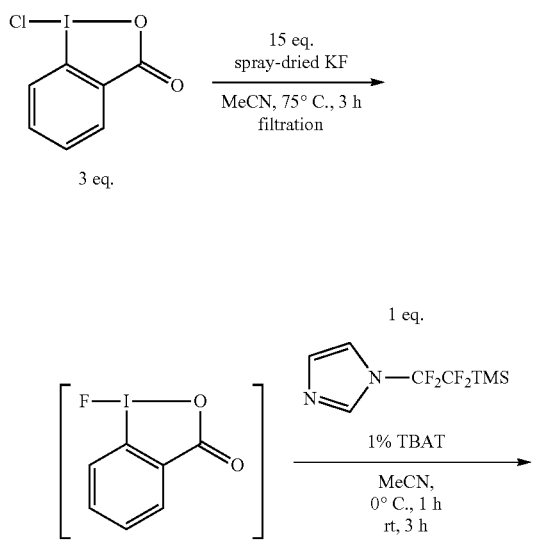

Synthesis of "Acid-$CF_2CF_2$—Im Reagent" Imidazole-II

According to the methods described above so far the compounds of formula (I) and formula (II) have been prepared in the indicated isolated yields.

In detail: The numbers written under the reagents denote the isolated yields of successive steps in their syntheses (1. synthesis of $XCF_2CF_2Br$, 2. conversion of $XCF_2CF_2Br$ to $XCF_2CF_2TMS$ and 3. the final "Umpolung" step leading to the hypervalent iodine-$CF_2CF_2X$ reagent.

II. Solvent Dependence of $^{19}F$ NMR Spectra of $CF_2CF_2$—X Reagents

When measuring the $^{19}F$ NMR spectra of PhS-I in $CDCl_3$ on the one hand and in acetonitrile on the other hand an interesting phenomenon was observed. The crude reaction mixture showed in MeCN a well resolved pair of triplets at −83.1 ppm and −92.4 ppm. However, the isolated PhS-I re-dissolved in $CDCl_3$, gave one triplet at −82.2 ppm and a broad resonance at −89.9 ppm instead.

The same compound in d3-MeCN at ambient temperature (20° C. to 25° C.), gave again a clearly developed pair of triplets at −83.1 ppm and −92.4 ppm.

A similar solvent-dependent behaviour, only less pronounced, was observed for other reagents as well.

A not limiting interpretation of this behaviour might be as follows:

Reagent PhS-I is assumed to be in dynamic equilibrium between its cyclic and open iodonium-alkoxide form. It can be also conceived that the open iodonium-alkoxide form can coordinate the alkoxide moiety of a second molecule of PhS-I.[9] ENREF 15] In a solvent with poor donor ability (represented by CDCl3), the rate and extent of such dynamic processes is expected to be significant enough to lead to signal broadening. The more broadened $^{19}F$ NMR resonance is assumed to correspond to the —$CF_2$-moiety directly attached to the hypervalent iodine center where the changes of electronic properties are most pronounced during these chemical exchange processes. Addition of solvent with good donor properties (represented by MeCN) is equivalent to addition of large excess of a ligand that effectively freezes the ligand exchange equilibria, whereby only the MeCN complex of PhS-I is observed (see below). A similar behaviour was observed for arylsulfur trifluorides where exchange of axial and equatorial fluorides was "frozen" by addition of diethyl ether, although the original nature of signal broadening is not exactly the same.[10] ENREF 16]

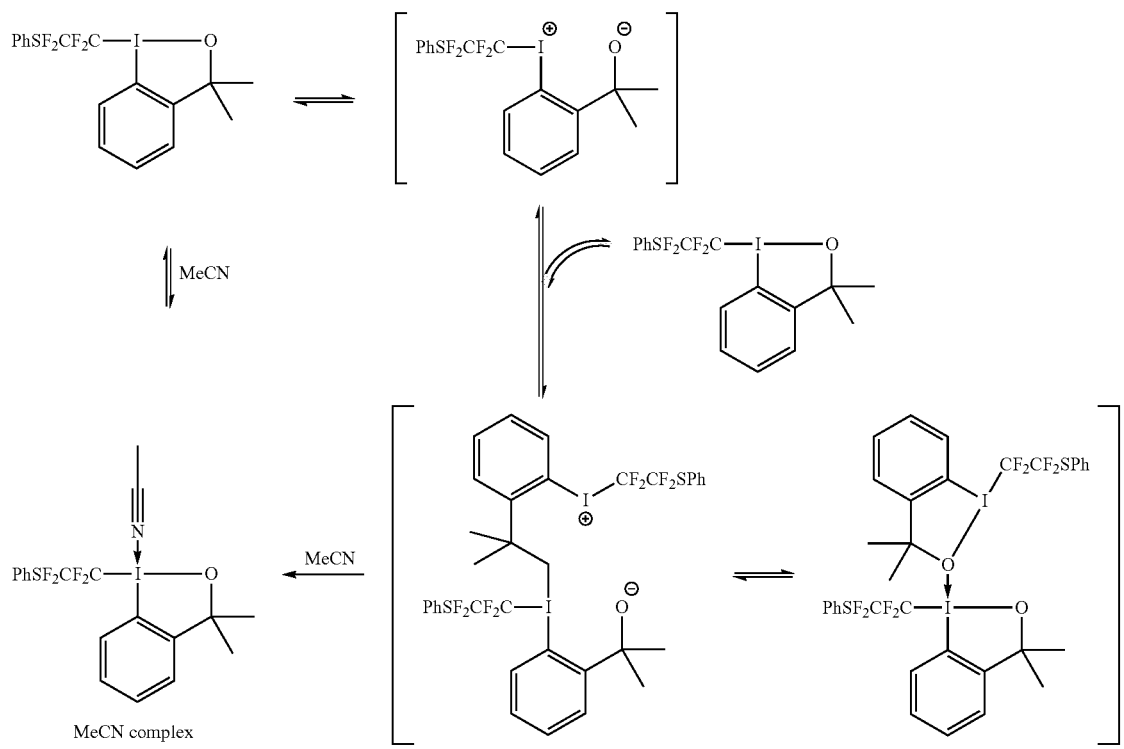

Suggested Coordination of Acetonitrile to PhS-I

Again this interpretation shall by no means be construed as limiting the scope of the present invention.

III. Storage Stability of the New $CF_2CF_2$—X Reagents

Only preliminary stability tests of reagents PhS-I, PhS-II, $PhSO_2$—I, Im-I and Im-II in the solid state and in solution in deuterated solvents ($CDCl_3$ and d3-MeCN) were performed.

All reagents could be handled for a few hours at room temperature without any decomposition. The well crystallizing reagent Im-II was stored at 25° C. for 5 days without decomposition.

However, as a solution in both $CDCl_3$ and d3-MeCN, significant decomposition (more than 50%) was detected after 24 h at room temperature, in standard borosilicate glass NMR tubes under air without exclusion of light. In the case of reagent PhS-I, severe stability problems were experienced. Partial decomposition could already be detected within 1 hour when using d3-MeCN that was not dry.

During storage of reagents PhS-I, PhS-II, $PhSO_2$—I, Im-I and Im-II for 4 months at −20° C. no decomposition was observed. It is therefore recommended to store the reagents in tightly sealed containers with exclusion of moisture at −20° C.

IV. Application of the Compounds of Formula (I) and Formula(II) in Formally Electrophilic Fluoroalkylation Reactions Based on the literature precedence of successful mild trifluoromethylation of thiols with alcohol CF3 reagent,[11] the reactivity of Im-I towards 4-chlorothiophenol was investigated. Upon addition of a solution of 1 equivalent of 4-chlorothiophenol to 1 equivalent of Im-I in DCM (dichloromethane) at −78° C., the reaction mixture instantaneously turned yellowish-green. In the trifluoromethylation reaction of thiols, this greenish coloration was assumed to be caused by intermediary formation of charge transfer complex between the reagent and the thiol substrate. This could also be the case with Im-I. Within a minute, the yellowish-green solution turned colorless and a crystalline white solid formed. After warming up to ambient temperature (20° C. to 25° C.), an almost colorless solution was obtained. $^{19}$F NMR analysis with internal standard revealed clean formation of the corresponding fluoroalkylated product in 93% yield (see Scheme below). Subsequent chromatographic isolation provided 1-[(1,1,2,2-Tetrafluoro-2-(4-chlorophenyl)]-1H-imidazole in 90% isolated yield as white needles.

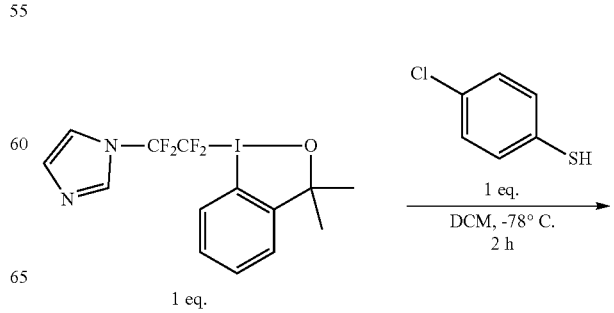

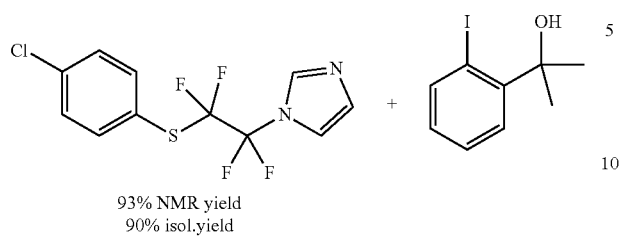

93% NMR yield
90% isol.yield

Fluoroalkylation of 4-Chlorothiophenol with Imidazole-I

Another test reaction was the fluoroalkylation of N,N-disubstituted hydroxylamines.

Treatment of 1 equivalent of N,N-dibenzylhydroxylamine with 1 equivalent of PhS-I in DCM at ambient temperature (20° C. to 25° C.) gave after overnight reaction 70% NMR yield of the corresponding fluoroalkylated hydroxylamine. Isolation by flash chromatography yielded O-fluoroalkylated N,N-dibenzylhydroxylamine in 63% yield.

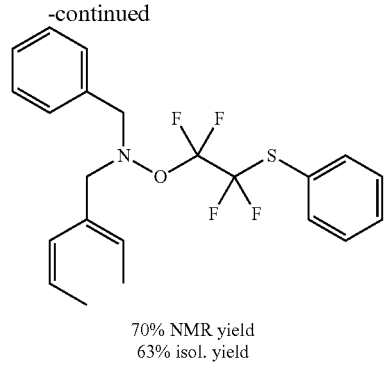

70% NMR yield
63% isol. yield

Fluoroalkylation of N,N-Dibenzylhydroxylamine with PhS-I

A further test reaction was fluoroalkylation of diphenylphosphine. Upon mixing 1 equivalent of diphenylphosphine with 1 equivalent of Im-I fast conversion to the corresponding fluoroalkylated diphenylphosphine was observed by $^{19}$F NMR. The NMR yield was 62%. Isolation has to be performed under non-oxidizing conditions.

63% NMR yield

Reactions with further substrates have also already been examined. A list with reaction conditions is given in the following Table 2.

TABLE 2

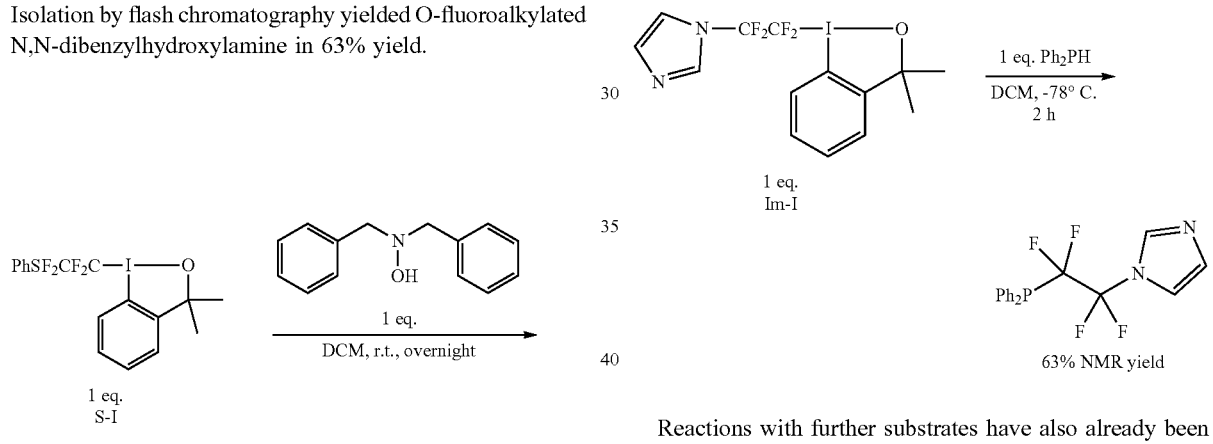

TABLE 2-continued
| Substrate (type) | Reagent | Reaction |
|---|---|---|
| 4-Cl-thiophenol (S) | A2 | 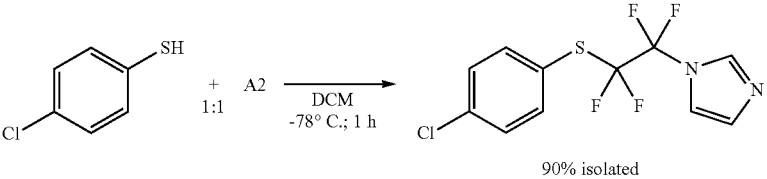 [SMILES: Sc1ccc(Cl)cc1 ; "A2" ; FC(F)(Sc1ccc(Cl)cc1)C(F)(F)n1ccnc1] |
| Diphenylphosphine (P) | A2 | 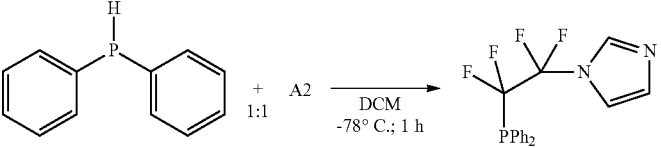 |
| Skatole (C) | A2 | 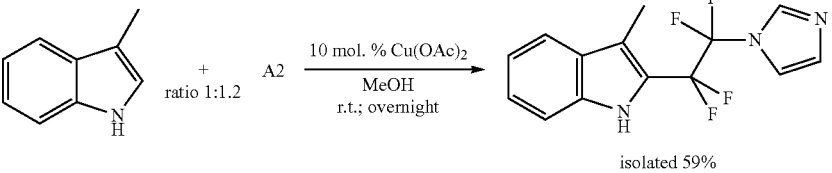 |
| β-Keto ester (C) | A4 | 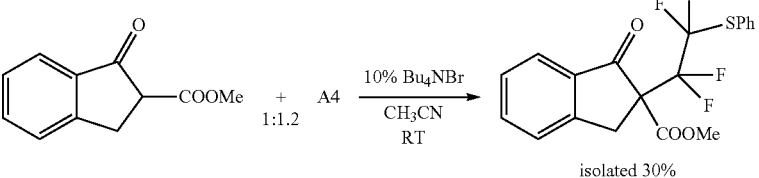 |
| β-Keto ester (C) | B4 | 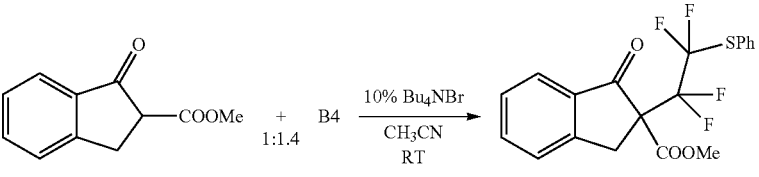 |
| Oxazolidinone 1 (C) | B4 | 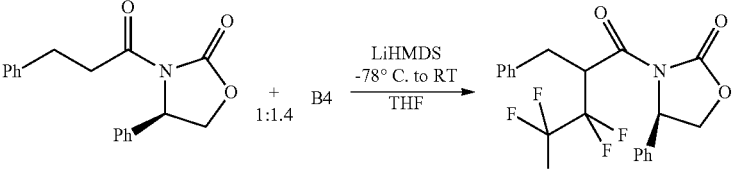 |
| Oxazolidinone 2 (C) | B4 | 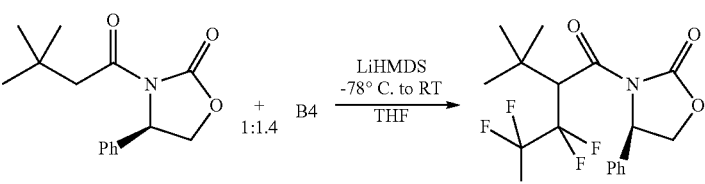 |

TABLE 2-continued

| Substrate (type) | Reagent | Reaction |
|---|---|---|
| 2-Mercapto-benzothiazol (S) | A | 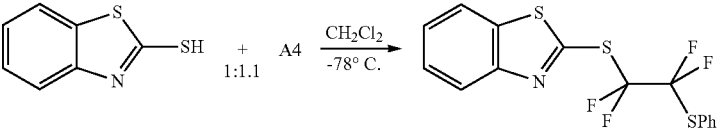<br>isolated 71% |

V. Conclusions

Fluoroiodane alcohols and fluoroiodane acids are the best Umpolung partners for fluoroalkylated silanes.

Pure fluoride catalysis with 1 mol % TBAT is able to mediate the very rapid Umpolung of nucleophilic fluoroalkylsilanes within minutes at −35° C.

Use of excess fluoroiodane alcohols and fluoroiodane acids helps to improve the yields of the desired hypervalent fluoroalkyl-iodine reagents (compounds of formula (I) and formula (II)).

VI. Use Ability of the Compounds of Formula (I) and Formula (II)

In the so far performed reactions "alcohol-type" reagents PhS-I and Im-I showed very promising potential, as thiols, N,N-disubstituted hydroxylamines, secondary phosphines and carbon centered nucleophiles proved to be receptive substrates in electrophilic fluoroalkylation. Further reactions wherein the compounds of the present invention are of interest are for example the diastereoselective fluoroalkylation of chiral Evans-type acyl oxazolidin-2-ones, fluoroalkylation of trimethylsilyl ketene acetals derived from lactones, enantioselective Cu-catalyzed fluoroalkylation of cyclic β-keto esters, fluoroalkylation of terminal acetylenes, alkenes and aryl- and alkenylboronic acids. Fluoroalkylation of heteroatom-centered nucleophiles like azoles and secondary phosphines is assumed to provide highly interesting ligand scaffolds applicable in homogeneous metal-catalyzed transformations.

The exceptional reactivity towards thiol substrates can be employed in selective tagging of cysteine residues in the context of highly complex peptide targets. For example, a reagent comprising a fluorescent moiety attached through a linker to the $CF_2CF_2$-moiety will serve as a double tag, suitable for both fluorimetric assay and NMR spectrometric detection.[12]

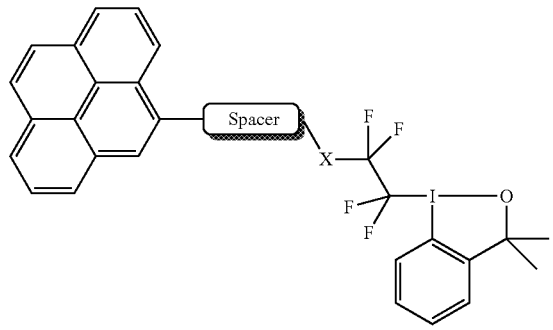

Pyrene Containing Reagent for Fluorescence Tagging of Cysteine Residues

Seen from a more general perspective, hypervalent fluoroalkyl-iodine reagents of formula (I) or formula (II) can function as highly thiol-selective carriers of a variety of moieties attached to the hypervalent iodine center.

From the life- and material science perspective, thanks to their excellent tunability, the compounds of formula (I) and formula(II) have broad application in discovery of new drugs, modification of existing lead structures and in the design of new functional materials (liquid crystals, fuel cell membranes, donor-acceptor molecular wires for solar electrochemical cells). For example, fluoroalkylation of existing drugs can improve some of their properties, for instance acidobasic behaviour or bioavailability. As an example of a modification with a compound of formula (I) or formula (II) Tenofovir may be mentioned. Tenofovir, marketed by the company Gilead Sciences, is an antiretroviral drug (reverse transcriptase inhibitor) effective against HIV1 and hepatitis B infections.

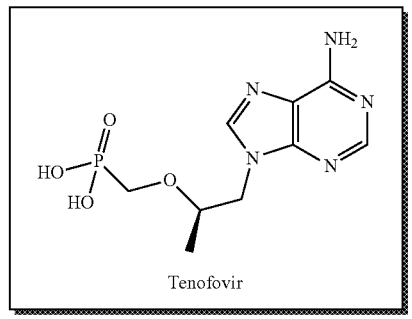

Tenofovir

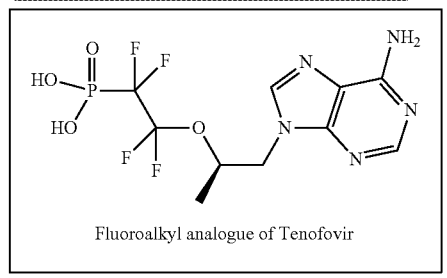

Fluoroalkyl analogue of Tenofovir

Example for Use of a Tetrafluoroethylphosphonate Moiety in the

Design of Modified Drugs While there are shown and described presently preferred embodiments of the invention, it is to be distinctly understood that the invention is not limited thereto but may be otherwise variously embodied and practiced within the scope of the following claims.

REFERENCES CITED

[1] a) P. Eisenberger, S. Gischig, A. Togni, *Chem. Eur. J.* 2006, 12, 2579-2586;
  b) P. Eisenberger, ETH Zurich, Diss. No. 17371 (Zurich), 2007.
[2] a) J. Liu, C. Ni, F. Wang, J. Hu, *Tetrahedron Lett.* 2008, 49, 1605-1608;
  b) C. Ni, J. Hu, *Tetrahedron Lett.* 2005, 46, 8273-8277.
[3] W. Zhang, J. Zhu, J. Hu, *Tetrahedron Lett.* 2008, 49, 5006-5008.
[4] Z. He, T. Luo, M. Hu, Y. Cao, J. Hu, *Angew. Chem. Int. Ed.* 2012, 51, 3944-3947.
[5] Z. He, M. Hu, T. Luo, L. Li, J. Hu, *Angew. Chem. Int. Ed.* 2012, 51, 11545-11547.
[6] Y. Li, A. Studer, *Angew. Chem. Int. Ed.* 2012, 51, 8221-8224.
[7] K. I. Petko, T. M. Sokolenko, A. V. Bezdudny, L. M. Yagupolskii, *J. Fluorine Chem.* 2005, 126, 1342-1346.
[8] W. Dmowski, *J. Fluorine Chem.* 2012, 142, 6-13.
[9] V. Zhdankin, in *Hypervalent Iodine Chemistry: Preparation, Structure and Synthetic Applications of Polyvalent Iodine Compounds*, John Wiley and Sons, 2013, pp. 21-143.
[10] T. Umemoto, R. P. Singh, Y. Xu, N. Saito, *J. Am. Chem. Soc.* 2010, 132, 18199-18205.
[11] I. Kieltsch, P. Eisenberger, A. Togni, *Angew. Chem. Int. Ed.* 2007, 46, 754-757.
[12] a) Y. Kim, S. O. Ho, N. R. Gassman, Y. Korlann, E. V. Landorf, F. R. Collart, S. Weiss, *Bioconjugate Chem.* 2008, 19, 786-791;
  b) M. C. Puljung, W. N. Zagotta, in *Current Protocols in Protein Science*, John Wiley & Sons, Inc., 2001;
[13] S. Mizuta et al., *Org. Lett.* 2013, 15, 1250-1253;
[14] B. Zhang et al., *Angew. Chem. Int. Ed.* 2013, 52, 10792-10795;
[15] Carboni et al., *Org. Lett.* 2014, 16, 1240-1243;

BRIEF DESCRIPTION OF THE FIGURES

FIG. 2 shows tagging RA-CM with various fluorescent reagents[a] and testing the retro-aldol reaction of (:)-methodol.[b].

SUMMARY

Figure 1:
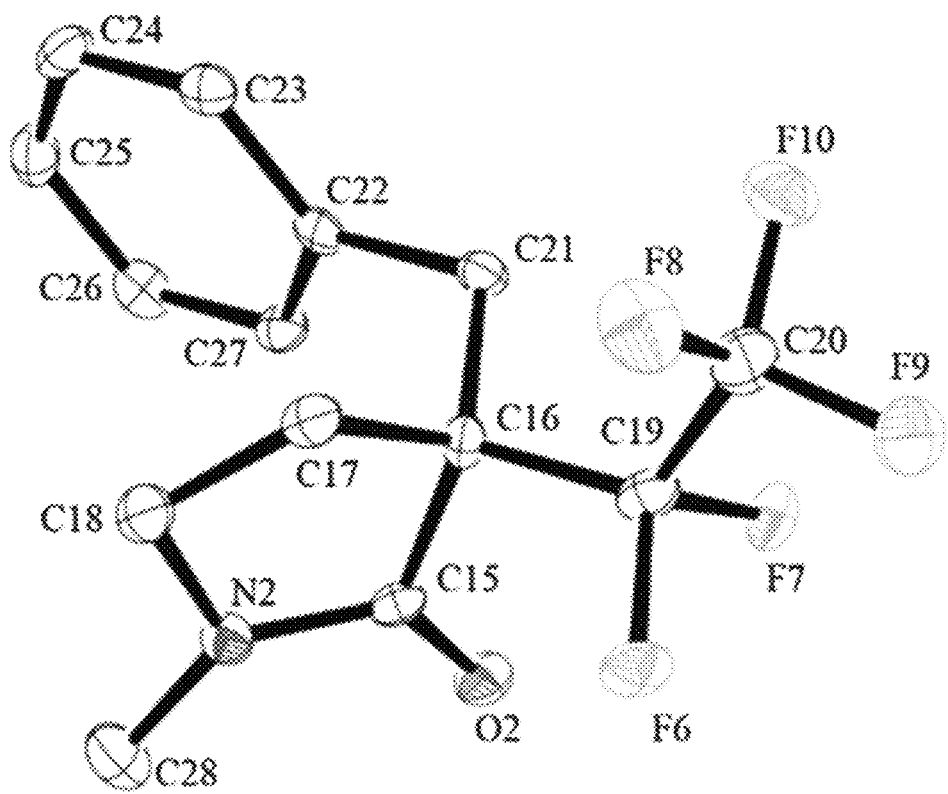
FIG. 1 shows an ORTEP view of the X-ray structure of compound 9ak. Hydrogen atoms are omitted for clarity and thermal ellipsoids are drawn at the 50% probability level. Only one of the two independent molecules in the asymmetric unit is shown. Selected bond lengths [Å] and bond angles [1]: C16-C19 1.523(5), C16-C21 1.553(5), C16-C17 1.545(5), C16-C15 1.548(5),F8-C20 1.326(5), F6-C19 1.369(4); C19-C16-C21 110.8(3), C19-C16-C17112.2(3), C19-C16-C15 108.4(3), C17-C16-C21 113.6(3). CCDC 1442867.

According to a first aspect of the invention, a compound of formula (I) or formula (II),

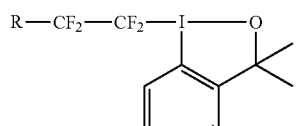

Alcohol-type reagent

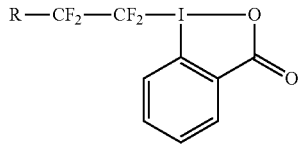

Acid-type reagent is provided, wherein
R is a nucleophile of formula III, $-L^1_a-R^1-L^2_c-R^2_d-L^3_e-E$ (III), wherein
  a is 0 or 1 and $L^1$ is selected from —O—, —S— or —$C_1$-alkyl,
  $R^1$ is selected from imidazole, pyrazole, benzimidazole, phenyl and pyridine, with $R^3$ and $R^4$ being independently from each other —H or —$C_{1-4}$-alkyl,
  c is 0 or 1 and $L^2$ is a $C_{1-4}$-alkyl,
  d is 0 or 1 and $R^2$ is selected from —C(=O)—O—, —O—(C=O)—, —N($R^5$)—, —N($R^5$)—C(=O)—, —C(=O)—N($R^5$)— and —N($R^5$)—$SO_2$—,
  with $R^5$ being selected from —H, —$C_{1-4}$-alkyl, —$C_{2-4}$-alkene, —$C_{2-4}$-alkynyl, —$SO_2$F, —CHO, —C(=O)—O-tertbutyl (Boc), —C≡C—Si($CH_3$)$_3$, 3-Oxo-4,7,7-trimethyl-2-oxabicyclo[2.2.1]heptane-1-carbonyl (camphanic carbonyl), an affinity tag or a fluorescent dye,
  e is 0 or 1 and $L^3$ is selected from —$C_{1-8}$-alkyl-, -phenyl-, —[($CH_2$)$_{1-4}$—O—]$_{1-5}$—, —[($CH_2$)$_{1-4}$—O—]$_{1-4}$—($CH_2$)$_{1-4}$—, and —[($CH_2$)$_{1-4}$—O—]$_{1-4}$-triazole-[($CH_2$)$_{1-4}$—O—]$_{1-2}$—($CH_2$)$_{1-2}$—, and
  E is selected from —H, —$C_{1-4}$-alkyl, —$C_{2-4}$-alkenyl, —$C_{2-4}$-alkynyl, —$NO_2$, halogene, particularly —I, —$NH_2$, —OH, —$C_{1-3}$—$N_3$, —$N_3$, —CN, —$SO_2$F, —CHO, —C(=O)—O-tertbutyl (Boc), —Si($CH_3$)$_3$ (TMS), —Si($CH_2$—$CH_3$)$_3$, —O—Si($CH_3$)$_3$, —O—Si($CH_2CH_3$)$_3$, —C≡C—Si($CH_3$)$_3$, 3-Oxo-4,7,7-trimethyl-2-oxabicyclo[2.2.1]heptane-1-carbonyl (camphanic carbonyl), pinalcolyl boronate, dioxolanyl, a bioorthogonal group, an affinity tag or a fluorescent dye, or
R is a nucleophile of formula IV, $-L^4_f-R^6_g-G$ (IV), wherein
  f is 0 or 1 and $L^4$ is selected from $C_{1-2}$-alkyl,
  g is 0 or 1 and $R^6$ is selected from —N($R^8$)—, —C(=O)—N($R^8$)—, —N($R^8$)—C(=O)—, with $R^8$ being selected from —H, —$C_{1-4}$-alkyl, —$C_{2-4}$-alkene, —$C_{2-4}$-alkynyl, —$C_{1-3}$—$N_3$, —C(=O)—O-tertbutyl (Boc), an affinity tag or a fluorescent dye,
  in case of f is 0 and g is 0, G is selected from —$C_{1-4}$-alkyl, —$C_{2-4}$-alkene, —$C_{2-4}$-alkynyl, —$C_{1-3}$—$N_3$, —$N_3$, —C(=O)—O-tertbutyl (Boc), a bioorthogonal group, an affinity tag or a fluorescent dye, in all other cases, G is selected from —H, —$C_{1-4}$-alkyl, —$C_{2-4}$-alkene, —$C_{2-4}$-alkynyl, —$C_{1-3}$—$N_3$, —$N_3$, —C(=O)—O-tertbutyl (Boc), a bioorthogonal group, an affinity tag or a fluorescent dye.

For a skilled person it is obvious that a bond between two heteroatoms (e.g. —O—N— or —N—Si—) will lead to an unstable compound. Thus, the moiety E may only be combined with a moiety $R^1$, $L^2$, $R^2$ or $L^3$ in such a way that a stable bond results. This means, the moieties —$NO_2$, —$NH_2$, —$N_3$, —Si($CH_3$)$_3$ may be connected to a C-atom. The same applies for the moiety G.

The double and triple bond of alkene or alkynyl moieties is preferably located at the distal end of the alkene or alkynyl moiety, i.e. the alkene or alkynyl moiety is connected to the parent moiety by a single bonded C atom, e.g. —$CH_2$—CH=$CH_2$.

In some embodiments, R is a nucleophile of formula III, -$L^1_a$-$R^1$-$L^2_c$-$R^2_d$-$L^3_e$-E (III), wherein
 a is 0 or 1 and $L^1$ is selected from —O—, or —$C_1$-alkyl,
 $R^1$ is phenyl,
 c is 0 or 1 and $L^2$ is a $C_{1-4}$-alkyl, in particular $C_{1-2}$-alkyl,
 d is 0 or 1 and $R^2$ is selected from —C(=O)—O—, —N($R^5$)—, —N($R^5$)—C(=O)—, and —N($R_5$)—$SO_2$—,
  with $R^5$ being selected from —H, —$C_{1-4}$-alkyl, in particular —$C_{1-2}$-alkyl, C(=O)—O-tertbutyl (Boc),
 e is 0 or 1 and $L^3$ is selected from —$C_{1-6}$-alkyl-, in particular $C_{1-3}$-alkyl, -phenyl-, —[($CH_2$)$_{1-4}$—O—]$_{1-5}$—, —[($CH_2$)$_{1-2}$—O—]$_{1-4}$—($CH_2$)$_{1-2}$—, and —[($CH_2$)$_{1-2}$—O—]$_{1-4}$-triazole-[($CH_2$)$_{1-2}$—O—]$_1$—($CH_2$)—, and
 E is selected from —H, —$C_{1-4}$-alkyl, —$C_{2-4}$-alkynyl, —$NO_2$, halogene, particularly —I, —$C_{1-3}$—$N_3$, —$N_3$, —CN, —$SO_2$F, —CHO, —C(=O)—O-tertbutyl (Boc), —C≡C—Si($CH_3$)$_3$, 3-Oxo-4,7,7-trimethyl-2-oxabicyclo[2.2.1]heptane-1-carbonyl (camphanic carbonyl), an affinity tag or a fluorescent dye, or
R is a nucleophile of formula IV, -$L^4_f$-$R^6_g$-G (IV), wherein
 f is 0 or 1 and $L^4$ is selected from $C_{1-2}$-alkyl,
 g is 0 or 1 and $R^6$ is selected from —N($R^8$)—, —C(=O)—N($R^8$)—,
  with $R^8$ being selected from —H, —$C_{1-4}$-alkyl, in particular $C_{1-2}$-alkyl, —$C_{2-4}$-alkenyl, in particular $C_2$-alkenyl, —C(=O)—O-tertbutyl (Boc),
 in case of f is 0 and g is 0, G is selected from —$C_{1-4}$-alkyl, in particular $C_{1-2}$-alkyl, —$C_{2-4}$-alkenyl, in particular $C_2$-alkenyl, —$N_3$, —C(=O)—O-tertbutyl (Boc), in all other cases, G is selected from —H, —$C_{1-4}$-alkyl, in particular $C_{1-2}$-alkyl, —$C_{2-4}$-alkenyl, in particular $C_2$-alkenyl, —$N_3$, —C(=O)—O-tertbutyl (Boc).

In some embodiments, the biorthogonal group is azide, pikolyl azide or fluoralkyl azide.

Fluoralkyl azide is a moiety —R—$CF_2$—$N_3$, wherein R is a $C_{0-4}$-alkyl.

In some embodiments, the affinity tag is selected from biotin tag or Myc tag.

In some embodiments, the affinity tag is a biotin tag.

In some embodiments, the fluorescent dye is selected from coumarin type dyes, rhodamine type dyes, pyrene and fluoresceine.

In some embodiments, the fluorescent dye is selected from

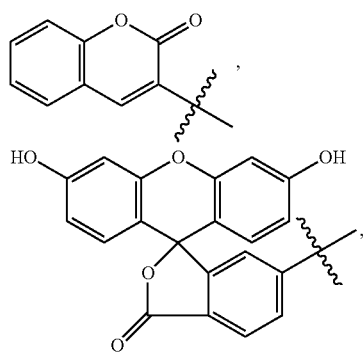

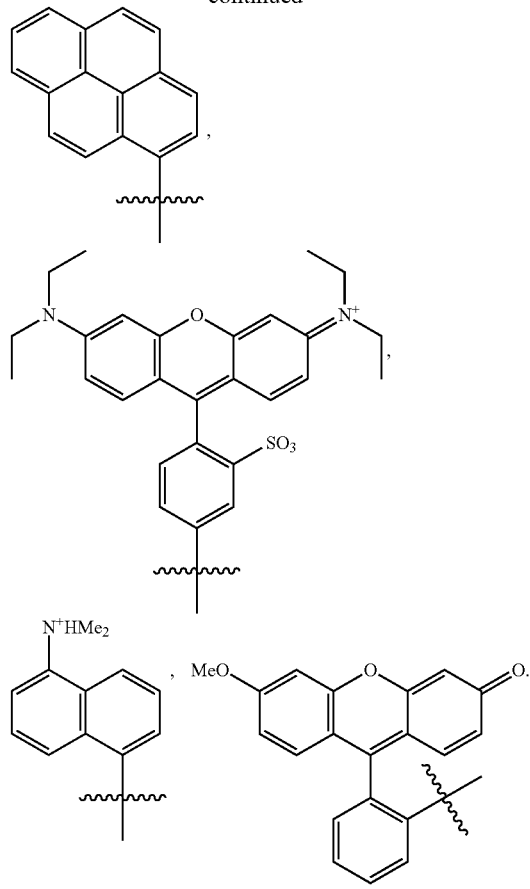

In some embodiments, $L^1$ is selected from —O— or $C_1$-alkyl.

In some embodiments, $R^1$ is phenyl.
In some embodiments, $L^2$ is selected from $C_{1-4}$-alkyl.
In some embodiments, $L^2$ is selected from $C_{1-2}$-alkyl.
In some embodiments, $R^2$ is selected from —C(=O)—O—, —N($R^5$)—, —N($R^5$)—C(=O)— with $R^5$ being selected from $C_{1-4}$-alkyl.
In some embodiments, $R^2$ is selected from —C(=O)—O—, —N($R^5$)—, —N($R^5$)—C(=O)— with $R^5$ being selected from $C_{1-2}$-alkyl.
In some embodiments, $R^2$ is selected from —C(=O)—O—, —N($R^5$)—, —N($R^5$)—C(=O)— with $R^5$ being methyl.
In some embodiments, $L^3$ is selected from —$C_{1-6}$-alkyl.
In some embodiments, $L^3$ is selected from $C_{1-3}$-alkyl.
In some embodiments, $L^3$ is propyl.
In some embodiments, E is selected from —H, —$C_{1-2}$-alkyl, —$N_3$, —C(=O)—O-tertbutyl (Boc).
In some embodiments, E is selected from —$C_{1-2}$-alkyl, —$N_3$, —C(=O)—O-tertbutyl (Boc).
In some embodiments, R in formula I is a nucleophile of formula III, -$L^1_a$-$R^1$-$L^2_c$-$R^2_d$-$L^3_e$-E (III), wherein
 a is 0 or 1 and $L^1$ is selected from —O—, or —$C_1$-alkyl, in particular —O—,
 $R^1$ is selected from phenyl, and phenyl-dioxolane, in particular phenyl,
 c is 1 and $L^2$ is a $C_{1-4}$-alkyl, in particular $C_{1-2}$-alkyl,
 d is 1 and $R^2$ is selected from —C(=O)—O—, —N($R^5$)—, —N($R^5$)—C(=O)—, and —N($R^5$)—$SO_2$—, in particular —N($R^5$)—, —N($R^5$)—C(=O)—, more particularly —N(R$^5$)—C(=O)—, with R$^5$ being selected from —H, —C$_{1-4}$-alkyl, in particular —C$_{1-2}$-alkyl, C(=O)—O-tertbutyl (Boc), R$^5$ being in particular C$_{1-2}$ alkyl, more particularly methyl, e is 0 or 1 and L$^3$ is propyl, and E is selected from —H, —C$_{1-4}$-alkyl, —C$_{2-4}$-alkynyl, —NO$_2$, halogene, particularly —I, —C$_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag or a fluorescent dye, or a is 0 or 1 and L$^1$ is selected from —O—, or —C$_1$-alkyl, in particular —O—, R$^1$ is selected from phenyl, and phenyl-dioxolane, in particular phenyl, c is 1 and L$^2$ is a C$_{1-4}$-alkyl, in particular C$_{1-2}$-alkyl, d is 1 and R$^2$ is selected from —C(=O)—O—, —N(R$^5$)—, —N(R$^5$)—C(=O)—, and —N(R$^5$)—SO$_2$—, in particular —N(R$^5$)—, —N(R$^5$)—C(=O)—, more particularly —N(R$^5$)—C(=O)—, with R$^5$ being selected from —H, —C$_{1-4}$-alkyl, in particular —C$_{1-2}$-alkyl, C(=O)—O-tertbutyl (Boc), R$^5$ being in particular C$_{1-2}$ alkyl, more particularly methyl, e is 0 or 1 and L$^3$ is selected from —C$_{1-6}$-alkyl-, in particular C$_{1-3}$-alkyl, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, in particular C$_{1-3}$ alkyl, and E is —N$_3$.

In some embodiments, R in formula I is a nucleophile of formula III, -L$^1_a$-R$^1$-L$^2_c$-R$^2_d$-L$^3_e$-E (III), wherein a is 0 or 1 and L$^1$ is selected from —O—, or —C$_1$-alkyl, in particular —O—, R$^1$ is selected from phenyl, and phenyl-dioxolane, in particular phenyl, c is 1 and L$^2$ is a C$_{1-4}$-alkyl, in particular C$_{1-2}$-alkyl, d is 1 and R$^2$ is selected from —C(=O)—O—, —N(R$^5$)—, —N(R$^5$)—C(=O)—, and —N(R$^5$)—SO$_2$—, in particular —N(R$^5$)—, —N(R$^5$)—C(=O)—, more particularly —N(R$^5$)—C(=O)—, with R$^5$ being selected from —H, —C$_{1-4}$-alkyl, in particular —C$_{1-2}$-alkyl, C(=O)—O-tertbutyl (Boc), R$^5$ being in particular C$_{1-2}$ alkyl, more particularly methyl, e is 0 or 1 and L$^3$ is propyl, and E is selected from —H, —C$_{1-4}$-alkyl, —C$_{2-4}$-alkynyl, —NO$_2$, halogene, particularly —I, —C$_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag or a fluorescent dye.

In some embodiments, R in formula I is a nucleophile of formula III, -L$^1_a$-R$^1$-L$^2_c$-R$^2_d$-L$^3_e$-E (III), wherein a is 0 or 1 and L$^1$ is selected from —O—, or —C$_1$-alkyl, in particular —O—, R$^1$ is selected from phenyl, and phenyl-dioxolane, in particular phenyl, c is 1 and L$^2$ is a C$_{1-4}$-alkyl, in particular C$_{1-2}$-alkyl, d is 1 and R$^2$ is selected from —C(=O)—O—, —N(R$^5$)—, —N(R$^5$)—C(=O)—, and —N(R$^5$)—SO$_2$—, in particular —N(R$^5$)—, —N(R$^5$)—C(=O)—, more particularly —N(R$^5$)—C(=O)—, with R$^5$ being selected from —H, —C$_{1-4}$-alkyl, in particular —C$_{1-2}$-alkyl, C(=O)—O-tertbutyl (Boc), R$^5$ being in particular C$_{1-2}$ alkyl, more particularly methyl, e is 0 or 1 and L$^3$ is selected from —C$_{1-6}$-alkyl-, in particular C$_{1-3}$-alkyl, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, in particular C$_{1-3}$ alkyl, and E is —N$_3$.

In some embodiments, R in formula I or II, in particular in formula I, is of formula III, wherein a is 0 and L$^1$ is selected from —O—, or —C$_1$-alkyl, R$^1$ is selected from phenyl, and phenyl-dioxolane, in particular phenyl, c is 0 or 1 and L$^2$ is a C$_{1-4}$-alkyl, in particular C$_{1-2}$-alkyl, d is 0 or 1 and R$^2$ is selected from —C(=O)—O—, —N(R$^5$)—, —N(R$^5$)—C(=O)—, and —N(R$^5$)—SO$_2$—, with R$^5$ being selected from —H, —C$_{1-4}$-alkyl, in particular —C$_{1-2}$-alkyl, C(=O)—O-tertbutyl (Boc), e is 0 or 1 and L$^3$ is selected from —C$_{1-6}$-alkyl-, in particular C$_{1-3}$-alkyl, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, and E is selected from —H, —C$_{1-4}$-alkyl, —C$_{2-4}$-alkynyl, —NO$_2$, halogene, particularly —I, —C$_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag or a fluorescent dye.

In some embodiments, R in formula II is of formula III, wherein

R is a nucleophile of formula III, -L$^1_a$-R$^1$-L$^2_c$-R$^2_d$-L$^3_e$-E (III), wherein a is 0 or 1 and L$^1$ is selected from —O—, or —C$_1$-alkyl, R$^1$ is selected from phenyl, and phenyl-dioxolane, in particular phenyl, c is 1 and L$^2$ is a C$_{1-4}$-alkyl, in particular C$_{1-2}$-alkyl, d is 0 or 1 and R$^2$ is selected from —C(=O)—O—, —N(R$^5$)—, —N(R$^5$)—C(=O)—, and —N(R$_5$)—SO$_2$—, with R$^5$ being selected from —H, —C$_{1-4}$-alkyl, in particular —C$_{1-2}$-alkyl, C(=O)—O-tertbutyl (Boc), e is 0 or 1 and L$^3$ is selected from —C$_{1-6}$-alkyl-, in particular C$_{1-3}$-alkyl, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, and E is selected from —H, —C$_{1-4}$-alkyl, —C$_{2-4}$-alkynyl, —NO$_2$, halogene, particularly —I, —C$_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag or a fluorescent dye, or R is a nucleophile of formula III, -L$^1_a$-R$^1$-L$^2_c$-R$^2_d$-L$^3_e$-E (III), wherein a is 0 or 1 and L$^1$ is selected from —O—, or —C$_1$-alkyl, R$^1$ is selected from phenyl, and phenyl-dioxolane, in particular phenyl, c is 0 or 1 and L$^2$ is a C$_{1-4}$-alkyl, in particular C$_{1-2}$-alkyl, d is 0 or 1 and R$^2$ is selected from —C(=O)—O—, —N(R$^5$)—, —N(R$^5$)—C(=O)—, and —N(R$_5$)—SO$_2$—, with R$^5$ being selected from —H, —C$_{1-4}$-alkyl, in particular —C$_{1-2}$-alkyl, C(=O)—O-tertbutyl (Boc), e is 0 or 1 and $L^3$ is selected from —$C_{1-6}$-alkyl-, in particular $C_{1-3}$-alkyl, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, and E is selected from —$C_{1-4}$-alkyl, —$C_{2-4}$-alkynyl, —NO$_2$, halogene, particularly —I, —$C_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag or a fluorescent dye.

In some embodiments, R in formula II is of formula III, wherein

R is a nucleophile of formula III, -L$^1_a$-R$^1$-L$^2_c$-R$^2_d$-L$^3_e$-E (III), wherein
 a is 0 or 1 and L$^1$ is selected from —O—, or —$C_1$-alkyl,
 R$^1$ is selected from phenyl, and phenyl-dioxolane, in particular phenyl,
 c is 1 and L$^2$ is a $C_{1-4}$-alkyl, in particular $C_{1-2}$-alkyl,
 d is 0 or 1 and R$^2$ is selected from —C(=O)—O—, —N(R$^5$)—, —N(R$^5$)—C(=O)—, and —N(R$_5$)—SO$_2$—,
  with R$^5$ being selected from —H, —$C_{1-4}$-alkyl, in particular —$C_{1-2}$-alkyl, C(=O)—O-tertbutyl (Boc),
 e is 0 or 1 and L$^3$ is selected from —$C_{1-6}$-alkyl-, in particular $C_{1-3}$-alkyl, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, and
 E is selected from —H, —$C_{1-4}$-alkyl, —$C_{2-4}$-alkynyl, —NO$_2$, halogene, particularly —I, —$C_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag or a fluorescent dye.

In some embodiments, R in formula II is of formula III, wherein

R is a nucleophile of formula III, -L$^1_a$-R$^1$-L$^2_c$-R$^2_d$-L$^3_e$-E (III), wherein
 a is 0 or 1 and L$^1$ is selected from —O—, or —$C_1$-alkyl,
 R$^1$ is selected from phenyl, and phenyl-dioxolane, in particular phenyl,
 c is 0 or 1 and L$^2$ is a $C_{1-4}$-alkyl, in particular $C_{1-2}$-alkyl,
 d is 0 or 1 and R$^2$ is selected from —C(=O)—O—, —N(R$^5$)—, —N(R$^5$)—C(=O)—, and —N(R$_5$)—SO$_2$—,
  with R$^5$ being selected from —H, —$C_{1-4}$-alkyl, in particular —$C_{1-2}$-alkyl, C(=O)—O-tertbutyl (Boc),
 e is 0 or 1 and L$^3$ is selected from —$C_{1-6}$-alkyl-, in particular $C_{1-3}$-alkyl, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, and
 E is selected from —$C_{1-4}$-alkyl, —$C_{2-4}$-alkynyl, —NO$_2$, halogene, particularly —I, —$C_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag or a fluorescent dye.

In some embodiments, R is a nucleophile of formula IV.

In some embodiments, R in formula I or II, in particular I, is a nucleophile of formula IV, -L$^4_f$-R$^6_g$-G (IV), wherein f is 0 or 1, in particular 1, and L$^4$ is selected from $C_{1-2}$-alkyl, in particular $C_2$-alkyl,
 g is 0 or 1 and R$^6$ is selected from —N(R$^8$)—, —C(=O)—N(R$^8$)—, in particular —N(R$^8$)—
  with R$^8$ being selected from —$C_{1-4}$-alkyl, in particular $C_{1-2}$-alkyl, —C(=O)—O-tertbutyl (Boc), more particular methyl or Boc,
 in case of f is 0 and g is 0, G is selected from —$C_{1-4}$-alkyl, in particular $C_{1-2}$-alkyl, $C_2$-alkenyl, —N$_3$, —C(=O)—O-tertbutyl (Boc), in all other cases, G is selected from —H, —$C_{1-4}$-alkyl, in particular $C_{1-2}$-alkyl, $C_2$-alkenyl, —N$_3$, —C(=O)—O-tertbutyl (Boc).

In some embodiments, R in formula I, is a nucleophile of formula IV, -L$^4_f$-R$^6_g$-G (IV), wherein f is 0 or 1, in particular 1, and L$^4$ is selected from $C_{1-2}$-alkyl, in particular $C_2$-alkyl,
 g is 0 or 1 and R$^6$ is selected from —N(R$^8$)—, —C(=O)—N(R$^8$)—, in particular —N(R$^8$)—
  with R$^8$ being selected from —$C_{1-4}$-alkyl, in particular $C_{1-2}$-alkyl, —C(=O)—O-tertbutyl (Boc), more particular methyl or Boc,
 in case of f is 0 and g is 0, G is selected from —$C_{1-4}$-alkyl, in particular $C_{1-2}$-alkyl, $C_2$-alkenyl, —N$_3$, —C(=O)—O-tertbutyl (Boc), in all other cases, G is selected from —H, —$C_{1-4}$-alkyl, in particular $C_{1-2}$-alkyl, $C_2$-alkenyl, —N$_3$, —C(=O)—O-tertbutyl (Boc).

In some embodiments, R in formula I or II, in particular I, is a nucleophile of formula IV, -L$^4_f$-R$^6_g$-G (IV), wherein f is 1, and L$^4$ is $C_2$-alkyl,
 g is 0 or 1 and R$^6$ is —N(R$^8$)—
  with R$^8$ being selected from —$C_{1-2}$-alkyl, —C(=O)—O-tertbutyl (Boc), particular methyl or Boc,
 G is selected from —H, —$C_{1-2}$-alkyl, —$C_2$-alkenyl, —N$_3$, —C(=O)—O-tertbutyl (Boc).

In some embodiments, the compound is a salt of the compound according to formula I or of the compound according to formula II, in particular an acid addition salt comprising HCl or CF$_3$COOH.

In some embodiments, the compound of formula I or II is selected from

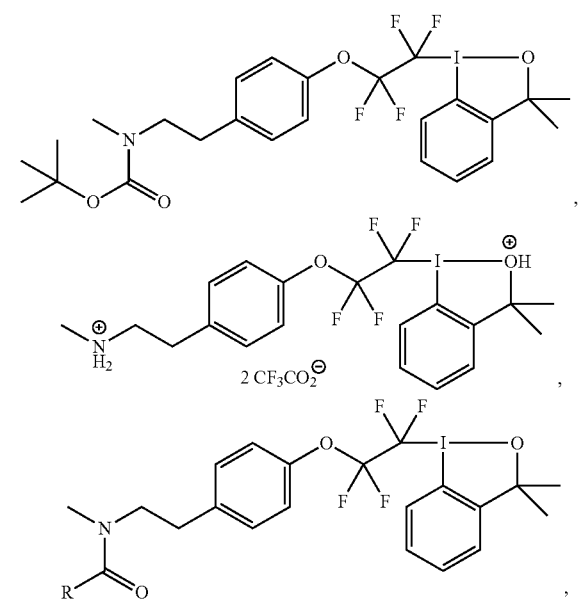

35
-continued
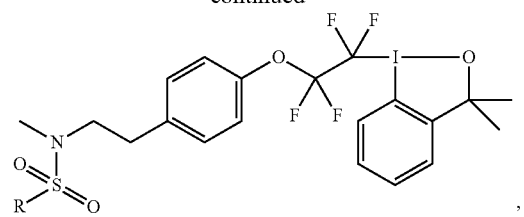
R can be biotin, fluorescent dye, etc...
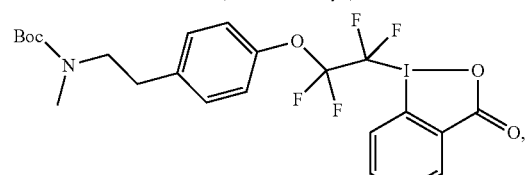
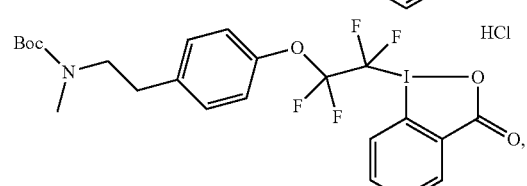
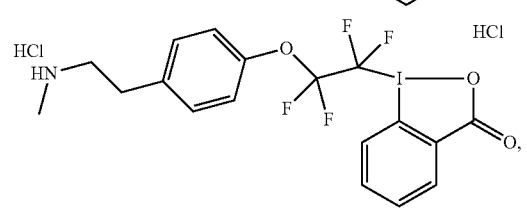
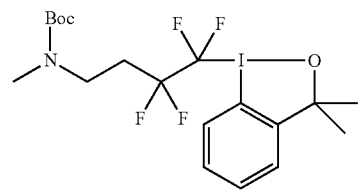
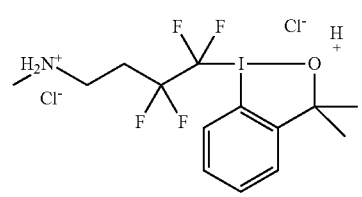
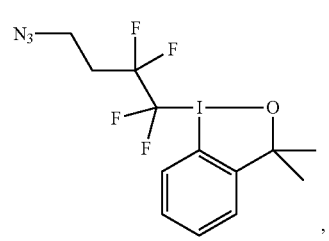
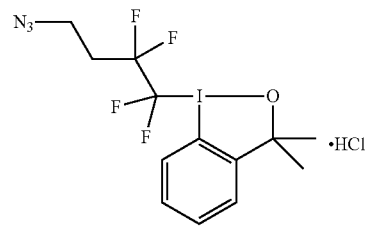
36
-continued
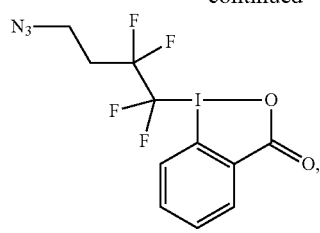
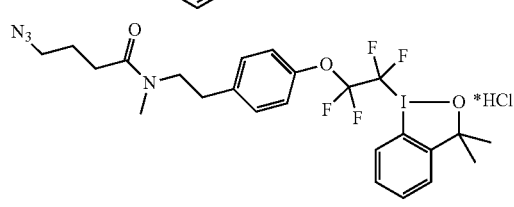
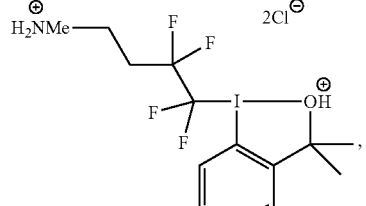
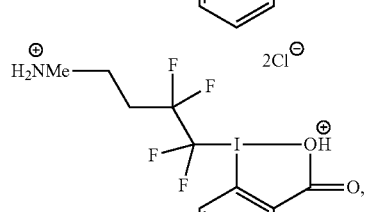
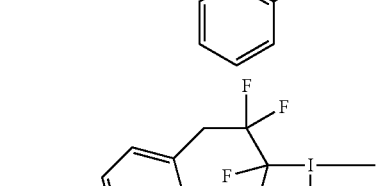
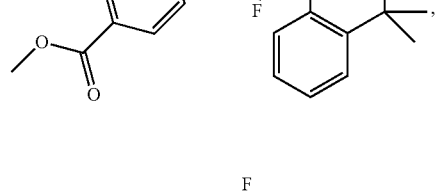
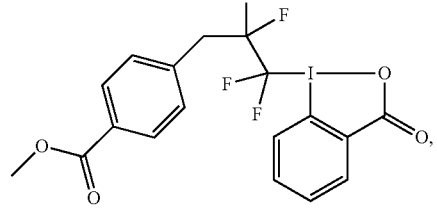
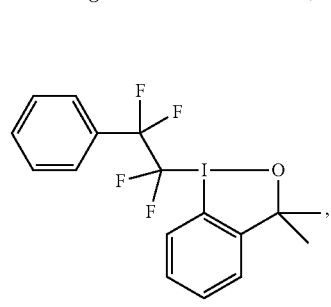

-continued
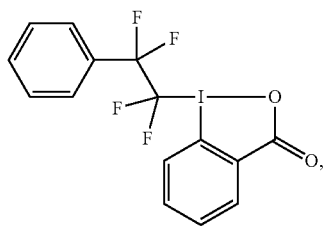
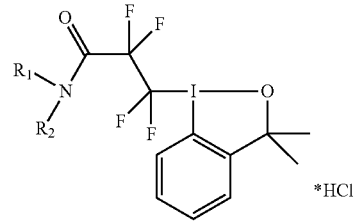
with R1 and R2 being unequal H, R1 and R2 preferably being alkyl,
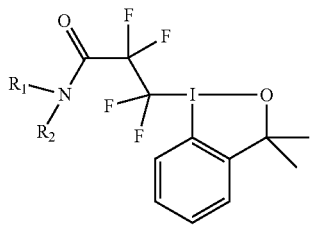
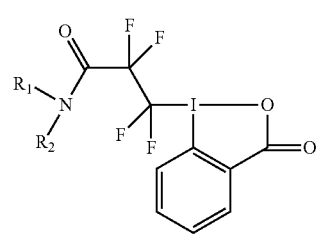
with R1 and R2 being unequal H, R1 and R2 preferably being alkyl,
with R1 and R2 being unequal H, R1 and R2 preferably being alkyl
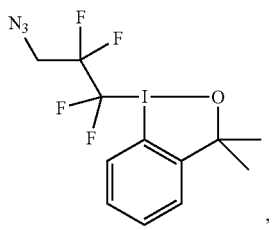 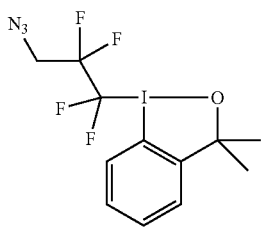 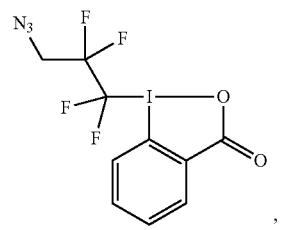
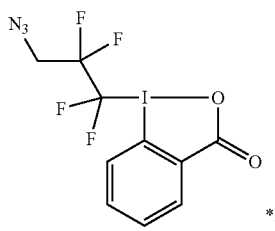 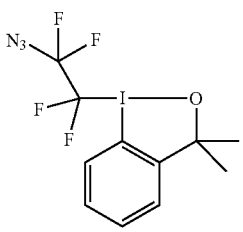 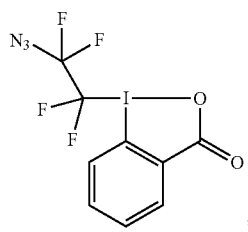
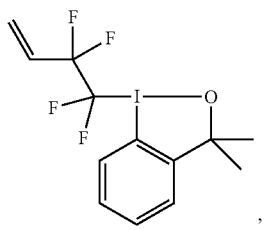 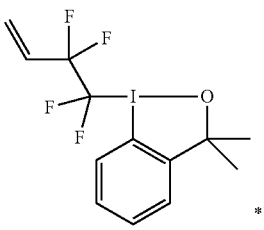 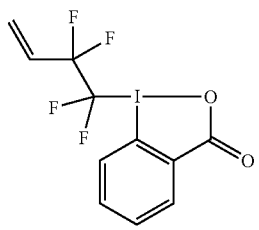 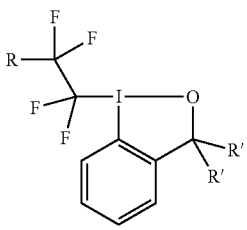
(R = SAr, OAr, Ar$_{het}$)
3: R' = Me; 3': 2R' = O

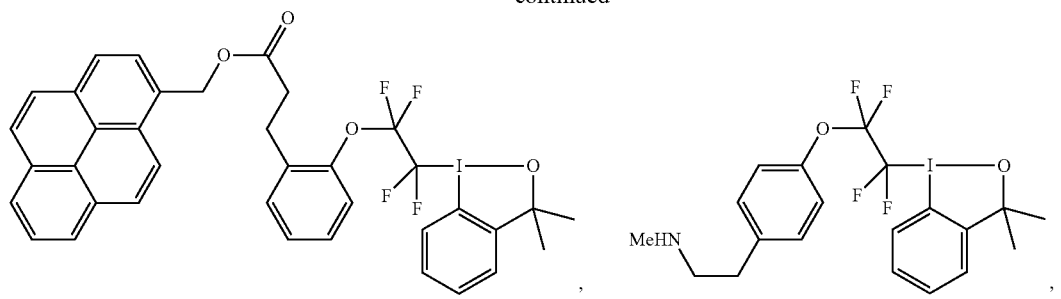
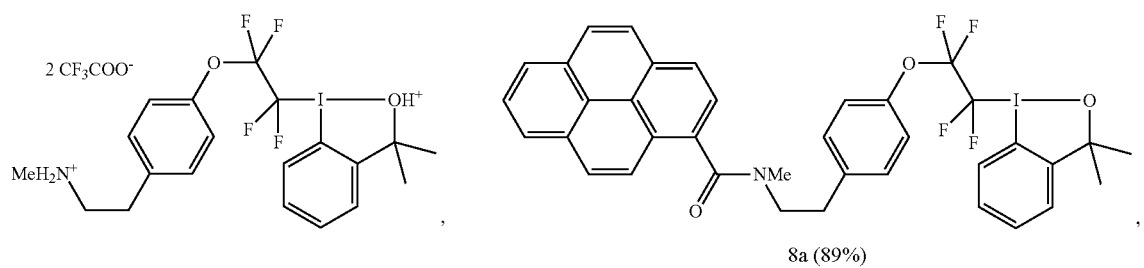
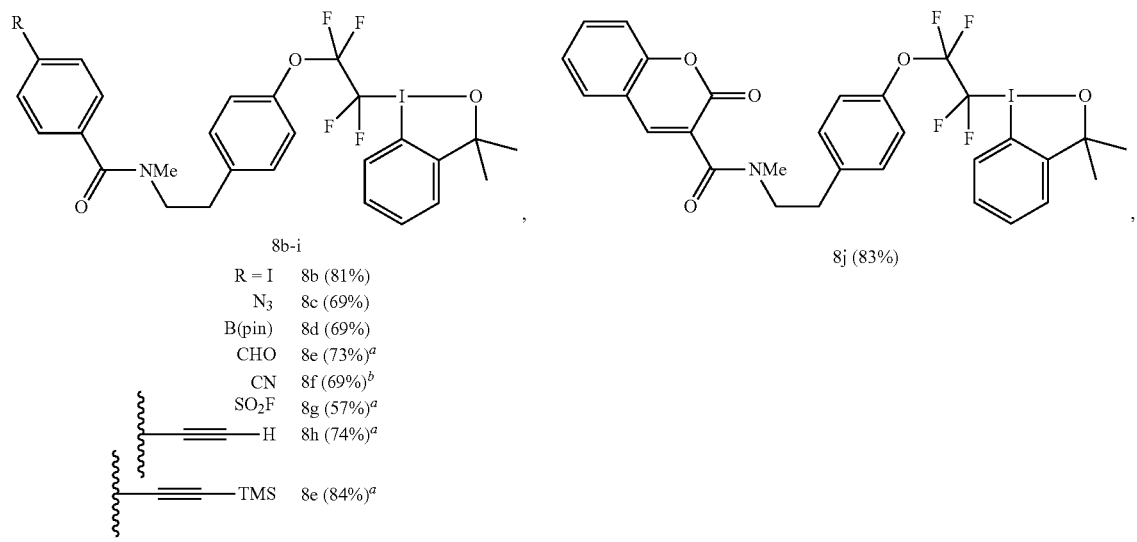
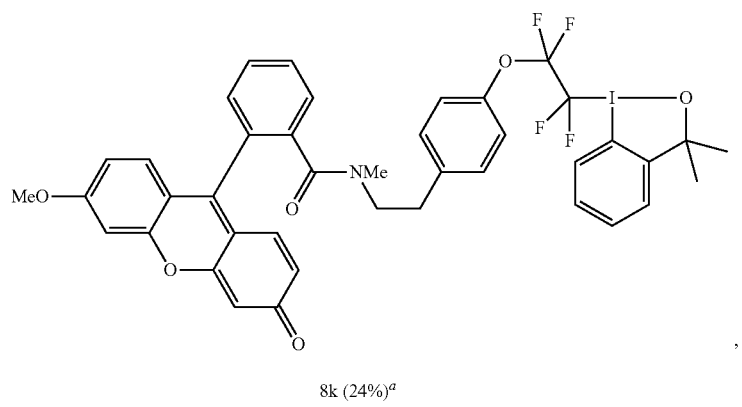

-continued
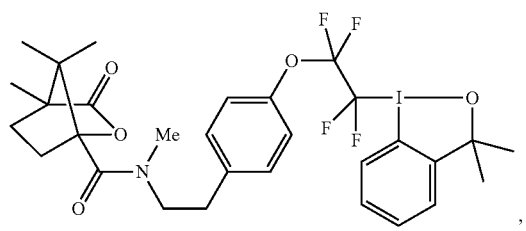
8l (71%)
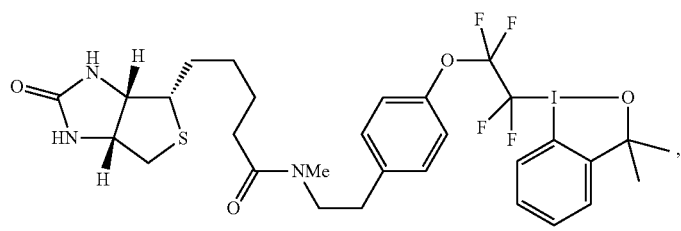
8m (42%)[a,b]
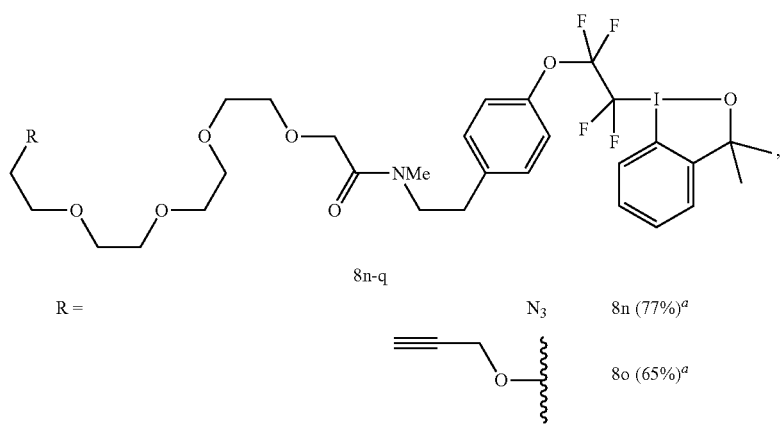
8n-q
R =  N₃  8n (77%)[a]
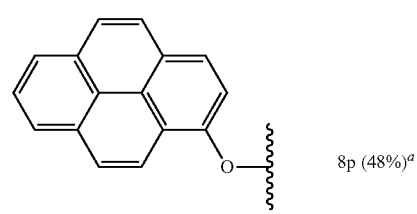  8o (65%)[a]
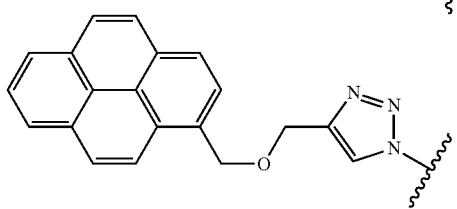  8p (48%)[a]
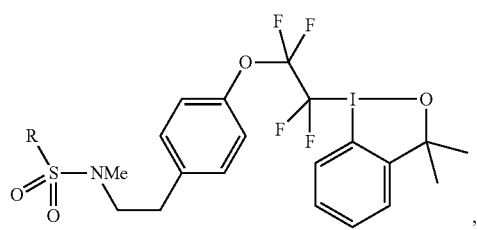
9
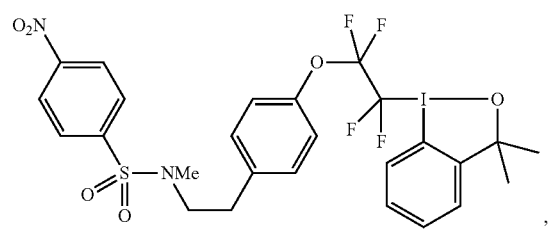
9a (85%)

-continued
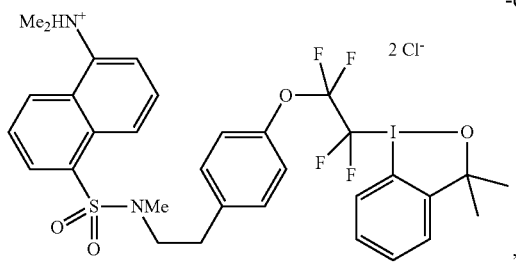
9b (90%)
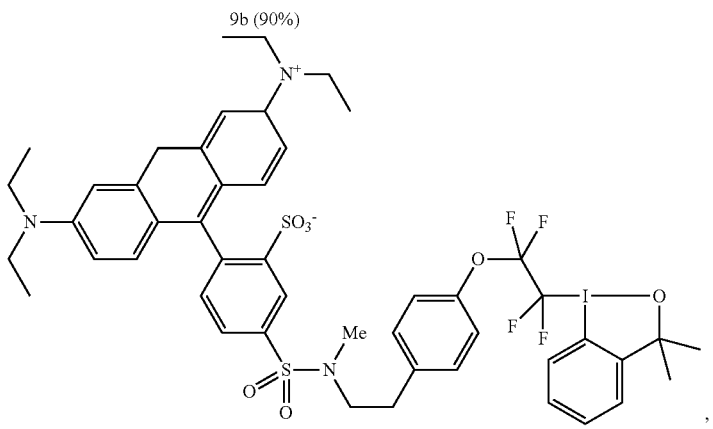
9c (46%)
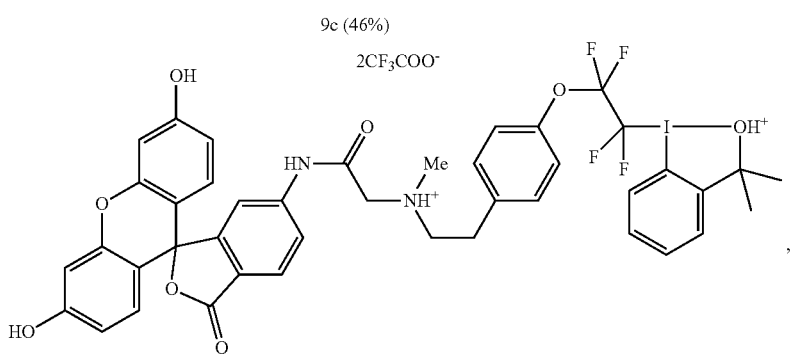
10a (93%)
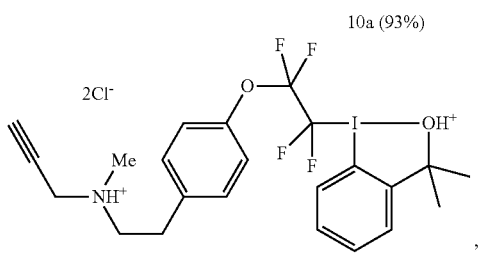
10b (56%)
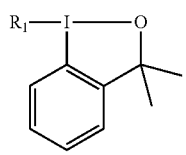
2b-k
$R_f$ is selected from
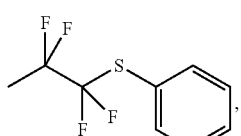
91%
9ab
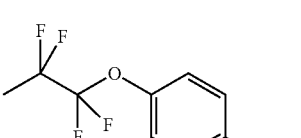
88%
9ac

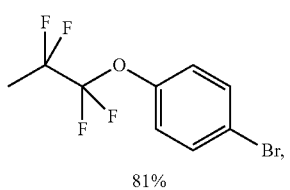
81%
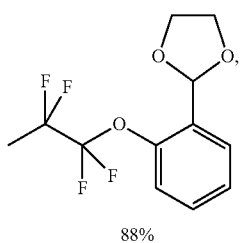
88%
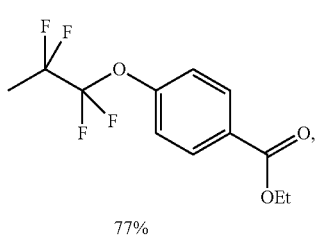
77%
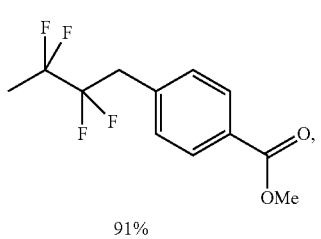
91%
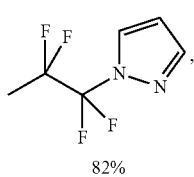
82%
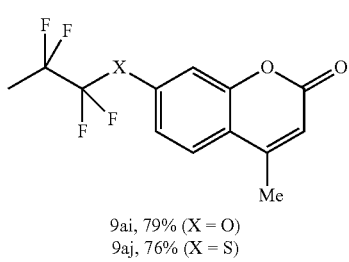
9ai, 79% (X = O)
9aj, 76% (X = S)
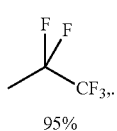
95%
In some embodiments, the compound of formula is selected from
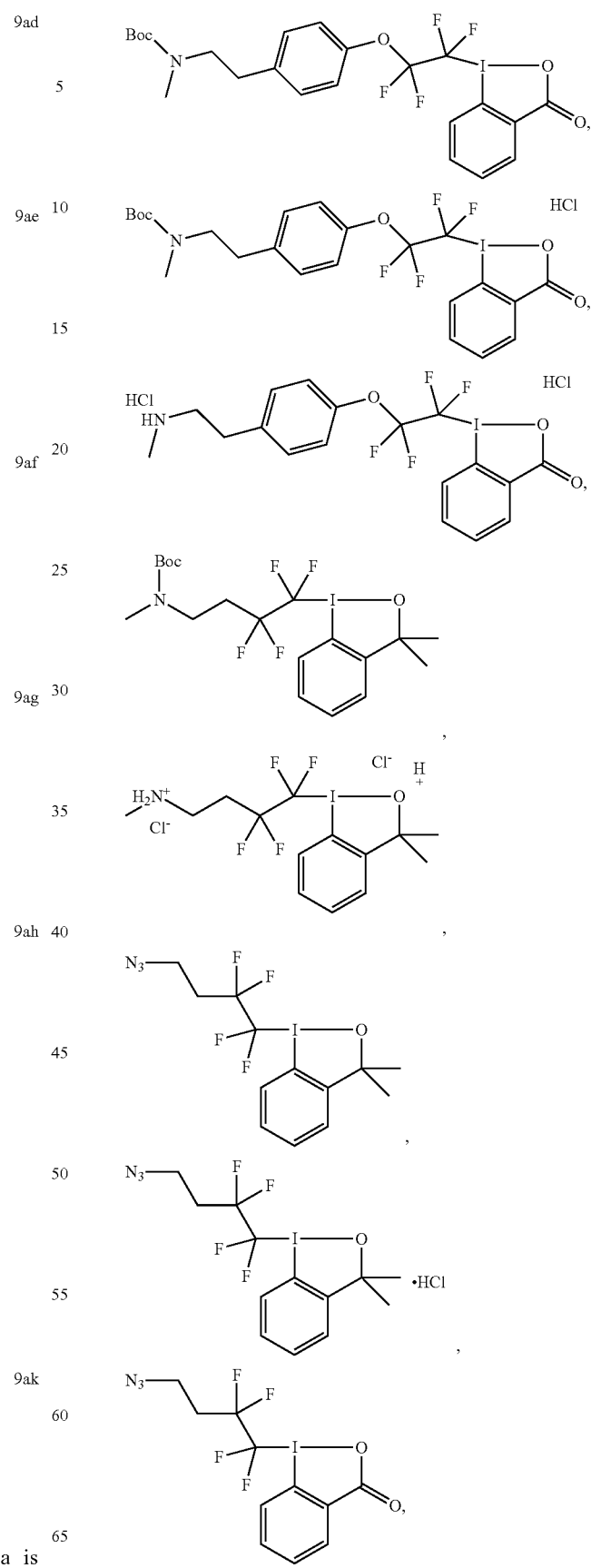

-continued
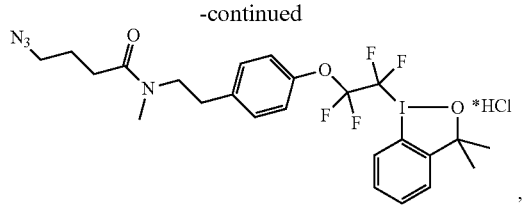
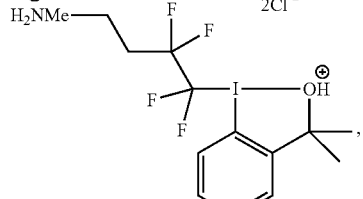
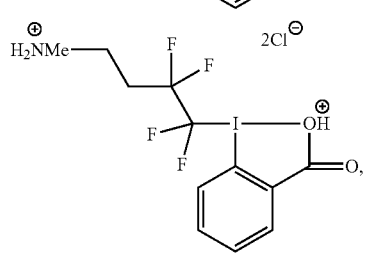
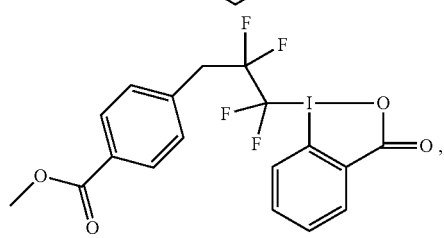
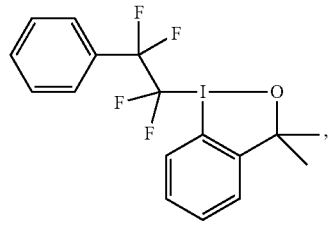
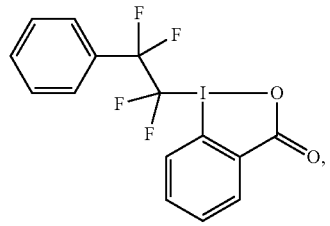
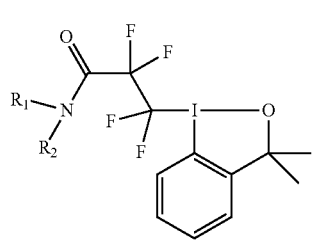
with R1 and R2 being unequal H, R1 and R2 preferably being alkyl,
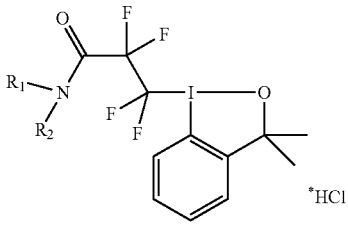
with R1 and R2 being unequal H, R1 and R2 preferably being alkyl,
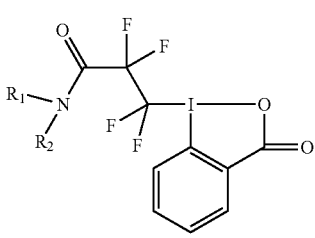
with R1 and R2 being unequal H, R1 and R2 preferably being alkyl,
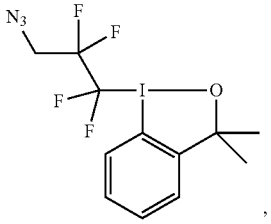
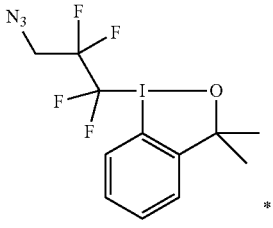
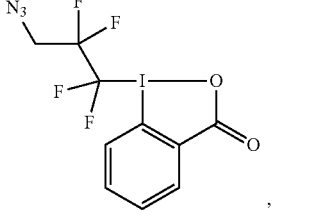
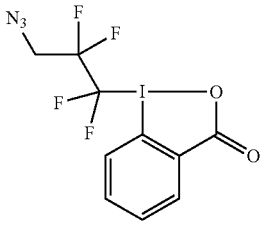

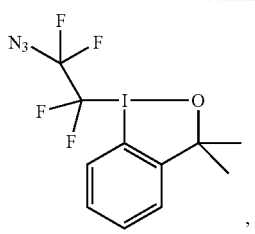
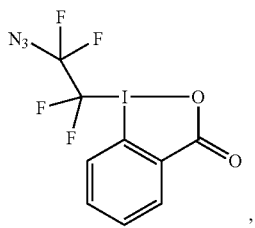
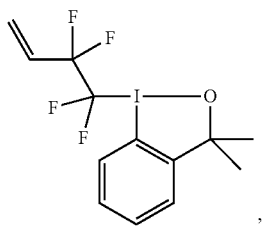
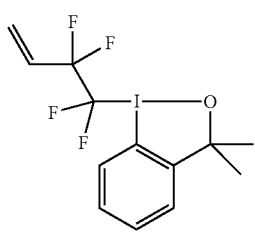
*HCl,
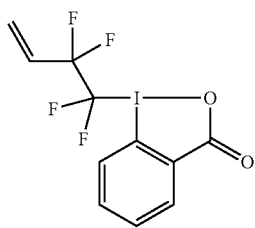
In some embodiments, the compound is selected from
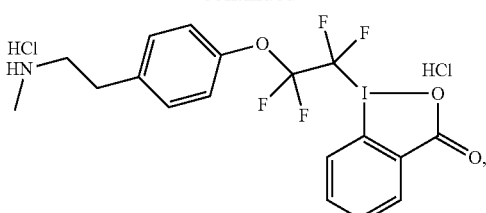
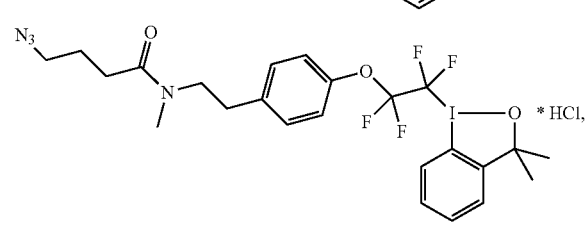
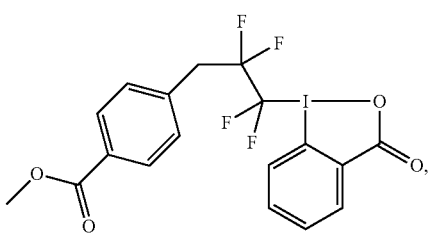
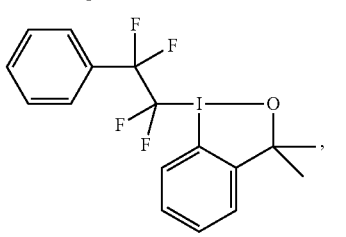
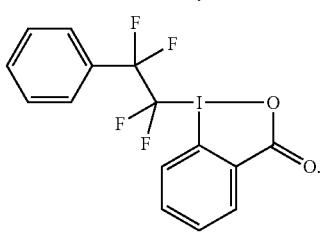
In some embodiments, the compound of formula II is selected from
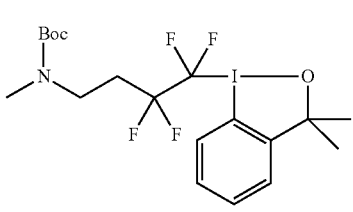
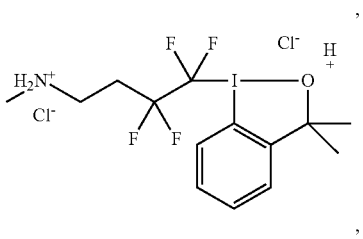

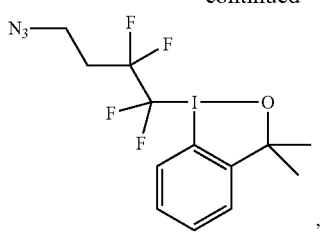
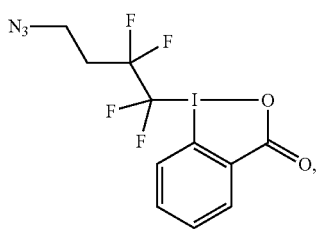
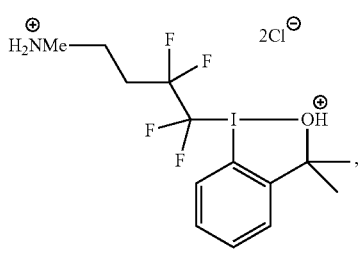
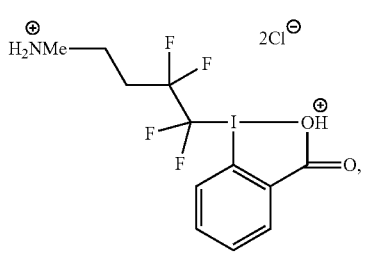
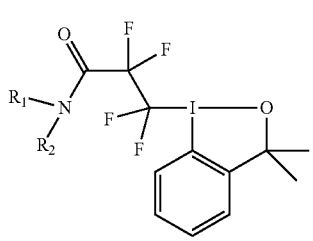
with R1 and R2 being unequal H, R1 and R2 preferably being alkyl,
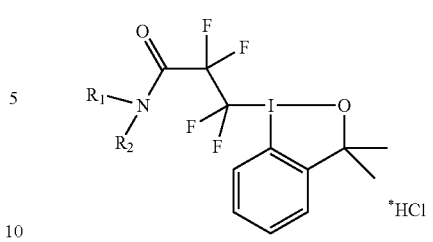
with R1 and R2 being unequal H, R1 and R2 preferably being alkyl,
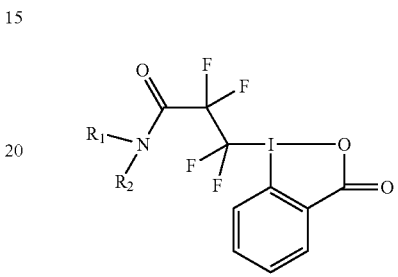
with R1 and R2 being unequal H, R1 and R2 preferably being alkyl,
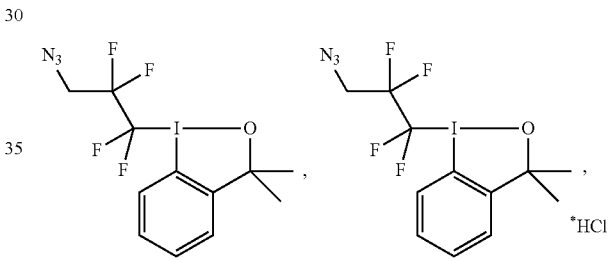
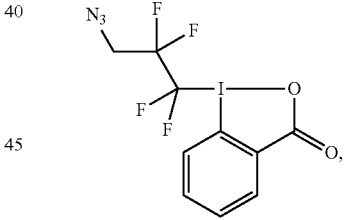
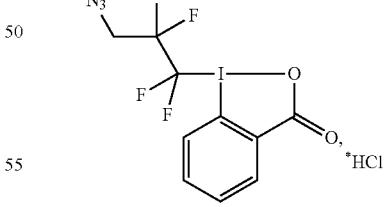
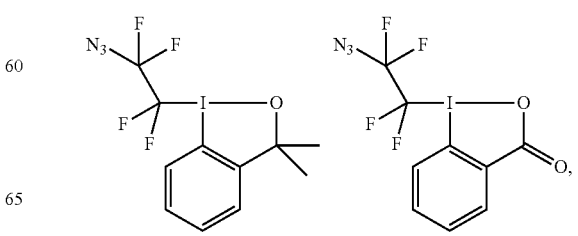

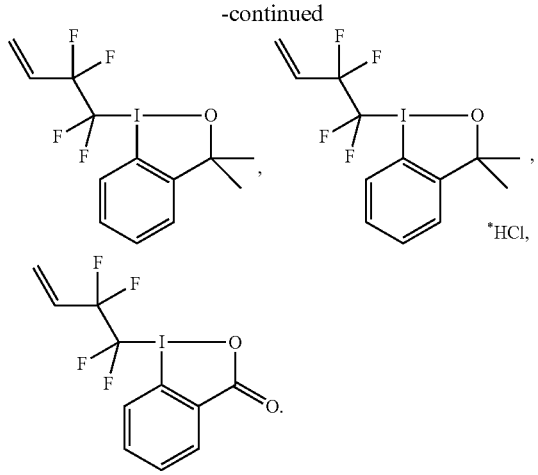

DETAILED DESCRIPTION AND EXAMPLES

Example 1. Synthesis of Reagent 7-Salt

The synthesis of reagent 7-salt is described in Scheme 1. The phenolic oxygen of Boc-protected NMT (N-methyltyramine) was deprotonated with NaH and treated with $BrCF_2CF_2Br$ (Halon 2402) giving the bromide 4, which was converted to corresponding fluoroalkylsilane 5. An Umpolung reaction of 5 with fluoroiodane 6 provided the protected fluoroalkylation reagent 7-Boc as a brown oil, which was found to be stable for at least for six months at −20° C. Eventually, 7-Boc was deprotected using excess trifluoroacetic acid and subsequent precipitation with diethyl ether afforded crystalline bis-trifluoroacetate salt (7-salt), which appeared stable even at room temperature . . .[1] Even though the deprotected reagent (7) could be isolated and characterized, it decomposed rapidly even when stored in a freezer. For that reason, it was generated in situ from 7-salt by addition of base in all subsequent syntheses.

Scheme 1 Synthesis of reagent 7-salt.

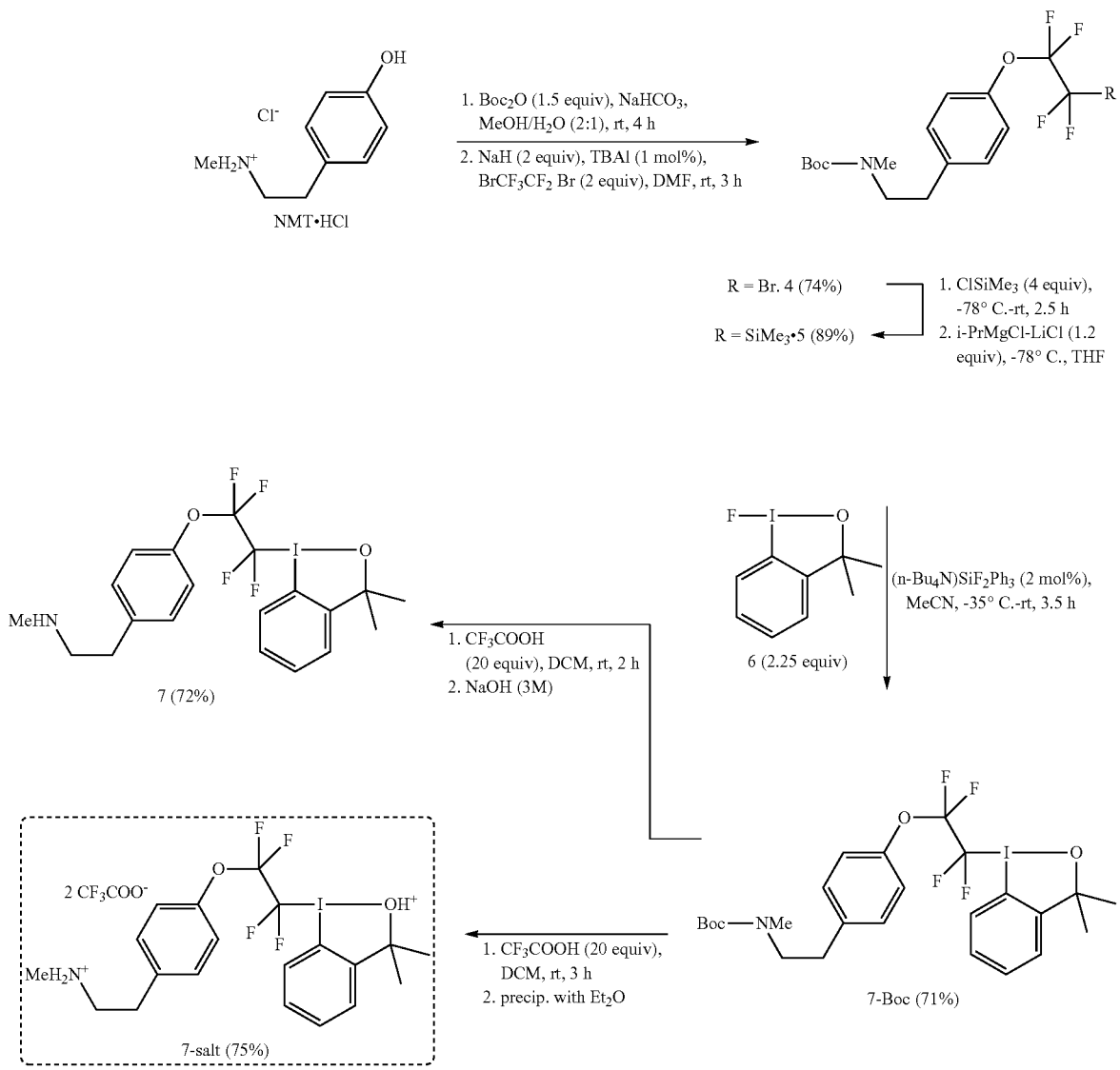

In the present invention, 7 was derivatized via peptide coupling to form the corresponding amide reagents 8. 1-Pyrenecarboxylic acid was selected for optimization of the reaction conditions as an easy-to-handle fluorophore. Aiming for mild reaction conditions, the inventors started the investigations with the 1-ethyl-3-(3-dimethylaminopropyl) carbodiimide hydrochloride (EDC) coupling reagent. In an initial trial, product 8a was first obtained in 26% isolated yield, which was increased to 63% by further optimization. Addition of the activator 1-hydbroxybenzotriazole (HOBt) usually caused decomposition of the reagent. Along these lines, structurally related (1-[bis(dimethylamino)methylene]-1H-1,2,3-triazolo[4,5-b]pyridinium 3-oxid hexafluorophosphate) (HATU) likewise induced reagent decomposition. Interestingly, acyl chloride (generated with oxalyl chloride and cat. DMF) afforded 8a in 78% yield at the first attempt and 89% under optimized conditions.

Example 2. Synthesis of Reagent 8-a-q

In the present invention freshly generated acyl chlorides is employed, with only slight modifications such as using Hünig's base instead of triethylamine in some cases, reagents 8b-q were synthesized mostly in good to excellent yields (Scheme 2). The eight examples of benzoic acid derivatives (8b-i) revealed a remarkable scope of functional groups that can be used for further functionalization via coupling, cycloaddition, substitution, etc. Aside from two simple fluorophores (reagents based on coumarin 8j and fluorescein 8k), the rest of the scope comprises aliphatic carboxylic acids. The coupling of (1S)-(−)-camphanic acid (in 8l) implies the possibility of introducing a chiral building block, while reagent 8m is a viable candidate for thiol-selective biotinylations. Finally, the inventors synthesized reagents containing the tetra(ethylene glycol) chain that promotes water solubility—these reagents featured groups suitable for click reactions (8n, 8o) and two examples of pyrene as a fluorophore (8p, 8q).

Scheme 2: Synthesis of reagents 8a-q.

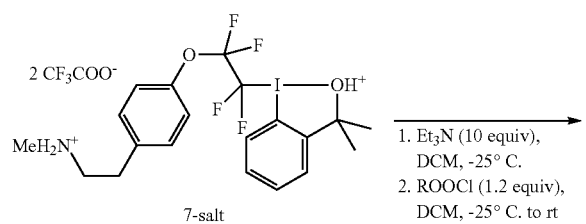

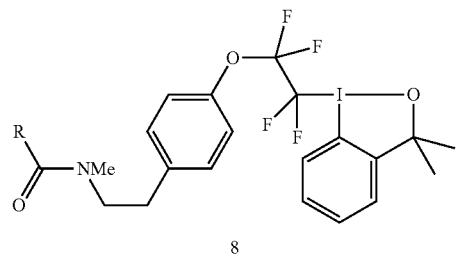

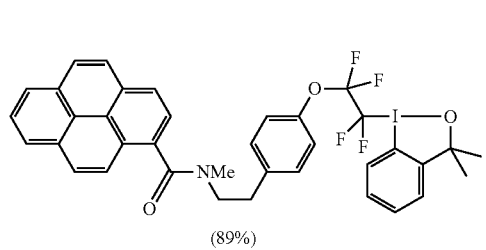

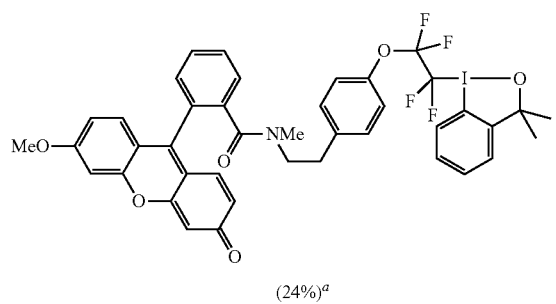

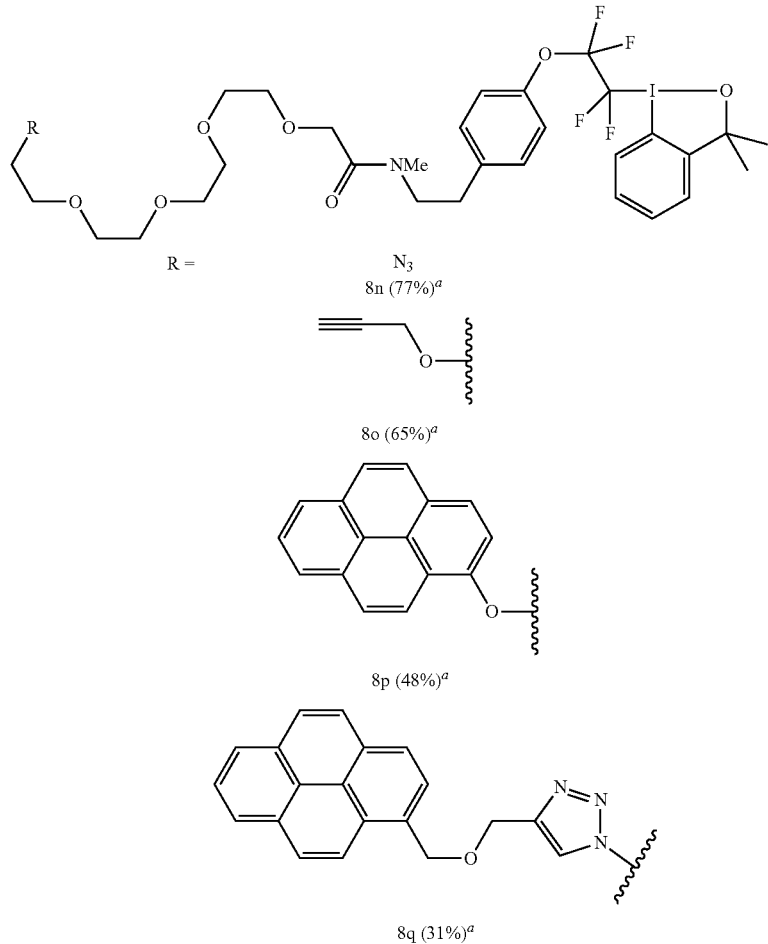
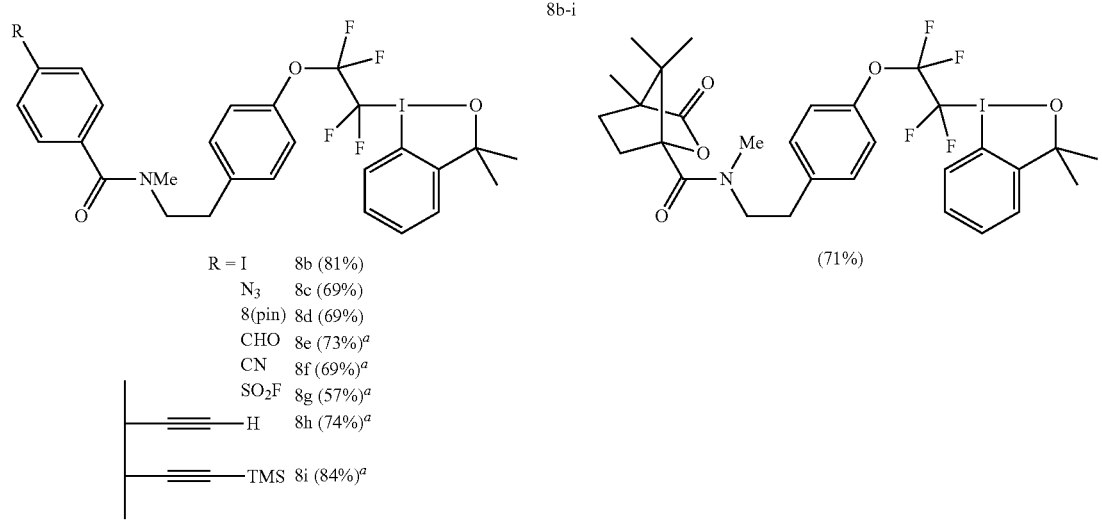

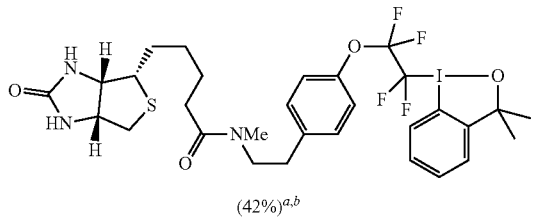

(42%)[a,b]

[a] (i-Pr)₂EtN was used as the base instead of Et₃N
[b] DMF was used as the solvent instead of DCM

Example 3. Synthesis of Reagent 9-a-c

The inventors further envisioned that the amine functionality present in 7 could be used for the preparation of sufonamide reagents 9 (Scheme 3). Indeed, three examples were synthesized, comprising 4-nitrophenyl (9a), dansyl (9b), and the highly fluorescent dye Lissamine™ Rhodamine B (9c).

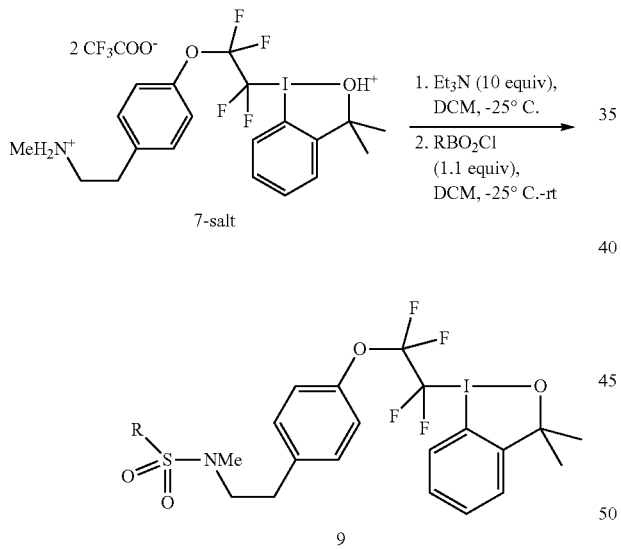

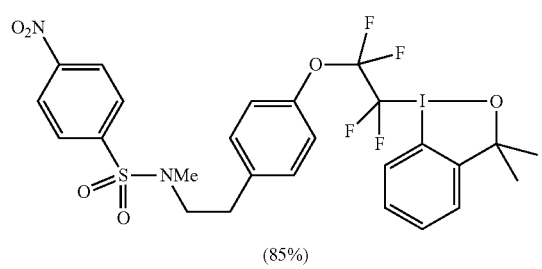

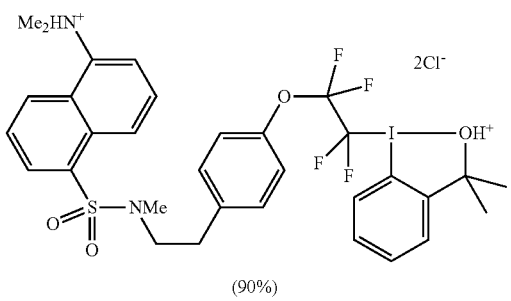

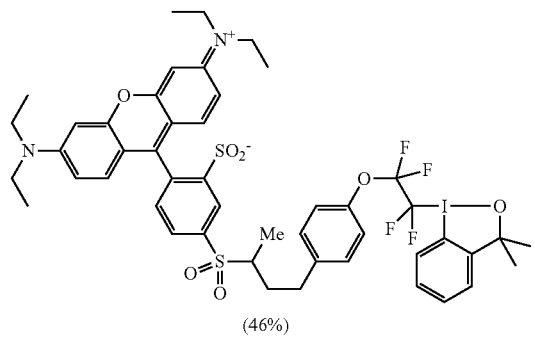

Example 4. Synthesis of Reagent 10

The synthesis of a reagent bearing a tertiary amine group was motivated by an expected increase in water solubility upon its protonation. To this end, a reaction of 7-salt with commercially available 6-(2-iodoacetamido)fluorescein was attempted. However, the iodide liberated by the $S_N^2$ reaction reduced the hypervalent iodine species and the desired product could not be isolated. This issue was resolved by starting from analogous 6-(2-bromoacetamido)fluorescein, which was coupled with 7-salt to give reagent 10a in 39% yield (Scheme 4). In a similar fashion, propargyl-functionalized amine reagent 10b was prepared in 56% yield.

Scheme 4 Synthesis of reagent 10.

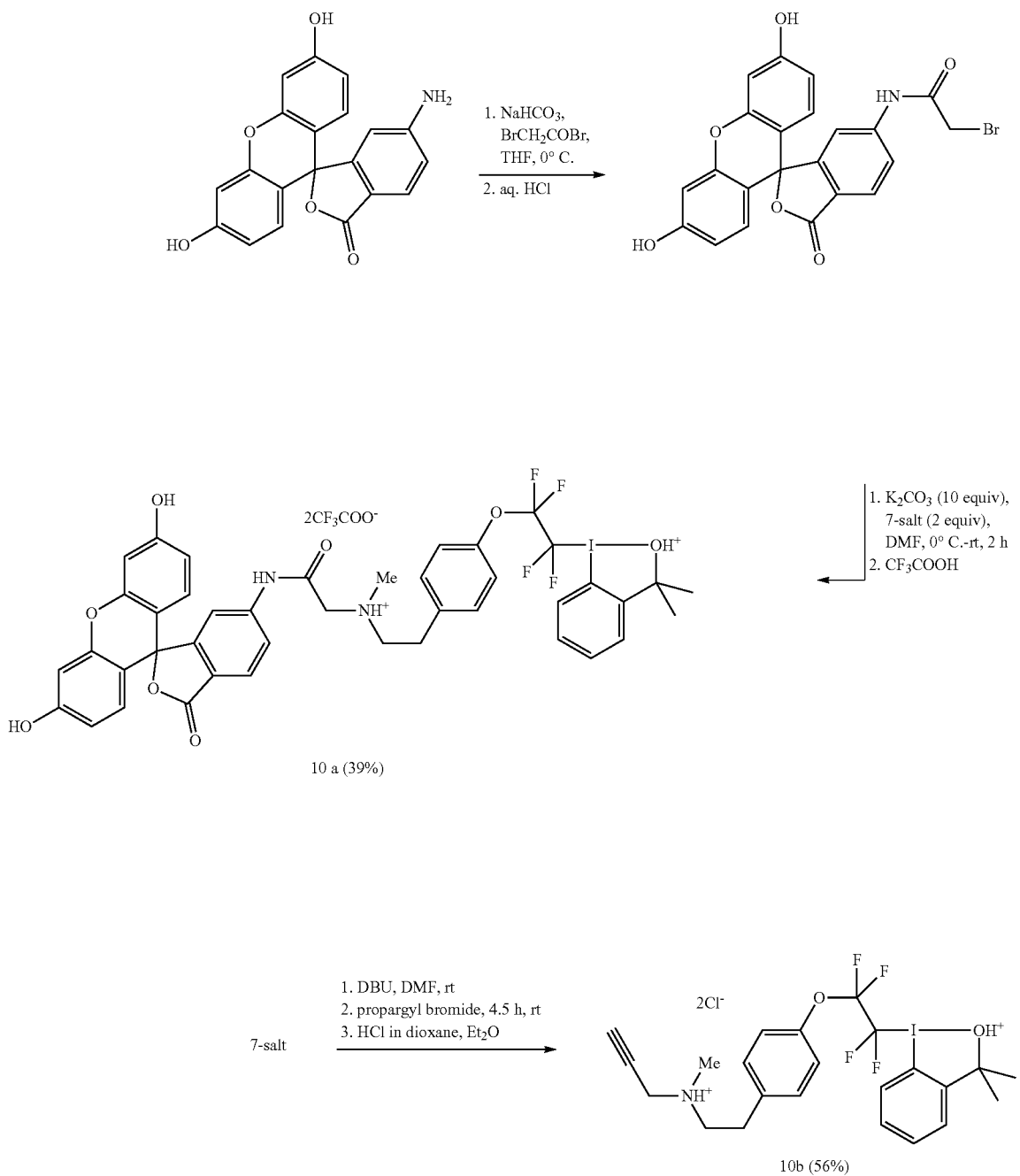

Example 5. Application of Hypervalent Iodine(III)-R$_f$ Reagents 1 and 2 in the Formation of a Quaternary Carbon Center All entries described in examples 5 to 9 refer to entries described in table 2.

The inventors envisaged that the conversion of substrates to the corresponding ketene silyl amides (KSAs) might be beneficial to control the reactivity of these species towards hypervalent iodine-CF$_3$ reagents. Hence, the inventors report herein a mild, operationally simple and highly efficient method for the a-trifluoromethylation and a perfluoroalkylation of lactamderived KSAs by the use of reagents 1 and 2a in the presence of catalytic amounts of TMSNTf2 (1 mol %) or even under catalyst free conditions. Additionally, the inventors describe a direct one-pot protocol enabling these transformations without the isolation of intermediate KSAs.

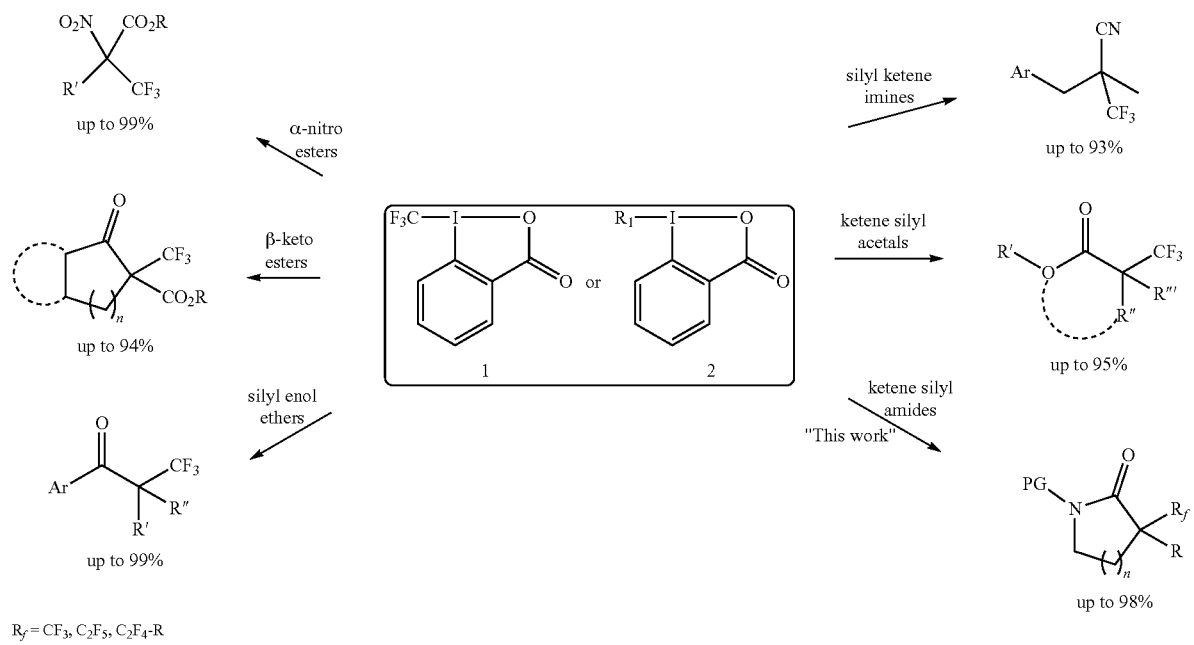

Scheme 5 Application of hypervalent iodine(III)-Rf reagents 1 and 2 in the formation of a quaternary carbon center.

Example 6: α-Trifluoromethylation of KSAs and Direct, One-Pot a-Trifluoromethylation of Carbonyl Compounds: Lactam Scope.—Trifluoromethylation of KSAs and Direct, One-Pot a-Trifluoromethylation of Carbonyl Compounds: Lactam Scope To probe the viability of this transformation, the inventors investigated the reaction between KSA 4a and reagents 1 and 2a under various conditions (Table 2). It turned out that the direct trifluoromethylation of 4a using either 1 or 2a in $CH_2Cl_2$ at low temperature (78 1C) gave after 19 h the corresponding product 8a in only moderate yields, whereby reagent 2a exhibited a slightly better reactivity (entries 1 and 2). Based on the experience with the activation of reagents 1 and 2a, various Lewis acids such as triflimides and metal complexes were tested as catalysts (entries 3-7 and 10-13). Among them, trimethylsilyl triflimide displayed excellent catalytic properties, leading to the desired product in 96% $^{19}F$ NMR yield (entry 6). Notably, 1 mol % of Mn and V catalysts with salen-type ligands also efficiently catalysed the reaction (entries 12 and 13). Surprisingly, however, catalyst loadings higher than 1 mol % significantly lowered product yields (entries 8 and 9).

Having found an effective catalyst system for the trifluoromethylation of KSAs, the inventors next examined the reaction scope with various substituted KSAs, which were prepared by lithiation of the corresponding lactams followed by trapping with TMSCl. It is important to highlight that their synthesis was straightforward, as the isolated crude compounds were pure by elemental analysis and were directly used in the next trifluoromethylation step (ESI†).

As summarized in Scheme 6, a broad range of KSAs exhibiting diverse steric and electronic properties readily participate in this transformation. First experiments showed that lactamderived KSAs undergo trifluoromethylation with reagent 2a even without the $TMSNTf_2$ catalyst giving the corresponding α-trifluoromethylated products in moderate to good yields (8a,8e, 8f, 8g). the inventors believe that the level of efficiency observed under catalyst-free conditions is the result of both low steric requirements of the substrates and their high electron density. The addition of 1 mol % of the catalyst ($TMSNTf_2$) considerably improved the reactivity as shown in Scheme 6. The reaction tolerates different N-protecting groups, albeit benzyl (Bn), benzyloxymethyl (BOM), and tert-butyloxycarbonyl (Boc) derivatives formed the corresponding products in lower yields relative to N-Me derivatives (8b-d). The ring size of KSAs had minimal impact on the yield of the corresponding products (8f-g). KSAs derived from γ-lactam with a variety of α-substituents such as benzyl (4a), phenyl (4e), methoxyethyl (4h) and trimethysilyl (4j) featured excellent reactivity delivering the corresponding products in high yields. Functional α-substituents such as allyl (4i) and 3-TMS-propargyl (4k) are fully compatible with this method as well. Notably, KSA 4l derived from substituted 3,4-dihydroquinolin-2-one was successfully trifluromethylated forming product 8l in 87% isolated yield. The latter substructure is present in many nitrogen heterocyclic compounds with a potential activity as plant disease control agents.

The inventors further optimised the synthetic applicability of this method and devised a one-pot, two-step protocol for the direct a-trifluoromethylation of lactams (Scheme 6). Thus, the chosen KSA is first formed in situ, followed by the addition of reagent and catalyst to affect the targeted a-trifluoromethylation. This simple and straightforward procedure is applicable to various a-substituted lactams as shown in Scheme 6, affording the desired products with high overall efficiency. Interestingly, in the case of a-propargyl substituted NMP (3k) silylation of the terminal alkyne takes place in addition to a-trifluorormethylation.

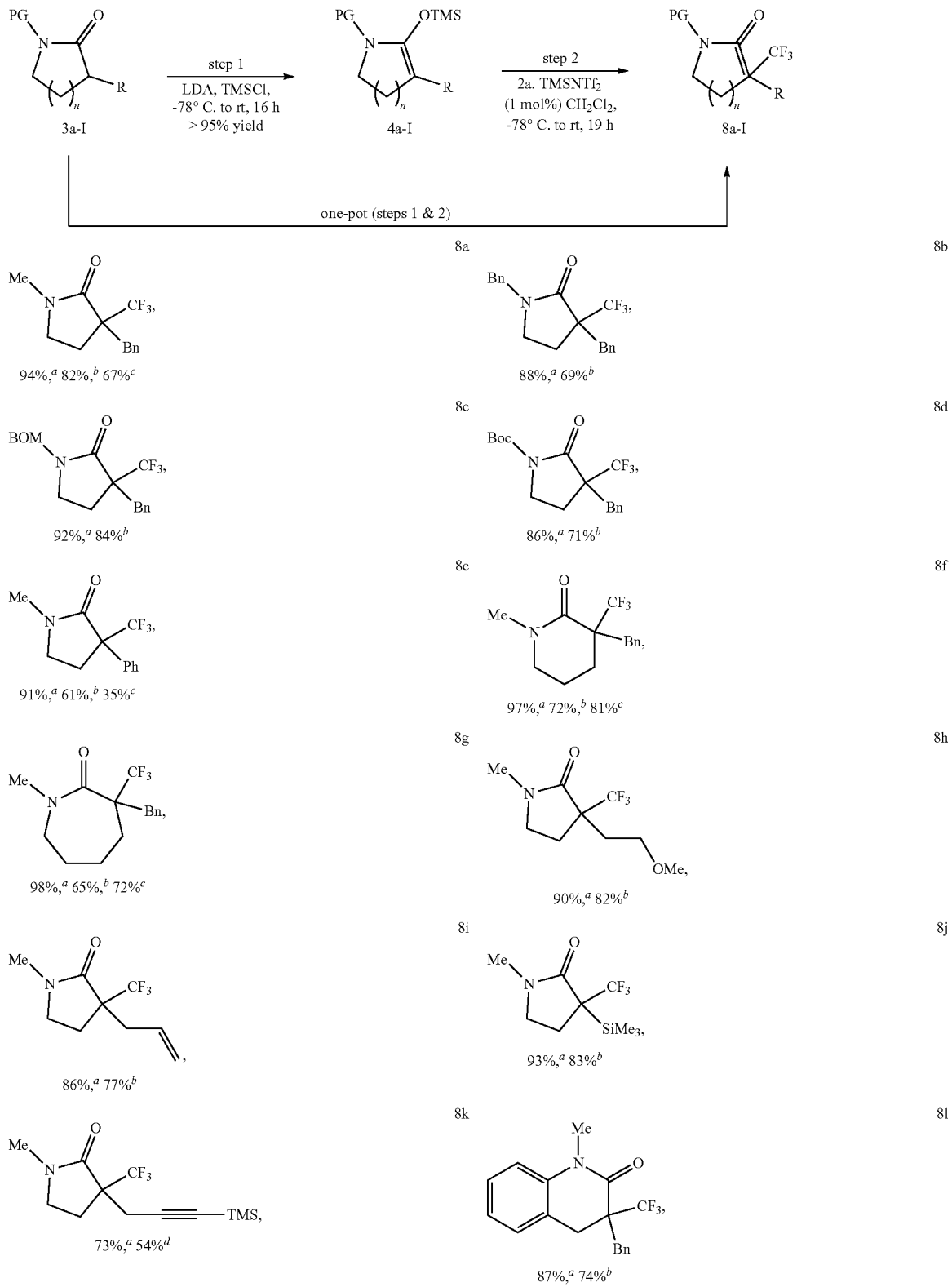

Scheme 6 α - Trifluoromethylation of KSAs and direct, one-pot α-trifluoromethylation of carbonyl compounds: lactam scope.

Reaction conditions: [a] 4a-I (1.3 mmol, 1.3M in DCM), 2a (1.0 mmol), TMSNTf$_2$ (1 mol%), -78° C. to rt, 19 h. [b] One-pot procedure: LDA (1.4 mmol), 3a-I (1.3 mmol), TMSCl (2.2 mmol), THF, -78° C. to rt, 19 h; 2a (1.0 mmol), TMSNTf$_2$ (1 mol%), _78 1C to rt, 19 h. c In the absence of TMSNTf2. [d] One-pot procedure: LDA (2.8 mmol), 3k (1.3 mmol), TMSCl (4.4 mmol), THF, -78° C. to rt, 19 h; 2a (1.0 mmol), TMSNTf2 (1mol%), -78° C. to rt, 19 h.

Example 7: α-Perfluoroalkylation of KSA

The inventors recently developed a series of new hypervalent iodine(III)-Rf reagents based on the 1,3-dihydro-3,3-dimethyl-1,2-benziodoxole scaffold, able to transfer a functionalised tetrafluoroethyl unit. These reagents demonstrated very similar reactivity in a number of transformations compared to their established $CF_3$ analogues 1 and 2a providing access to tetrafluoroethylated compounds. We therefore examined the applicability of previously developed (2b-d, 2f, 2h) and newly synthesised (2e, 2g, 2i-k) fluoroalkyl hypervalent iodine(III)-Rf reagents in the a-perfluoroalkylation of lactams. KSA 4a was chosen as a model substrate for these transformations, and the results are summarized in Scheme 7. The inventors were thus pleased to find that all tested reagents displayed excellent levels of reactivity towards KSA 4a giving the corresponding a fluoroalkylated products in moderate to high yields. The obtained products contain tetrafluoroethyl moieties bearing S-Ar (9ab), O-Ar (9ac-af), CH2-Ar (9ag), and N-heterocyclic (9ah) substituents and can be used for further functionalizations. Products 9ai and 9aj are particularly interesting due to the presence of a fluorescent moiety based on coumarin, which can serve for the labelling of biological targets.

Example 8: ORTEP View of the X-Ray Structure of α-Perfluoroethyl Lactam

Crystalline α-perfluoroethyl lactam 9ak was obtained in high (95%) yield from reagent 2k and was characterised by X-ray analysis (FIG. 1). X-ray crystal structures of acyclic and cyclic all-carbon-substituted α-perfluoroethyl carbonyl compounds have not been reported previously, as confirmed by a CCDC database search. In the solid state compound 9ak displays values of bond lengths and angles in the expected ranges.

Example 9: Synthesis of (Perfluoroethyl)Pyrrolidine 10 Via One-Pot, Multistep Transformation of Lactam 3a As shown in scheme 7, lactam 3a was successfully transformed to the corresponding 3-perfluoroethyl-substituted pyrrolidine 10 in overall 71% isolated yield via a straightforward three-step protocol including in situ silylation, a fluoroalkylation and reduction steps.

Scheme 7: Synthesis of (perfluoroethyl)pyrrolidine 10 via one-pot, multistep transformation of lactam 3a.

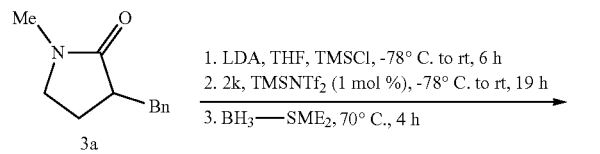

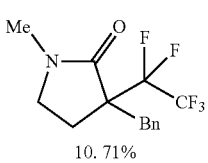

10. 71%

TABLE 2

Optimization reaction conditions for the catalytic trifluoro-methylation of KSA

| Entry[a] | Reagent | catalyst | mol % | Yield[b] (%) |
|---|---|---|---|---|
| 1 | 1 | — | — | 42 |
| 2 | 2a | — | — | 67 |
| 3 | 2a | $Zn(NTf_2)_2$ | 1 | 79 |
| 4 | 2a | $LiNTf_2$ | 1 | 68 |
| 5 | 2a | $AgNTf_2$ | 1 | 62 |
| 6 | 2a | $CuNTf_2$ | 1 | 71 |
| 7 | 2a | $TMSNTf_2$ | 1 | 96(94)[c] |
| 8 | 2a | $TMSNTf_2$ | 2.5 | 86 |
| 9 | 2a | $TMSNTf_2$ | 3 | 83 |
| 10 | 2a | $[V(acac)_2O]$ | 1 | 74 |
| 11 | 2a | 5 | 1 | 74 |
| 12 | 2a | 6 | 1 | 91 |
| 13 | 2a | 7 | 1 | 93 |

[a]Reaction conditions: 4a (0.3 mmol, 0.5M in $CH_2Cl_2$), 1 or 2a (0.23 mmol), catalyst (1-3 mol %), Ar atmosphere, 19 h.
[b]Yields were determined by $^{19}F$ NMR using benzotrifluoride as in internal standard.
[c]Isolated yield.

Example 10

General Information

Reactions with air-sensitive materials were carried out under an argon atmosphere using standard Schlenk techniques. All solvents were dried by activated molecular sieves (3 Å) and stored under argon. All commercially available chemicals were used as received unless stated otherwise. Flash column chromatography was performed using silica gel 60 (0.040-0.063 mm) supplied by Sigma-Aldrich. Automated flash column chromatography was performed on Teledyne ISCO CombiFlash Rf+ Lumen Automated Flash Chromatography System with UV/Vis and ELS detection using standard manufacturer's RediSep Rf columns. Unless stated otherwise, the TLC analyses were done using TLC silica gel 60 F254 aluminium sheets from Merck, which were visualized under UV (254/366 nm) or using the KMnO$_4$ stain solution.

The melting points are uncorrected. $^1$H, $^{13}$C and $^{19}$F NMR spectra were measured on Bruker spectrometers ($^1$H carrier frequency of 200, 300, 400 and 500 MHz) at ambient temperature using 5 mm diameter NMR tubes. The chemical shift values (δ) are reported in ppm relative to residual solvents[ii] (for $^1$H and $^{13}$C spectra) and internal or external CFCl$_3$ (δ=0 ppm for $^{19}$F NMR). Coupling constants (J) are reported in Hertz. Multiplicity is described by abbreviations (d=doublet, t=triplet, dd=doublet of doublets, dm=doublet of multiplets, bs=broad singlet, bt=broad triplet, bm=broad multiplet, etc.). Structural elucidation was aided by additional acquisition of $^{13}$C APT and/or various 2D spectra ($^1$H-$^1$H COSY, $^1$H-$^{13}$C HSQC, $^1$H-$^{13}$C HMBC, and $^{19}$F-$^{13}$C HMBC). High resolution MS spectra (HRMS) were recorded on an LTQ Orbitrap XL or Bruker maXis using electrospray ionization (ESI), Waters Micromass AutoSpec Ultima using electron impact (EI) ionization, Agilent 7890A GC coupled with Waters GCT Premier orthogonal acceleration time-of-flight detector using chemical ionization (CI), and on a Bruker solariX 94 ESI/MALDI-FT-ICR using dual ESI/MALDI ionization.

Screening Peptide Coupling Conditions

TABLE S1

Optimization of peptide coupling between 7-salt and 1-pyrenecarboxylic acid

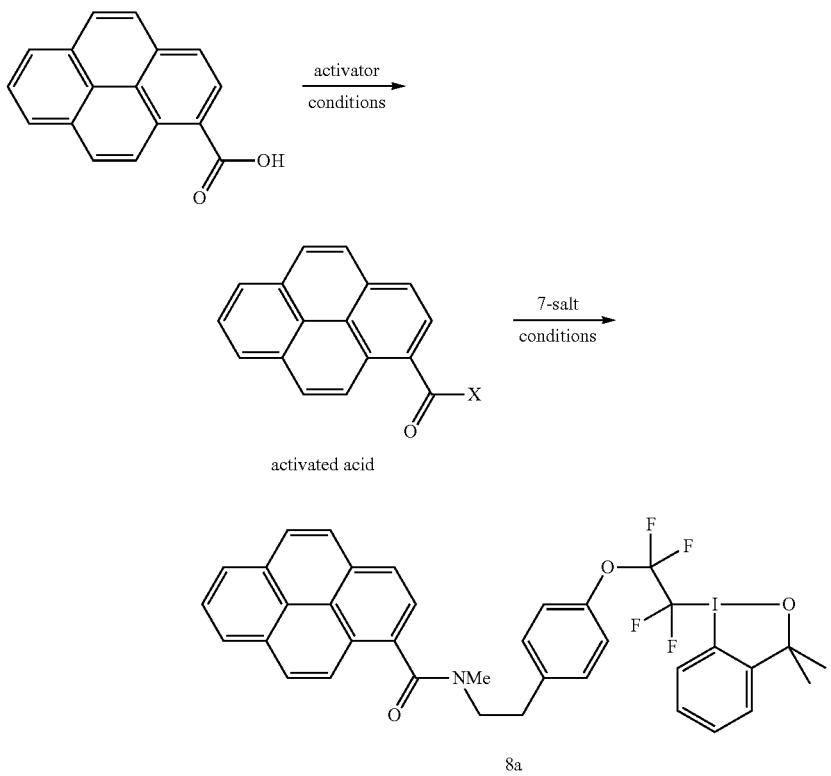

| Entry | Acid equiv | Activator (equiv) | Base (equiv) | Solvent | Time activation + coupling (h) | Temperature | Yield[a] (%) |
|---|---|---|---|---|---|---|---|
| 1[b] | 1.0 | EDC (1.1) | Et$_3$N (1.1) | DCM | 0.1 + 3 | rt | 26 |
| 2 | 1.2 | EDC (1.4) | Et$_3$N (4) | DCM | 0.5 + 4 | 0° C. to rt | 63 |
| 3 | 1.2 | EDC (1.4) + HOBt (1.4) | Et$_3$N (4) | DCM | 1 + 2.5 | rt | 16 |
| 4[b] | 1.0 | HATU (1.5) | (i-Pr)$_2$EtN (2.5) | DCM | 0.25 + 2.5 | rt | 0 |
| 5 | 1.2 | (COCl)$_2$ (1.5) + DMF (1.2) | Et$_3$N (10) | DCM | 3 + 0.25 | rt | 78 |
| 6 | 1.2 | (COCl)$_2$ (1.5) + DMF (1.2) | Et$_3$N (10) | DCM | 3 + 2 | −25° C. to rt | 89 |

[a]Isolated yield.
[b]Freshly prepared 7 was used instead of 7-salt.

Synthesis and Characterization of Compounds

Reagent # NMT and its Precursors tert-Butyl (4-hydroxyphenethyl)(methyl)carbamate (#)JV083-4 [CAS 112196-70-0]

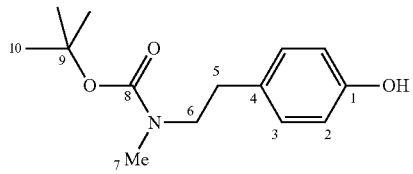

N-Methyltyramine hydrochloride (18.8 g, 100 mmol) was dissolved in a MeOH:H$_2$O (2:1) mixture (350 mL). NaHCO$_3$ (25.2 g, 300 mmol) and Boc$_2$O (32.7 g, 150 mmol) were added, and the mixture was stirred for 4 h at rt. MeOH was removed under reduced pressure, the mixture was extracted with EtOAc (3×200 mL) and the organic extracts were washed with 10% aqueous HCl (1×200 mL), water (1×50 mL) and brine (1×50 mL), dried with Na$_2$SO$_4$, filtered, and concentrated under vacuum. The product was obtained as a dense brown oil of ca. 90% purity, which was used further without purification. Optionally, the compound could be purified by automated flash chromatography (gradient elution from hexane to EtOAc/hexane 1:1), yielding the product as colourless oil that crystallized as a white solid.

Yield: 27.8 g at 90% purity (99%); R$_f$=0.25 (EtOAc: hexane 1:4); m.p. 76-79° C.

$^1$H NMR (300.13 MHz, CDCl$_3$): δ 1.40 (bs, 9H, C(10)H$_3$), 2.73 (t, $^3J_{HH}$=7.2, 2H, C(5)H$_2$), 2.80 (s, 3H, C(7)H$_3$), 3.39 (t, $^3J_{HH}$=7.2, 2H, C(6)H$_2$), 5.61 (bs, 1H, OH), 6.76 (d, $^3J_{HH}$=8.0, 2H, C(2)H), 7.03 (d, $^3J_{HH}$=8.0, 2H, C(3)H);

$^{13}$C {$^1$H} NMR (125.80 MHz, CDCl$_3$): δ 28.3 and 28.4 (s, C(10)H$_3$), 33.1 and 33.5 (s, C(5)H$_2$), and 34.7 (s, C(7)H$_3$), 50.7 and 51.0 (s, C(6)H$_2$), 79.8 (s, C(9)), 115.4 (s, C(2)H), 129.7 (s, C(3)H), 130.1 (s, C(4)), 154.9 and 155.1 (s, C(1)), 156.0 (s, C(8)).

HRMS (m/z, ESI$^+$): [M+Na]$^+$ calcd. for C$_{14}$H$_{21}$NNaO$_3$, 274.1414; found, 274.1411.

tert-Butyl (4-(2-bromo-1,1,2,2-tetrafluoroethoxy) phenethyl)(methyl)carbamate (#) JV085-6

NaH (60% in mineral oil; 4.0 g, 0.1 mol) was washed with dry pentane (2×20 mL) in an oven-dried three-necked flask. Anhydrous DMF (50 mL) was added, followed by a

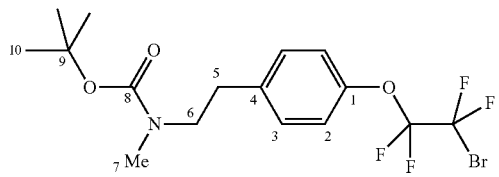 [SMILES: CN(CCc1ccc(OC(F)(F)C(F)(F)Br)cc1)C(=O)OC(C)(C)C]

portionwise addition of a solution of BocNMT (14.0 g, 50.0 mmol, 90% purity) in DMF (60 mL) at 0° C. The mixture was stirred for 1 h 15 min. Tert-butylammonium iodide (185 mg, 0.50 mmol) was added, followed by a portionwise addition of BrCF$_2$CF$_2$Br (11.9 mL, 100 mmol), and the reaction mixture was stirred for 3 h at rt. The mixture was diluted with water (300 mL) and extracted with 1:1 ether/pentane mixture (3×150 mL). The combined organic layers were washed with water (3×100 mL) and brine (3×100 mL), dried over Na$_2$SO$_4$, and concentrated to give the product as an orange-yellow liquid of ca. 85% purity, which was used further without purification. Optionally, the compound could be purified by automated flash chromatography (gradient elution from hexane to EtOAc/hexane 1:1), yielding the product as a yellow liquid.

Yield: 18.6 g at 85% purity (74%); R$_f$=0.60 (EtOAc: hexane 1:4);

$^1$H NMR (500.26 MHz, CDCl$_3$): δ 1.36 and 1.42 (bs, 9H, C(10)H$_3$), 2.79 (bs, 2H, C(5)H$_2$), 2.83 (s, 3H, C(7)H$_3$), 3.42 (bs, 2H, C(6)H$_2$), 7.13 (d, $^3J_{HH}$=8.4, 2H, C(2)H), 7.19 (bs, 2H, C(3)H);

$^{19}$F NMR (282.38 MHz, CDCl$_3$): δ−86.4 (bs, 2F, CF$_2$), −68.4 (t, $^3J_{FF}$=4.9, 2F, CF$_2$);

$^{13}$C {$^1$H} NMR (125.80 MHz, CDCl$_3$): δ 28.3 (s, C(10)H$_3$), 33.4 and 33.8 (s, C(5)H$_2$), 34.2 and 34.7 (s, C(7)H$_3$), 50.1 and 50.5 (s, C(6)H$_2$), 79.3 (s, C(9)), 113.6 (tt, $^1J_{CF}$=312, $^2J_{CF}$=44.9, CF$_2$), 115.8 (tt, $^1J_{CF}$=275, $^2J_{CF}$=31.9, CF$_2$), 121.6 (bm, C(2)H), 130.1 (s, C(3)H), 138.1 (s, C(4)), 147.2 (bm, C(1)), 155.5 (s, C(8));

HRMS (m/z, ESI$^+$): [M+Na]$^+$ calcd. for C$_{16}$H$_{20}$BrF$_4$NNaO$_3$, 452.0455, found, 452.0458.

tert-Butyl methyl(4-(1,1,2,2-tetrafluoro-2-(trimethylsilyl)ethoxy)phenethyl)carbamate (#) JV086-6

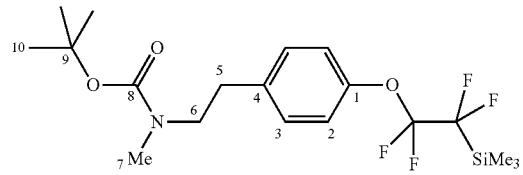 [SMILES: CN(CCc1ccc(OC(F)(F)C(F)(F)[Si](C)(C)C)cc1)C(=O)OC(C)(C)C]

Bromide # (18.5 g, 36.6 mmol, 85% purity) was dissolved in anhydrous THF (150 mL) at −65° C. TMSCl (18.6 mL, 146 mmol) was added, followed by a portionwise addition of i-PrMgCl.LiCl (1.3 M solution in THF, 33.8 mL, 43.9 mmol) within 15 min, and the reaction mixture was stirred for 3 h at −65° C. to rt. The mixture was concentrated, water (200 mL) was added, and the product was extracted with an ether/hexane 1:1 mixture (3×150 mL). The combined organic layers were washed with water (2×100 mL) and brine (2×100 mL), dried over Na$_2$SO$_4$, and concentrated to give the product as an orange-brown oil consisting of the target compound and the protodesilylated RCF$_2$CF$_2$H compound in a ratio of 89:11. The product of of ca. 80% purity was used further without purification. Optionally, the compound could be purified by automated flash chromatography (gradient elution from hexane to EtOAc/hexane 1:1), yielding the pure product as a yellow liquid that solidified.

Yield: 17.3 g at 80% purity (89%); R$_f$=0.40 (EtOAc: hexane 1:4); m.p. 32-33° C.;

$^1$H NMR (200.13 MHz, CDCl$_3$): δ0.30 (bs, 9H, Si(CH$_3$)$_3$), 1.37 (bs, 9H, C(10)H$_3$), 2.81 (bs, 5H, C(5)H$_2$ and C(7)H$_3$), 3.41 (t, $^3J_{HH}$=7.1, 2H, C(6)H$_2$), 7.10 (d, $^3J_{HH}$=8.7, 2H, C(2)H), 7.16 (bs, 2H, C(3)H);

$^{19}$F NMR (188.29 MHz, CDCl$_3$): δ−130.7 (t, $^3J_{FF}$=4.8, 2F, CF$_2$), −85.5 (t, $^3J_{FF}$=4.8, 2F, CF$_2$);

$^{13}$C {$^1$H} NMR (50.33 MHz, CDCl$_3$): δ−4.40 (tt, $^3J_{CF}$=2.3, $^4J_{CF}$=1.1, Si(CH$_3$)$_3$), 28.3 (s, C(10)H$_3$), 33.4 and 33.7 (s, C(5)H$_2$), 34.2 and 34.5 (s, C(7)H$_3$), 50.3 and 50.5 (s, C(6)H$_2$), 79.3 (s, C(9)), 119.1 (tt, $^1J_{CF}$=275, $^2J_{CF}$=27.8, CF$_2$), 120.5 (tt, $^1J_{CF}$=272, $^2J_{CF}$=38.2, CF$_2$), 121.5 (s, C(2)H), 129.9 (s, C(3)H), 137.2 (s, C(4)), 147.6 (t, $^3J_{CF}$=1.9, C(1)), 155.5 (s, C(8)); HRMS (m/z, ESI$^+$): [M+H]$^+$ calcd. for C$_{19}$H$_{30}$F$_4$NO$_3$Si, 424.1926, found, 424.1923.

tert-Butyl (4-(2-(3,3-dimethyl-1λ$^3$-benzo[d][1,2]iodaoxol-1 (3H)-yl)-1,1,2,2-tetrafluoroethoxy)phenethyl)-(methyl)carbamate (#) JV087-7

An oven-dried 3-necked round-bottom flask (1 L) equipped with an addition funnel (250 mL) and a massive magnetic stirring bar was charged with fluoroiodane (20.6 g, 73.6 mmol).

Anhydrous CH$_3$CN (250 mL) was added from a Schlenk via a PTFE cannula, and the solution was cooled down to −35° C. A solution of the silane (17.3 g, 32.7 mmol, 80% purity) in CH$_3$CN (250 mL) was transferred to the addition funnel via a cannula. TBAT (0.40 g, 0.74 mmol) was added to the fluoroiodane solution as solid, and the silane solution was added dropwise at −35° C. to −15° C. over a period of 30 min. The orange mixture was stirred at −20° C. to rt for 3 h. The solvent was evaporated, the crude product was redissolved in an EtOAc/hexane mixture and anchored on Celite (25 g). The title product was isolated by column chromatography (1 kg of silica gel, column 9×50 cm; gradient elution from hexane to EtOAc), yielding a brown oil.

Yield: 14.1 g (71%); R$_f$=0.29 (EtOAc:hexane 1:1);
$^1$H NMR (500.26 MHz, CDCl$_3$): δ1.34-1.45 (bs, 9H, C(18)H$_3$), 1.50 (s, 6H, C(2)H$_3$), 2.72-2.87 (bs, 5H, C(13)H$_2$ and C(15)H$_3$), 3.42 (bs, 2H, C(14)H$_2$), 7.12 (m, 2H, C(10)H or C(11)H), 7.14-7.24 (bs, 2H, C(10)H or C(11)H), 7.39 (m, 2H, C(4)H and C(6)H), 7.50 (m, 1H, C(5)H), 7.74 (m, 1H, C(7)H);
$^{19}$F NMR (470.67 MHz, CDCl$_3$): δ−97.5 (bs, 2F, CF$_2$), −84.8 (bs, 2F, CF$_2$);
$^{13}$C {$^1$H} NMR (125.80 MHz, CDCl$_3$): δ28.3 (s, C(18)H$_3$), 30.9 (s, C(2)H$_3$), 33.4 and 33.9 (s, C(13)H$_2$), 34.2 and 34.8 (s, C(15)H$_3$), 50.2 and 50.6 (s, C(14)H$_2$), 76.3 (s, C(1)), 79.4 (s, C(17)), 110.9 (m, C(8)), 111.5 (tt, $^1J_{CF}$=300, $^2J_{CF}$=38.1, CF$_2$), 117.2 (tt, $^1J_{CF}$=276, $^2J_{CF}$=26.0, CF$_2$), 121.7 (bs, C(10)H or C(11)H), 127.4 (s, C(4)H or C(6)H), 129.0 (tt, J$_{CF}$=5.3, 1.3, C(7)), 129.4 (s, C(4)H or C(6)H), 130.1 (s, C(10)H or C(11)H), 130.3 (s, C(5)H), 138.0 (s, C(12)), 147.2 (m, C(9)), 149.9 (s, C(3)), 155.5 (s, C(16)); HRMS (m/z, ESI$^+$): [M+H]$^+$ calcd. for C$_{25}$H$_{31}$F$_4$INO$_4$, 612.1228, found, 612.1228.

2-(4-(2-(3,3-Dimethyl-1λ$^3$-benzo[d][1,2]iodaoxol-1 (3H)-yl)-1,1,2,2-tetrafluoroethoxy)phenyl)-N-methylethan-1-amine (#) JV090-12

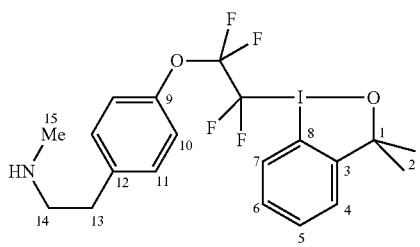 [SMILES: CNCCc1ccc(OC(F)(F)C(F)(F)I2OC(C)(C)c3ccccc32)cc1]

Reagent N-BocNMT (193 mg, 0.30 mmol) was dissolved in DCM (5 mL) in a round-bottom flask. Trifluoroacetic acid (0.46 mL, 6.00 mmol) was added. The mixture was stirred for 2 h at rt. DCM was evaporated, 10% aqueous HCl (10 mL) was added, and the organic impurities were extracted to pentane (3×13 mL). The acidic aqueous phase was cooled down to −0° C., alkalized with cold 3M aqueous NaOH (40 mL), and extracted with DCM (3×30 mL). The organic phase was washed with water (2×30 mL), brine (2×30 mL), dried over Na$_2$SO$_4$ and concentrated, yielding a yellow oil.

Yield: 110 mg (72%);
$^1$H NMR (500.13 MHz, CDCl$_3$): δ1.47 (s, 6H, C(2)H$_3$), 2.46 (bs, 3H, C(15)H$_3$), 2.86 (bs, 4H, C(13)H$_2$ and C(14)H$_2$), 3.69 (bs, 1H, NH), 7.10 (m, 2H, C(10)H), 7.20 (m, 2H, C(11)H), 7.36 (m, 2H, C(4)H and C(6)H), 7.46 (m, 1H, C(5)H), 7.71 (m, 1H, C(7)H);
$^{19}$F NMR (470.55 MHz, CDCl$_3$): δ−97.6 (bt, 2F, CF$_2$), −84.8 (bt, 2F, CF$_2$);
$^{13}$C {$^1$H} NMR (125.77 MHz, CDCl$_3$): δ 30.8 (s, C(2)H$_3$), 34.6 (s, C(13)H$_2$), 35.5 (s, C(15)H$_3$), 52.4 (s, C(14)H$_2$), 76.3 (s, C(1)), 110.9 (s, C(8)), 111.4 (tt, $^1J_{CF}$=337, $^2J_{CF}$=38.2, CF$_2$), 117.2 (tt, $^1J_{CF}$=277, $^2J_{CF}$=25.8, CF$_2$), 121.6 (s, C(10)H), 127.3 (s, C(4)H or C(6)H), 128.8 (t, J$_{CF}$=5.2, C(7)), 129.3 (s, C(4)H or C(6)H), 129.8 (s, C(11)H), 130.2 (s, C(5)H), 137.9 (bm, C(12)), 147.2 (m, C(9)), 149.8 (s, C(3)); HRMS (m/z, ESI$^+$): [M+H]$^+$ calcd. for C$_{20}$H$_{23}$F$_4$INO$_2$, 512.0704, found, 512.0691.

3,3-Dimethyl-1-(1,1,2,2-tetrafluoro-2-(4-(2-(methylammonio)ethyl)phenoxy)ethyl)-2,3-dihydro-1H-1λ$^3$-benzo[d][1,2]iodaoxol-2-ium bis(trifluoroacetate) (#) JV117-5

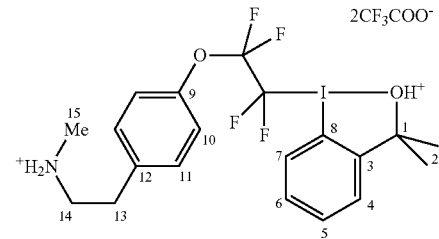 [SMILES: C[NH2+]CCc1ccc(OC(F)(F)C(F)(F)I2[OH+]C(C)(C)c3ccccc32)cc1]

Reagent N-BocNMT (4.38 g, 6.80 mmol) was dissolved in DCM (90 mL) in a round-bottom flask. Trifluoroacetic acid (10.4 mL, 136 mmol) was added. The mixture was stirred for 3 h at rt. DCM was evaporated giving yellow/orange oil. Diethyl ether was added slowly (70 mL in total), leading to the crystallization of a pale yellow solid. The solid was filtered off, washed with a small amount of ether and pentane, and dried in vacuum.

Yield: 3.75 g (75%); m.p. 88-90° C. (dec.); $^1$H NMR (300.13 MHz, CD$_2$Cl$_2$): δ1.68 (s, 6H, C(2)H$_3$), 2.68 (bs, 3H, C(15)H$_3$), 3.06 (bm, 2H, C(13)H$_2$), 3.17 (bm, 2H, C(14)H$_2$), 7.32 (m, 2H, C(11)H), 7.35 (m, 2H, C(10)H), 7.53 (m, 2H, C(4)H and C(6)H), 7.64 (m, 1H, C(5)H), 7.78 (m, 1H, C(7)H), 8.18 (bs, 1H, OH$^+$), 9.57 (bs, 2H, NH$_2$Me$^+$);
$^{19}$F NMR (282.38 MHz, CD$_2$Cl$_2$): δ−84.5 (t, $^3J_{FF}$=7.4, 2F, CF$_2$), −83.2 (t, $^3J_{FF}$=7.4, 2F, CF$_2$), −76.1 (s, 6F, CF$_3$);
$^{13}$C {$^1$H} NMR (100.62 MHz, CD$_2$Cl$_2$): δ30.1 (s, C(2)H$_3$), 32.2 (s, C(13)H$_2$), 33.6 (s, C(15)H$_3$), 50.8 (s, C(14)H$_2$), 75.6 (s, C(1)), 108.3 (m, C(8)), 110.8 (tt, $^1J_{CF}$=337, $^2J_{CF}$=39.0, CF$_2$), 117.0 (q, $^1J_{CF}$=292, CF$_3$COO—), 116.3 (tt, $^1J_{CF}$=278, $^2J_{CF}$=25.0, CF$_2$), 122.9 (s, C(10)H), 129.7 (s, C(4)H or C(6)H), 130.9 (s, C(11)H), 131.0 (t, $J_{CF}$=4.7, C(7)), 131.7 (s, C(4)H or C(6)H), 132.6 (s, C(5)H), 136.6 (s, C(12)), 147.7 (m, C(9)), 148.7 (bm, C(3)), 162.5 (q, $^2J_{CF}$=35.2, CF$_3$COO—);

HRMS (m/z, ESI$^+$): [M+H]$^+$ calcd. for C$_{20}$H$_{23}$F$_4$INO$_2$, 512.0704, found, 512.0699.

Anal. calcd. for C$_{24}$H$_{24}$F$_{10}$INO$_6$ [C] 38.99%, [H] 3.27%, [N] 1.89%, [O] 12.98%, [F] 25.70%, [I] 17.16%. Found: [C] 39.19%, [H] 3.27%, [N] 1.85%, [F] 25.52%.

Functionalized Carboxylic Acids and their Precursors 2-(2-(2-(2-Hydroxyethoxy)ethoxy)ethoxy)ethyl 4-methylbenzenesulfonate (IK28_Tosylate) [CAS 77544-60-6]

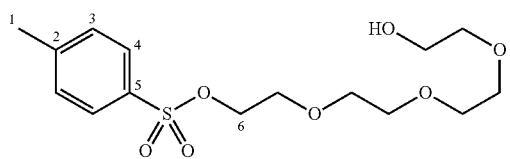 [SMILES: Cc1ccc(S(=O)(=O)OCCOCCOCCOCCO)cc1]

Sodium hydroxide (640 mg, 16 mmol) in H$_2$O (2.5 ml) was added to a solution of tetra(ethylene glycol) (17.3 mL, 0.1 mol) in THF (2.5 mL). The mixture was cooled down to 0° C. and p-toluenesulfonyl chloride (1.9 g, 10 mmol) in THF (7.5 mL) was slowly added. The mixture was stirred for 2 hours at 0° C., poured into water (40 mL), and the layers were separated. The aqueous phase was extracted with DCM (4×15 mL) and the combined organic portions were washed with water (3×15 mL) before being dried over MgSO$_4$, filtered, and concentrated under reduced pressure to yield the product as a colorless oil, which was used directly in the next step without further purification.

Yield: 3.2 g (91%);

$^1$H NMR (401.00 MHz, CDCl$_3$): δ 2.31 (s, 1H, OH), 2.44 (s, 3H, C(1)H$_3$), 3.55-3.72 (m, 14H, 7×CH$_2$), 4.15-4.17 (m, 2H, C(6)H$_2$), 7.33 (dq, 2H, $^3J_{HH}$=7.9, $^4J_{HH}$=1.0, C(4)H), 7.78-7.80 (m, 2H, C(3)H);

$^{13}$C NMR (100.84 MHz, CDCl$_3$): δ 21.6 (s, C(1)H$_3$), 61.7 (s, CH$_2$), 68.7 (s, CH$_2$), 69.2 (s, C(6)H$_2$), 70.3 (s, CH$_2$), 70.4 (s, CH$_2$), 70.6 (s, CH$_2$), 70.7 (s, CH$_2$), 72.4 (s, CH$_2$) 127.9 (s, 2×C(3)H), 129.8 (s, 2×C(4)H), 132.9 (s, C(5)H), 144.8 (s, C(2)H). The data were consistent with those reported by Cubberley and Iverson.

2-(2-(2-(2-Azidoethoxy)ethoxy)ethoxy)ethan-1-ol (IK28_azide) [CAS 86770-67-4]

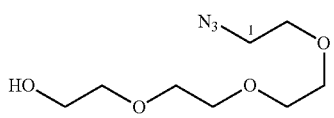 [SMILES: [N-]=[N+]=NCCOCCOCCOCCO]

Sodium azide (975 mg, 15 mmol) was added to a solution of 2-(2-(2-(2-Hydroxyethoxy)ethoxy)ethoxy)ethyl 4-methylbenzenesulfonate (3.18 g, 9.1 mmol) in CH$_3$CN (25 mL). The mixture was heated to reflux and stirred for 8 h. The solution was allowed to cool down to rt and H$_2$O (25 mL) was added. The aqueous phase was extracted with DCM (3×25 mL) and the combined organic portions were dried over MgSO$_4$, filtered, and concentrated under reduced pressure to give the product as a pale yellow oil, which was used directly in the next step without further purification.

Yield: 1.97 g (99%);

$^1$H NMR (401.00 MHz, CDCl$_3$): δ 2.38 (s, 1H, OH), 3.39 (t, 2H, $^3J_{HH}$=5.1 Hz, C(1)H$_2$), 3.60-3.74 (m, 14H, 7×CH$_2$);

$^{13}$C NMR (100.84 MHz, CDCl$_3$): δ 50.6 (s, C(1)H$_2$), 61.7 (s, CH$_2$), 70.0 (s, CH$_2$), 70.3 (s, CH$_2$), 70.6 (s, CH$_2$), 70.7 (m, 2×CH$_2$), 72.4 (s, CH$_2$). The data were consistent with those reported by Cubberley and Iverson.

Ethyl 14-azido-3,6,9,12-tetraoxatetradecanoate (IK28_Ester) [CAS 256397-65-6]

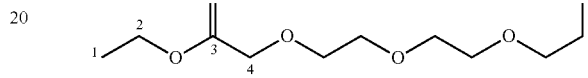

Sodium hydride (341 mg, 13.5 mmol) was dispersed in dry THF (10 ml) under an argon atmosphere. The mixture was cooled to 0° C. and a solution of 2-(2-(2-(2-Azidoethoxy)ethoxy)ethoxy)ethan-1-ol (1.97 g, 9 mmol) in dry THF (10 mL) was added dropwise. The mixture was stirred for 1 h at rt and then cooled down to 0° C. Ethyl bromoacetate (1.53 mL, 13.5 mmol) was slowly added and the mixture was stirred for 1 h at rt and 16 h at 50° C. The reaction mixture was cooled down to rt and quenched with water (10 mL). THF was evaporated under reduced pressure and the residue was extracted with EtOAc (3×20 mL). Organic layers were dried over MgSO$_4$, filtered and concentrated under reduced pressure to give crude orange oil. Purification by column chromatography (gradient elution from hexane: EtOAc 1:1 to 1:2) afforded the product as a yellow oil.

Yield: 1.62 g (72%); $R_f$=0.36 (EtOAc:hexane 1:1);

$^1$H NMR (401.00 MHz, CDCl$_3$): δ 1.28 (t, 3H, $^3J_{HH}$=7.2 Hz, C(1)H$_3$), 3.38 (t, 2H, $^3J_{HH}$=5.1 Hz, C(5)H$_2$), 3.64-3.74 (m, 14H, 7×CH$_2$), 4.14 (s, 2H, C(4)H$_2$), 4.21 (q, 2H, $^3J_{HH}$=7.2 Hz, C(2)H$_2$);

$^{13}$C NMR (100.84 MHz, CDCl$_3$): δ 14.1 (s, C(1)H$_3$), 50.6 (s, C(5)H$_2$), 60.7 (s, C(2)H$_2$), 68.7 (s, C(4)H$_2$), 70.0 (s, CH$_2$), 70.5-70.6 (m, 5×CH$_2$), 70.8 (s, CH$_2$) 170.4 (s, C(3)). The data were consistent with those reported by Shirude et al.

14-Azido-3,6,9,12-tetraoxatetradecanoic Acid (IK30) [CAS 201467-81-4]

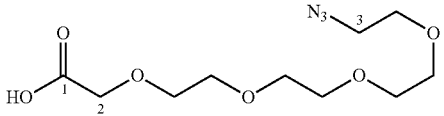 [SMILES: [N-]=[N+]=NCCOCCOCCOCCOCC(=O)O]

Ethyl 14-azido-3,6,9,12-tetraoxatetradecanoate (173 mg, 0.57 mmol) was dissolved in 66% MeOH in water (2 mL), NaOH (79 mg, 1.98 mmol) was added, and the reaction mixture was stirred overnight. The mixture was concentrated under reduced pressure, the residue was acidified by 1M HCl to pH=2 and extracted with EtOAc (2×10 mL). The organic layers were dried over MgSO$_4$, filtered, and concentrated under reduced pressure. The product was obtained as a yellow oil.

Yield: 134 mg (85%);

$^1$H NMR (401.00 MHz, CDCl$_3$): δ3.31 (t, 2H, $^3J_{HH}$=5.0 Hz, C(3)H$_2$), 3.58-3.63 (m, 12H, 6×CH$_2$), 3.66-3.68 (m, 2H, CH$_2$), 4.10 (s, 2H, C(2)H$_2$), 10.10 (br s, 1H, COOH);

$^{13}$C NMR (100.84 MHz, CDCl$_3$): δ50.3 (s, C(3)H$_2$), 68.2 (s, C(2)H$_2$), 69.7 (s, CH$_2$), 70.1 (s, CH$_2$), 70.2-70.3 (m, 4×CH$_2$), 70.8 (s, CH$_2$) 173.3 (s, C(1)). The data were consistent with those reported by Bogdan et al.

Ethyl 3,6,9,12,15-pentaoxaoctadec-17-ynoate (IK72)

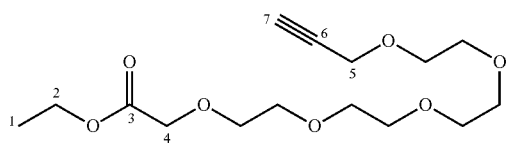 [SMILES: C#CCOCCOCCOCCOCCOCC(=O)OCC]

Sodium hydride (162 mg, 6.4 mmol) was dispersed in dry THF (12 mL) under an argon atmosphere. The mixture was cooled down to 0° C. and tetra(ethylene glycol) (3.5 ml, 20 mmol) was added dropwise. The mixture was stirred for 1 h at rt and then cooled down to 0° C. Propargyl bromide (80% in toluene, 0.43 mL, 4 mmol) was slowly added and the mixture was stirred overnight at rt. The reaction mixture was quenched with water (20 mL) and extracted with DCM (4×7 mL). The organic layers were washed with water (3×7 mL), dried over MgSO$_4$, filtered and concentrated under reduced pressure to give crude 3,6,9,12-tetraoxapentadec-14-yn-1-ol (674 mg) as a yellow oil, which was used directly in the next step without further purification.

Sodium hydride (73 mg, 2.9 mmol) was dispersed in dry THF (2.5 mL) under an argon atmosphere. The mixture was cooled to 0° C. and solution of 3,6,9,12-tetraoxapentadec-14-yn-1-ol (674 mg, 2.9 mmol) in dry THF (2.5 ml) was added dropwise. The mixture was stirred 1 h at rt and cooled to 0° C. Ethyl bromoacetate (0.39 mL, 3.5 mmol) was slowly added and the mixture was stirred at rt overnight. The reaction mixture was quenched with water (5 mL) and extracted with DCM (3×5 mL). Organic layers were dried over MgSO$_4$, filtered and concentrated under reduced pressure to give the crude product. Purification by column chromatography (gradient elution from hexane:EtOAc 1:1 to 1:2) afforded the product as a pale yellow oil.

Yield: 500 mg (39%); R$_f$=0.31 (EtOAc:hexane 1:1);

$^1$H NMR (401.00 MHz, CDCl$_3$): δ 1.28 (t, 3H, $^3J_{HH}$=7.2 Hz, C(1)H$_3$), 2.42 (t, 1H, $^3J_{HH}$=2.4 Hz, C(7)H), 3.64-3.74 (m, 16H, 8×CH$_2$), 4.14 (s, 2H, C(4)H$_2$), 4.18-4.24 (m, 4H, C(5)H$_2$, C(2)H$_2$);

$^{13}$C NMR (100.84 MHz, CDCl$_3$): δ14.0 (s, C(1)H$_3$), 58.1 (s, C(5)H$_2$), 60.5 (s, C(2)H$_2$), 68.5 (s, C(4)H$_2$), 68.8 (s, CH$_2$), 70.2 (s, CH$_2$), 70.3-70.4 (m, 5×CH$_2$), 70.6 (s, CH$_2$), 74.4 (s, C(7)H), 79.4 (s, C(6)), 170.2 (s, C(3)).

HRMS (m/z, ESI$^+$): [M+Na]$^+$ calcd. for C$_{15}$H$_{26}$NaO$_7$, 341.1571; found, 341.1571.

3,6,9,12,15-Pentaoxaoctadec-17-ynoic Acid (IK73)

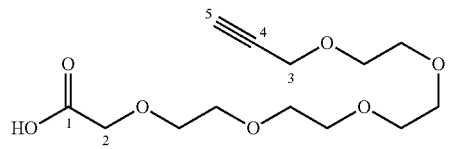

Ethyl 3,6,9,12,15-pentaoxaoctadec-17-ynoate (102 mg, 0.32 mmol) was dissolved in 66% MeOH in water (1 mL), NaOH (45 mg, 1.12 mmol) was added, and the mixture was stirred overnight. The mixture was concentrated under reduced pressure, the residue was acidified by 1M HCl to pH=2 and extracted with DCM (3×5 mL). The organic layers were dried over MgSO$_4$, filtered and concentrated under reduced pressure. The product was obtained as a pale yellow oil.

Yield: 88 mg (95%);

$^1$H NMR (401.00 MHz, CDCl$_3$): δ2.41 (t, 1H, $^3J_{HH}$=2.4 Hz, C(5)H), 3.58-3.66 (m, 14H, 7×CH$_2$), 3.68-3.71 (m, 2H, CH$_2$), 4.12 (s, 2H, C(2)H$_2$), 4.15 (d, 2H, $^3J_{HH}$=2.4 Hz, C(3)H$_2$), 9.65 (brs, 1H, OH);

$^{13}$C NMR (100.84 MHz, CDCl$_3$): δ58.2 (s, C(3)H$_2$), 68.5 (s, C(2)H$_2$), 68.8 (s, CH$_2$), 70.1-70.4 (m, 6×CH$_2$), 71.0 (s, CH$_2$), 74.5 (s, C(5)H), 79.4 (s, C(4)), 173.0 (s, C(1)).

HRMS (m/z, ESI$^+$): [M+Na]$^+$ calcd. for C$_{13}$H$_{22}$NaO$_7$, 313.1258; found, 313.1258.

1-((Prop-2-yn-1-yloxy)methyl)pyrene (IK43)

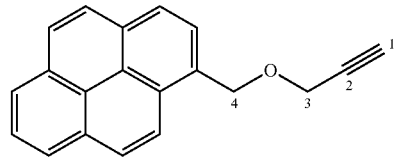 [SMILES: C#CCOCc1ccc2ccc3cccc4ccc1c2c34]

1-Pyrenemethanol (929 mg, 4 mmol) was dispersed in toluene (50 mL). The mixture was heated to 40° C. and PBr$_3$ (0.5 mL, 4.9 mmol) was added. The flask was sealed and reaction mixture was heated to 80° C. After 2 hours, the reaction mixture was cooled down and quenched by saturated sodium carbonate solution (24 mL). An organic layer was separated, washed with water (2×20 mL) and brine (2×20 mL), dried over MgSO$_4$, filtered, and concentrated under reduced pressure to give crude 4-(bromomethyl)pyrene (1.12 g) as yellow crystals, which was used directly in the next step without further purification.

Sodium hydride (131 mg, 5.2 mmol) was dispersed in dry THF (10 mL) under an argon atmosphere. The mixture was cooled down to 0° C. and propargyl alcohol (0.48 mL, 8 mmol) was added dropwise. The mixture was stirred for 30 min at rt and then cooled down to 0° C. A solution of 4-(bromomethyl)pyrene (1.12 g, 4 mmol) in THF (15 mL) was slowly added and the mixture was stirred at rt overnight. The reaction mixture was quenched with saturated NH$_4$Cl (20 mL). THF was evaporated under reduced pressure and the residue was extracted with DCM (4×10 mL). The organic layers were washed with brine (10 mL), dried (MgSO$_4$), filtered and concentrated under reduced pressure to give the crude product. Purification by column chromatography (hexane:EtOAc 20:1) afforded the title compound as pale yellow crystals.

Yield: 848 mg (72%); m.p. 84-85° C.; $R_f$=0.35 (EtOAc:hexane 1:20);

$^1$H NMR (401.00 MHz, CDCl$_3$): δ 2.59 (t, 1H, $^3J_{HH}$=2.4 Hz, C(1)H), 4.29 (d, 2H, $^3J_{HH}$=2.4 Hz, C(3)H$_2$), 5.34 (s, 2H, C(4)H$_2$), 7.98-8.10 (m, 4H, C$_{Ar}$H), 8.11-8.25 (m, 4H, C$_{Ar}$H), 8.41 (d, $^3J_{HH}$=9.2 Hz, 1H, C$_{Ar}$H);

$^{13}$C NMR (100.84 MHz, CDCl$_3$): δ57.1 (s, C(3)H$_2$), 69.9 (s, C(4)H$_2$), 74.9 (s, C(1)H), 79.8 (s, C(2)), 123.3 (s, C$_{Ar}$H), 124.4 (s, C$_{Ar}$H), 124.6 (s, C$_{Ar}$), 124.9 (s, C$_{Ar}$), 125.2-125.3 (s, 2×C$_{Ar}$H), 125.9 (s, C$_{Ar}$H), 127.3 (s, C$_{Ar}$H), 127.4 (s, C$_{Ar}$H), 127.5 (s, C$_{Ar}$H), 127.8 (s, C$_{Ar}$H), 129.6 (s, C$_{Ar}$), 130.2 (s, C$_{Ar}$), 130.7 (s, C$_{Ar}$), 131.2 (s, C$_{Ar}$), 131.5 (s, C$_{Ar}$).

HRMS (m/z, CI$^+$): [M]$^+$ calcd. for C$_{20}$H$_{14}$O, 270.1045; found, 270.1046.

Ethyl 14-(4-((pyren-1-ylmethoxy)methyl)-1H-1,2,3-triazol-1-yl)-3,6,9,12-tetraoxatetradecanoate (IK15)

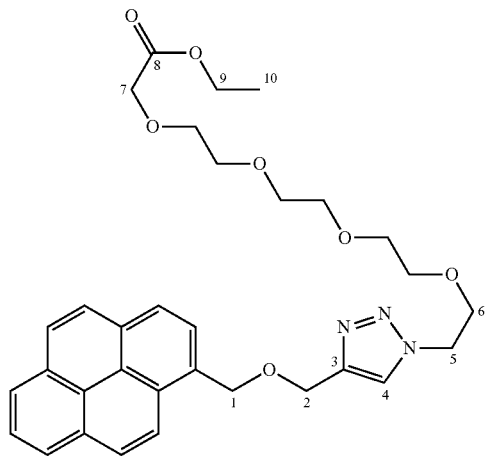 [SMILES: CCOC(=O)COCCOCCOCCOCCn1cc(COCc2ccc3ccc4cccc5ccc2c3c45)nn1]

Ethyl 14-azido-3,6,9,12-tetraoxatetradecanoate (763 mg, 2.5 mmol) and 4-((prop-2-yn-1-yloxy)methyl)pyrene (541 mg, 2 mmol) were dissolved in THF (20 mL). 0.01 M aqueous solution of CuSO$_4$.5H$_2$O (10 mL) was added to the mixture while stirring, followed by 0.02 M solution of sodium L-ascorbate (10 mL). The pale yellow solution was stirred at rt for 2 h, then another portion (5 mL) of the sodium L-ascorbate solution was added, and the reaction mixture was stirred for 1 h. THF and water were evaporated on a rotary evaporator and the residue was extracted with EtOAc (3×15 mL), dried over MgSO$_4$, filtered, and concentrated under reduced pressure. The crude product was purified by column chromatography (gradient elution from DCM:acetone 7:1 to 2:1), affording a pale yellow oil.

Yield: 1.035 g (90%); $R_f$=0.4 (DCM:acetone 7:1);

$^1$H NMR (400.13 MHz, CDCl$_3$): δ 1.24 (t, 3H, $^3J_{HH}$=7.1 Hz, C(10)H$_3$), 3.50-3.57 (m, 10H, CH$_2$), 3.60-3.63 (m, 2H, CH$_2$), 3.82 (t, 2H, $^3J_{HH}$=5.0 Hz, C(6)H$_2$), 4.06 (s, 2H, C(7)H$_2$), 4.17 (q, 2H, $^3J_{HH}$=7.1 Hz, C(9)H$_2$), 4.51 (t, 2H, $^3J_{HH}$=5.0 Hz, C(5)H$_2$), 4.82 (s, 2H, C(2)H$_2$) 5.31 (s, 2H, C(1)H$_2$), 7.74 (s, 1H, C(4)H), 7.98-8.05 (m, 4H, C$_{Ar}$H), 8.11-8.20 (m, 4H, C$_{Ar}$H), 8.34 (d, $^3J_{HH}$=9.3 Hz, 1H, C$_{Ar}$H);

$^{13}$C NMR (100.84 MHz, CDC$_3$): δ 14.1 (s, C(10)H$_3$), 50.2 (s, C(5)H$_2$), 60.7 (s, C(9)H$_2$), 63.7 (s, C(2)H$_2$), 68.5 (s, C(7)H$_2$), 69.4 (s, C(6)H$_2$), 70.3-70.7 (m, 6×CH$_2$), 70.9 (s, C(1)H$_2$), 123.4 (s, C$_{Ar}$H), 123.9 (s, C(4)H), 124.4 (s, C$_{Ar}$H), 124.6 (s, C$_{Ar}$), 124.8 (s, C$_{Ar}$), 125.2 (s, 2×C$_{Ar}$H), 125.9 (s, C$_{Ar}$H), 127.2 (s, C$_{Ar}$H), 127.3 (s, C$_{Ar}$H), 127.4 (s, C$_{Ar}$H), 127.7 (s, C$_{Ar}$H), 129.3 (s, C$_{Ar}$), 130.7 (s, C$_{Ar}$), 131.0 (s, C$_{Ar}$), 131.1 (s, C$_{Ar}$), 131.3 (s, C$_{Ar}$), 145.0 (s, C(3)), 170.3 (s, C(8)).

HRMS (m/z, ESI$^+$): [M+Na]$^+$ calcd. for C$_{32}$H$_{37}$N$_3$NaO$_7$, 598.2524; found, 598.2524.

14-(4-((pyren-1-ylmethoxy)methyl)-1H-1,2,3-triazol-1-yl)-3,6,9,12-tetraoxatetradecanoic Acid (IK75)

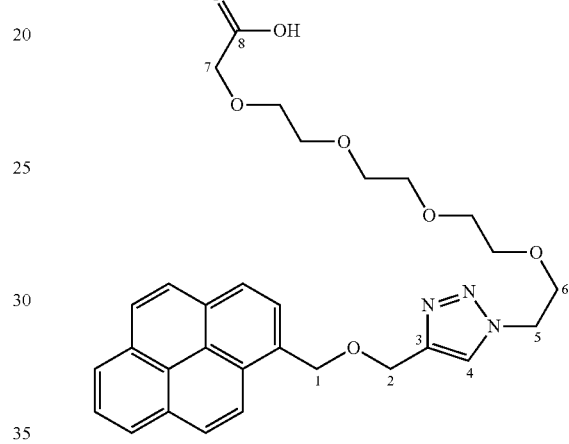

Ethyl 14-(4-((pyren-4-ylmethoxy)methyl)-1H-1,2,3-triazol-1-yl)-3,6,9,12-tetraoxatetradecanoate (830 mg, 1.44 mmol) was dissolved in 66% MeOH in water (6 mL) and NaOH (202 mg, 5.05 mmol) was added, and the mixture was stirred overnight. The mixture was concentrated under reduced pressure, the residue was acidified by 1M HCl to pH=2 and extracted with EtOAc (3×25 mL). The organic layers were dried over MgSO$_4$, filtered and concentrated under reduced pressure. The product was obtained as a pale yellow oil.

Yield: 787 mg (99%);

$^1$H NMR (401.00 MHz, CDCl$_3$): δ 3.42-3.49 (m, 10H, CH$_2$), 3.54-3.56 (m, 2H, CH$_2$), 3.76 (t, 2H, $^3J_{HH}$=5.0 Hz, C(6)H$_2$), 4.05 (s, 2H, C(7)H$_2$), 4.47 (t, 2H, $^3J_{HH}$=5.0 Hz, C(5)H$_2$), 4.81 (s, 2H, C(2)H$_2$) 5.26 (s, 2H, C(1)H$_2$), 7.74 (s, 1H, C(4)H), 7.94-8.02 (m, 4H, C$_{Ar}$H), 8.06-8.16 (m, 4H, C$_{Ar}$H), 8.29 (d, $^3J_{HH}$=9.2 Hz, 1H, C$_{Ar}$H), 9.56 (br s, 1H, OH);

$^{13}$C NMR (100.84 MHz, CDCl$_3$): δ 50.2 (s, C(5)H$_2$), 63.4 (s, C(2)H$_2$), 68.5 (s, C(7)H$_2$), 69.1 (s, C(6)H$_2$), 70.0-70.3 (m, 5×CH$_2$), 70.8 (m, CH$_2$, C(1)H$_2$), 123.3 (s, C$_{Ar}$H), 124.1 (s, C(4)H), 124.3 (s, C$_{Ar}$H), 124.5 (s, C$_{Ar}$), 124.7 (s, C$_{Ar}$), 125.1 (s, 2×C$_{Ar}$H), 125.8 (s, C$_{Ar}$H), 127.1 (s, C$_{Ar}$H), 127.2 (s, C$_{Ar}$H), 127.3 (s, C$_{Ar}$H), 127.6 (s, C$_{Ar}$H), 129.2 (s, C$_{Ar}$), 130.6 (s, C$_{Ar}$), 130.8 (s, C$_{Ar}$), 131.0 (s, C$_{Ar}$), 131.2 (s, C$_{Ar}$), 144.6 (s, C(3)), 172.4 (s, C(8)).

HRMS (m/z, ESI$^+$): [M+Na]$^+$ calcd. for C$_{30}$H$_{33}$N$_3$NaO$_7$, 570.2211; found, 570.2211.

2-Bromo-N-(3',6'-dihydroxy-3-oxo-3H-spiro[isobenzofuran-1,9'-xanthen]-6-yl)acetamide (#) AK10-9 [CAS 107142-62-1]

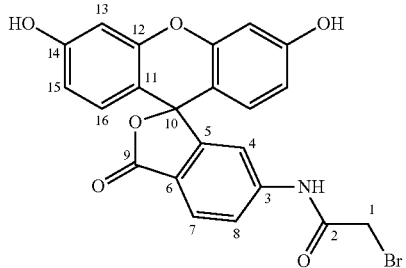

6-Aminofluorescein (500 mg, 1.44 mmol) and NaHCO$_3$ (363 mg, 4.32 mmol) were suspended in anhydrous THF (4.5 mL), and the mixture was stirred for 15 min at 0° C. A solution of bromoacetyl bromide (581 mg, 2.88 mmol) in anhydrous THF (1.5 mL) was added dropwise. After 15 min, the solvent was evaporated, followed by addition of HCl (5 mL, conc.?). The pH was adjusted to ~4 using NaOH. The resulting precipitate was filtered off, the aqueous phase was extracted with EtOAc (3×5 mL), the extract was combined with the filter cake, and the mixture was concentrated to dryness. The crude product was purified by column chromatography (gradient elution from EtOAc:hexane 7:3 to EtOAc) to give an orange solid.

Yield: 261 mg (39%); m.p. ~230° C. (dec.); R$_f$=0.7 (EtOAc);

$^1$H NMR (299.78 MHz, CD$_3$OD): δ3.90 (bs, 2H, C(1)H$_2$), 6.53 (dd, $^3J_{HH}$=8.7, $^4J_{HH}$=2.4, 2H, C(15)H), 6.62 (d, $^3J_{HH}$=8.7, 2H, C(16)H), 6.68 (d, $^4J_{HH}$=2.4, 2H, C(13)H), 7.57 (dd, $^4J_{HH}$=1.8, $^5J_{HH}$=0.6, 1H, C(4)H), 7.76 (dd, $^3J_{HH}$=8.4, $^4J_{HH}$=1.8, 1H, C(8)H), 7.93 (dd, $^3J_{HH}$=8.4, $^5J_{HH}$=0.6, 1H, C(7)H);

$^{13}$C NMR (100.66 MHz, CD$_3$OD): δ 29.5 (s, C(1)H$_2$), 86.8 (bs, C(10)), 103.5 (s, C(13)H), 111.2 (s, C(11)), 113.6 (s, C(15)H), 115.1 (s, C(4)H), 122.1 (s, C(8)H), 123.3 (s, C(6)), 126.8 (s, C(7)H), 130.2 (s, C(16)H), 146.2 (s, C(3)), 153.9 (s, C(12) or C(14)), 155.8 (s, C(5)), 161.2 (s, C(12) or C(14)), 168.0 (s, C(2)), 171.1 (s, C(9));

HRMS (m/z, ESI$^+$): [M+H]$^+$ calcd. for C$_{22}$H$_{15}$BrNO$_6$, 468.0077; found, 468.0073.

Derivatives of # NMT

General Procedure for the Synthesis of Amide Reagents #

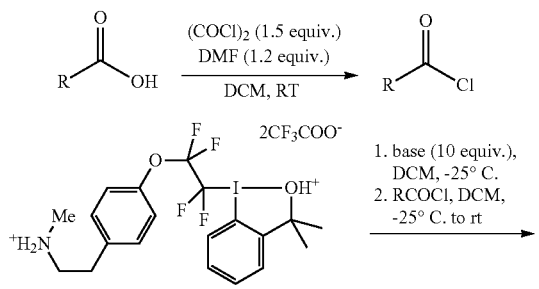

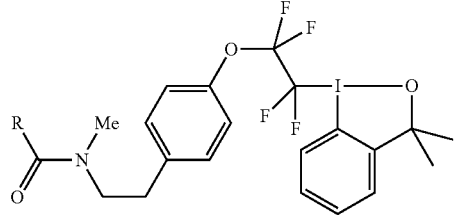

To a carboxylic acid (0.12 mmol, 1.2 equiv.) in an oven-dried Schlenk flask, anhydrous DCM (2 mL) was added at rt. (COCl)$_2$ (13 µL, 0.15 mmol, 1.5 equiv.) and DMF (9 µL, 0.12 mmol, 1.2 equiv.) were added, the mixture was stirred for 2 h at rt, and concentrated to dryness. The resulting acyl chloride was dissolved in DCM (2 mL).

The NMT reagent (74 mg, 0.1 mmol, 1.0 equiv.) was dissolved in DCM (1 mL) in another Schlenk flask at −25° C., and a base (1 mmol, 10 equiv.) was added. The solution of acyl chloride was added dropwise, and the mixture was stirred at −25° C. to rt for a given period of time. In some cases, the reaction mixture was diluted with DCM (5 mL) and washed with pH 4 phosphate buffer (2×10 mL), aqueous NaHCO$_3$ (2×10 mL), brine (2×10 mL), dried over Na$_2$SO$_4$, and concentrated onto Celite. The crude product was purified by automated flash chromatography.

N-(4-(2-(3,3-Dimethyl-1λ$^3$-benzo[d][1,2]iodaoxol-1(3H)-yl)-1,1,2,2-tetrafluoroethoxy)phenethyl)-N-methylpyrene-1-carboxamide (#) JV106 and JV131-4

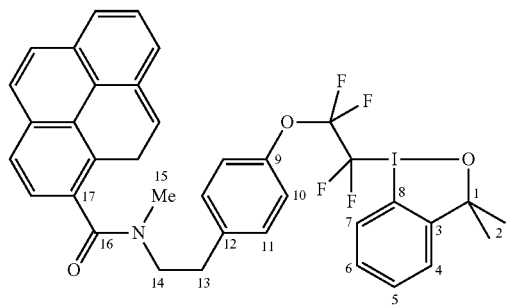

The title compound was prepared according to the general procedure starting from 1-pyrenecarboxylic acid (0.06 mmol) using Et$_3$N as the base. The reaction time was 2 h. The reaction mixture was directly concentrated on Celite, and the product was isolated by automated flash chromatography (12 g SiO$_2$ column, gradient elution from hexane to EtOAc) as a colourless oil.

Yield: 33 mg (89%); R$_f$=0.34 (EtOAc);

$^1$H NMR (500.13 MHz, CDCl$_3$): δ 1.50 and 1.52 (s, 6H, C(2)H$_3$), 2.73 and 3.18 (bm, 2H, C(13)H$_2$), 2.72 and 3.37 (s, 3H, C(15)H$_3$), 3.34 and 4.04 (bm, 2H, C(14)H$_2$), 6.73 and 7.44 (m, 2H, C(11)H), 6.95 and 7.26 (m, 2H, C(10)H), 7.38 (m, 2H, C(4)H and C(6)H), 7.47 (m, 1H, C(5)H), 7.49 and 7.93 (m, 1H, C$_{Ar}$H), 7.73 and 7.79 (m, 1H, C(7)H), 7.81 (m, 1H, C$_{Ar}$H), 8.00-8.24 (m, 7H, C$_{Ar}$H);

$^{19}$F NMR (470.55 MHz, CDCl$_3$): δ−97.3 (bs, 2F, CF$_2$), −84.7 and −84.6 (bm, 2F, CF$_2$);

$^{13}$C {$^1$H} NMR (125.77 MHz, CDCl$_3$): δ 30.9 (s, C(2)H$_3$), 32.8 and 37.2 (s, C(15)H$_3$), 32.9 and 34.0 (s, C(13)H$_2$), 48.4 and 52.6 (s, C(14)H$_2$), 76.3 (bs, C(1)), 110.9 (m, C(8)), 111.3 and 111.4 (tt, $^1J_{CF}$=337, $^2J_{CF}$=38.3, CF$_2$), 117.2 and 117.3 (tt, $^1J_{CF}$=277, $^2J_{CF}$=25.9, CF$_2$), 121.7 (s, C(10)H), 123.7 and 123.7 (s, C$_{Ar}$H), 123.7 and 123.8 (s, C$_{Ar}$H), 124.4 and 124.4 (s, C$_{Ar}$), 124.5 (s, C$_{Ar}$H), 124.5 and 124.5 (s, C$_{Ar}$), 124.7 (s, C$_{Ar}$H), 125.5 and 125.6 (s, C$_{Ar}$H), 125.7 and 125.7 (s, C$_{Ar}$H), 126.3 and 126.3 (s, C$_{Ar}$H), 127.1 (s, C$_{Ar}$), 127.1 and 127.2 (s, C$_{Ar}$H), 127.4 (s, C(4)H or C(6)H), 128.1 and 128.1 (s, C$_{Ar}$H), 128.6 and 128.7 (s, C$_{Ar}$H), 129.1 (m, C(7)), 129.4 (s, C(4)H or C(6)H), 129.9 and 130.3 (s, C(11)H), 130.4 (s, C(5)H), 130.7 and 130.7 (s, C$_{Ar}$), 131.0 and 131.5 (s, C(17)), 131.1 and 131.2 (s, C$_{Ar}$), 131.5 and 131.5 (s, C$_{Ar}$), 136.4 and 137.5 (s, C(12)), 147.3 and 147.5 (bm, C(9)), 149.8 (m, C(3)), 171.2 and 171.5 (s, C(16));

HRMS (m/z, ESI$^+$): [M+H]$^+$ calcd. for C$_{37}$H$_{31}$F$_4$INO$_3$, 740.1279, found, 740.1270.

N-(4-(2-(3,3-Dimethyl-1λ$^3$-benzo[d][1,2]iodaoxol-1(3H)-yl)-1,1,2,2-tetrafluoroethoxy)phenethyl)-4-iodo-N-methylbenzamide (#) JV136-1

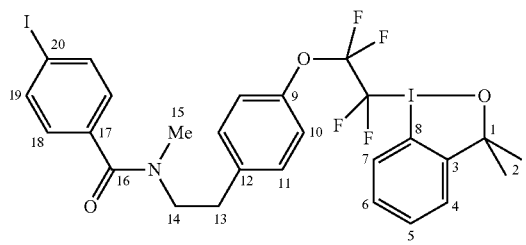 [SMILES: CN(CCc1ccc(OC(F)(F)C(F)(F)I2OC(C)(C)c3ccccc32)cc1)C(=O)c1ccc(I)cc1]

The title compound was prepared according to the general procedure starting from 4-iodobenzoic acid (0.12 mmol) using Et$_3$N as the base. The reaction time was 1 h. The reaction mixture was directly concentrated on Celite, and the product was isolated by automated flash chromatography (12 g SiO$_2$ column, gradient elution from hexane to EtOAc) as a colourless oil.

Yield: 60 mg (81%); R$_f$=0.39 (EtOAc);

$^1$H NMR (400.13 MHz, CDCl$_3$): δ 1.51 (s, 6H, C(2)H$_3$), 2.79 and 2.99 (bs, 2H, C(13)H$_2$), 2.82 and 3.13 (bs, 3H, C(15)H$_3$), 3.48c and 3.74 (bs, 2H, C(14)H$_2$), 6.70-7.20 (bm, 5H, C$_{Ar}$H), 7.29 (bm, 1H, C$_{Ar}$H), 7.40 (m, 2H, C(4)H and C(6)H), 7.51 (m, 1H, C(5)H), 7.63 (bm, 1H, C$_{Ar}$H), 7.72 (bm, 1H, C$_{Ar}$H), 7.74 (m, 1H, C(7)H); $^{19}$F NMR (376.46 MHz, CDCl$_3$): δ–97.5 (bs, 2F, CF$_2$), –84.8 and –84.7 (bs, 2F, CF$_2$);

$^{13}$C {$^1$H} NMR (100.62 MHz, CDCl$_3$): δ 30.9 (s, C(2)H$_3$), 32.6 and 33.8 (s, C(13)H$_2$), 33.0 and 38.1 (s, C(15)H$_3$), 49.1 and 52.6 (s, C(14)H$_2$), 76.3 (s, C(1)), 95.3 and 95.6 (bs, C(20)), 111.0 (m, C(8)), 111.4 (tt, $^1J_{CF}$=338, $^2J_{CF}$=38.0, CF$_2$), 117.2 (tt, $^1J_{CF}$=277, $^2J_{CF}$=26.0, CF$_2$), 121.7 (bs, C$_{Ar}$H), 122.0 (bs, C$_{Ar}$H), 127.4 (s, C(4)H or C(6)H), 128.2 and 128.6 (bs, C$_{Ar}$H), 128.9 (t, J$_{CF}$=5.3, C(7)), 129.4 (s, C(4)H or C(6)H), 130.1 (s, C$_{Ar}$H), 130.3 (s, C(5)H), 135.6 and 135.7 (bs, C$_{Ar}$), 136.4 (bs, C$_{Ar}$), 137.5 (bs, C$_{Ar}$H), 147.4 and 147.5 (m, C(9)), 149.9 (s, C(3)), 170.4 and 171.1 (s, C(16));

HRMS (m/z, ESI$^+$): [M+H]$^+$ calcd. for C$_{27}$H$_{26}$F$_4$I$_2$NO$_3$, 741.9933, found, 741.9920.

4-Azido-N-(4-(2-(3,3-Dimethyl-1λ$^3$-benzo[d][1,2]iodaoxol-1(3H)-yl)-1,1,2,2-tetrafluoroethoxy)phenethyl)-N-methylbenzamide (#) JV137-1

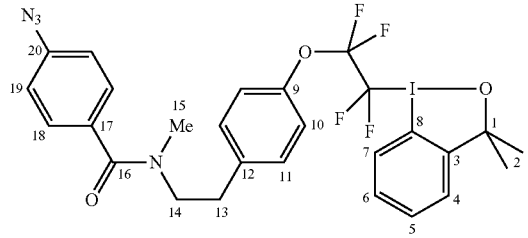 [SMILES: CN(CCc1ccc(OC(F)(F)C(F)(F)I2OC(C)(C)c3ccccc32)cc1)C(=O)c1ccc(N=[N+]=[N-])cc1]

The title compound was prepared according to the general procedure starting from 4-azidobenzoic acid (0.12 mmol) using Et$_3$N as the base. The reaction time was 2 h. The reaction mixture was directly concentrated on Celite, and the product was isolated by automated flash chromatography (12 g SiO$_2$ column, gradient elution from hexane to EtOAc) as a colourless oil.

Yield: 45 mg (69%); R$_f$=0.31 (EtOAc);

$^1$H NMR (400.13 MHz, CDCl$_3$): δ 1.50 (s, 6H, C(2)H$_3$), 2.80 and 2.98 (bs, 2H, C(13)H$_2$), 2.85 and 3.12 (bs, 3H, C(15)H$_3$), 3.51 and 3.74 (bs, 2H, C(14)H$_2$), 6.88-7.36 (bm, 8H, C$_{Ar}$H), 7.39 (m, 2H, C(4)H and C(6)H), 7.50 (m, 1H, C(5)H), 7.74 (m, 1H, C(7)H);

$^{19}$F NMR (376.46 MHz, CDCl$_3$): δ–97.5 (bs, 2F, CF$_2$), –84.7 (bs, 2F, CF$_2$);

$^{13}$C {$^1$H} NMR (100.62 MHz, CDCl$_3$): δ 30.9 (s, C(2)H$_3$), 32.7 and 33.8 (s, C(13)H$_2$), 33.1 and 38.2 (s, C(15)H$_3$), 49.3 and 52.7 (s, C(14)H$_2$), 76.3 (bs, C(1)), 110.9 (m, C(8)), 111.4 (tt, $^1J_{CF}$=337, $^2J_{CF}$=38.5, CF$_2$), 117.2 (tt, $^1J_{CF}$=276, $^2J_{CF}$=25.0, CF$_2$), 118.8 (s, C$_{Ar}$H) 121.8 (bs, C$_{Ar}$H), 127.4 (s, C(4)H or C(6)H), 128.4 and 128.7 (bs, C$_{Ar}$H), 129.0 (t, J$_{CF}$=5.2, C(7)), 129.4 (s, C(4)H or C(6)H), 130.1 (s, C$_{Ar}$H), 130.3 (s, C(5)H), 132.8 (s, C$_{Ar}$), 136.6 and 137.5 (bs, C$_{Ar}$), 141.3 (bs, C(20)), 147.4 (bm, C(9)), 149.8 (s, C(3)), 170.4 and 171.2 (s, C(16));

HRMS (m/z, ESI$^+$): [M+H]$^+$ calcd. for C$_{27}$H$_{26}$F$_4$IN$_4$O$_3$, 657.0980, found, 657.0983.

N-(4-(2-(3,3-Dimethyl-1λ$^3$-benzo[d][1,2]iodaoxol-1(3H)-yl)-1,1,2,2-tetrafluoroethoxy)phenethyl)-N-methyl-4-(4,4,5,5-tetramethyl-4-(4,4,5,5-tetramethyl-1,3,2-dioxaborolan-2-yl)benzamide (#) JV140-1

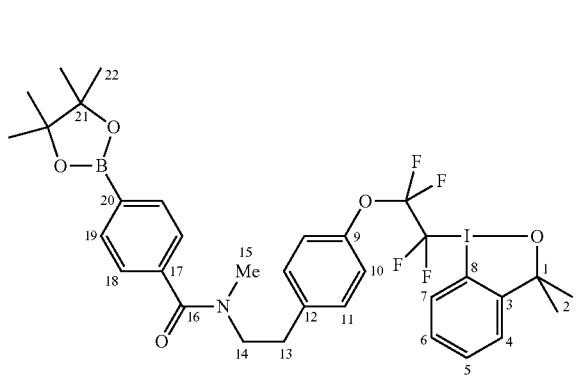

The title compound was prepared according to the general procedure starting from 4-(4,4,5,5-Tetramethyl-1,3,2-dioxaborolan-2-yl)benzoic acid (0.12 mmol) using Et$_3$N as the base. The reaction time was 2 h. The reaction mixture was directly concentrated on Celite, and the product was isolated by automated flash chromatography (12 g SiO$_2$ column, gradient elution from hexane to EtOAc) as a colourless oil.

Yield: 51 mg (69%); R$_f$=0.44 (EtOAc);

$^1$H NMR (500.13 MHz, CDCl$_3$): δ 1.34 (s, 12H, C(22)H$_3$), 1.50 (s, 6H, C(2)H$_3$), 2.78 and 2.99 (bs, 2H, C(13)H$_2$), 2.80 and 3.12 (bs, 3H, C(15)H$_3$), 3.45 and 3.75 (bs, 2H, C(14)H$_2$), 6.90-7.20 (bm, 4H, C$_{Ar}$H), 7.29 (bm, 2H, C$_{Ar}$H), 7.39 (m, 2H, C(4)H and C(6)H), 7.49 (m, 1H, C(5)H), 7.75 (m, 1H, C(7)H), 7.81 (bm, 2H, C$_{Ar}$H);

$^{19}$F NMR (470.55 MHz, CDCl$_3$): δ−97.3 (bs, 2F, CF$_2$), −84.7 and −84.6 (bs, 2F, CF$_2$);

$^{13}$C {$^1$H} NMR (125.77 MHz, CDCl$_3$): δ 24:9 (s, C(22)H$_3$), 30.9 (s, C(2)H$_3$), 32.7 and 34.0 (s, C(13)H$_2$), 33.0 and 38.1 (s, C(15)H$_3$), 49.1 and 52.6 (s, C(14)H$_2$), 76.3 (bs, C(1)), 84.0 (s, C(21)), 111.1 (m, C(8)), 111.5 (tt, $^1J_{CF}$=337, $^2J_{CF}$=38.0, CF$_2$), 117.3 (tt, $^1J_{CF}$=277, $^2J_{CF}$=26.0, CF$_2$), 121.7 and 121.8 (bs, C$_{Ar}$H), 127.4 (s, C(4)H or C(6)H), 125.6 and 125.9 (bs, C$_{Ar}$H), 129.2 (m, C(7)), 129.4 (s, C(4)H or C(6)H), 130.1 (bs, C$_{Ar}$H), 130.4 (s, C(5)H), 134.7 (bs, C$_{Ar}$H), 136.5 (bs, C$_{Ar}$), 137.6 (bs, C$_{Ar}$), 139.0 (bs, C$_{Ar}$), 147.4 (bm, C(9)), 149.9 (s, C(3)), 171.2 and 171.9 (s, C(16));

HRMS (m/z, ESI/MALDI): [M+H]$^+$ calcd. for C$_{33}$H$_{38}$BF$_4$INO$_5$, 724.1824, found, 724.1817.

N-(4-(2-(3,3-Dimethyl-1λ$^3$-benzo[d][1,2]iodaoxol-1 (3H)-yl)-1,1,2,2-tetrafluoroethoxy)phenethyl)-4-formyl-N-methylbenzamide (#) JV151-1

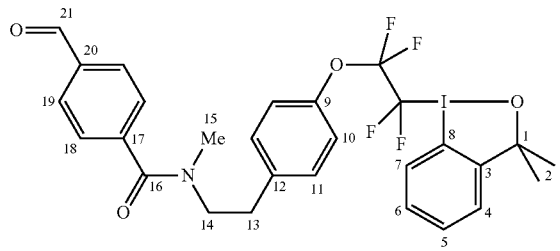

The title compound was prepared according to the general procedure starting from 4-formylbenzoic acid (0.12 mmol) using (i-Pr)$_2$EtN as the base. The reaction time was 3 h. The reaction mixture was directly concentrated on Celite, and the product was isolated by automated flash chromatography (12 g SiO$_2$ column, gradient elution from hexane to EtOAc) as a colourless oil.

Yield: 47 mg (73%); R$_f$=0.21 (EtOAc);

$^1$H NMR (500.13 MHz, CDCl$_3$): δ 1.50 (s, 6H, C(2)H$_3$), 2.79 and 3.01 (m, 2H, C(13)H$_2$), 2.81 and 3.17 (s, 3H, C(15)H$_3$), 3.46 and 3.79 (m, 2H, C(14)H$_2$), 6.93 and 7.31 (d, $^3J_{HH}$=8.4, 2H, C(11)H), 7.09 and 7.18 (d, $^3J_{HH}$=8.4, 2H, C(10)H), 7.13 and 7.44 (d, $^3J_{HH}$=8.0, 2H, C(18)H), 7.39 (m, 2H, C(4)H and C(6)H), 7.50 (m, 1H, C(5)H), 7.73 (m, 1H, C(7)H), 7.79 and 7.90 (d, $^3J_{HH}$=8.0, 2H, C(19)H), 10.0 and 10.03 (s, 1H, C(21)H);

$^{19}$F NMR (470.55 MHz, CDCl$_3$): δ−97.4 and −97.3 (bs, 2F, CF$_2$), −84.8 and −84.7 (bt, 2F, CF$_2$);

$^{13}$C {$^1$H} NMR (125.77 MHz, CDCl$_3$): δ 30.9 (s, C(2)H$_3$), 32.6 and 33.7 (s, C(13)H$_2$), 32.9 and 37.9 (s, C(15)H$_3$), 48.9 and 52.6 (s, C(14)H$_2$), 76.2 (bs, C(1)), 110.8 (m, C(8)), 111.2 and 111.3 (tt, $^1J_{CF}$=337, $^2J_{CF}$=38.0, CF$_2$), 117.2 (tt, $^1J_{CF}$=276, $^2J_{CF}$=27.0, CF$_2$), 121.8 and 122.1 (s, C(10)H), 127.0 and 127.4 (s, C(18)H), 127.5 (s, C(4)H or C(6)H), 129.1 (bm, C(7)), 129.5 (s, C(4)H or C(6)H), 129.6 and 129.8 (s, C(19)H), 130.1 (s, C(11)H), 130.5 (s, C(5)H), 136.3 and 137.3 (s, C(12)), 136.5 and 136.7 (s, C(20)), 141.9 and 142.1 (s, C(17)), 147.4 and 147.6 (m, C(9)), 149.8 (s, C(3)), 170.0 and 170.6 (s, C(16)), 191.5 (s, C(21)H);

HRMS (m/z, ESI$^+$): [M+H]$^+$ calcd. for C$_{28}$H$_{27}$F$_4$INO$_4$, 644.0915, found, 644.0926.

4-Cyano-N-(4-(2-(3,3-dimethyl-1λ$^3$-benzo[d][1,2] iodaoxol-1 (3H)-yl)-1,1,2,2-tetrafluoroethoxy)phenethyl)-N-methylbenzamide (#) JV153-2

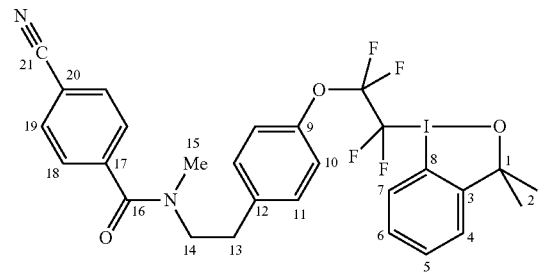 [SMILES: CN(CCc1ccc(OC(F)(F)C(F)(F)I2OC(C)(C)c3ccccc32)cc1)C(=O)c1ccc(C#N)cc1]

The title compound was prepared according to the general procedure starting from 4-cyanobenzoic acid (0.12 mmol) using (i-Pr)$_2$EtN as the base. The reaction time was 1.5 h. The reaction mixture was washed with buffer, aqueous NaHCO$_3$ and brine, concentrated on Celite, and the product was isolated by automated flash chromatography (12 g SiO$_2$ column, gradient elution from hexane to EtOAc) as a colourless oil.

Yield: 44 mg (69%); R$_f$=0.24 (EtOAc);

$^1$H NMR (400.13 MHz, CDCl$_3$): δ 1.50 (s, 6H, C(2)H$_3$), 2.77 and 3.00 (m, 2H, C(13)H$_2$), 2.79 and 3.16 (s, 3H, C(15)H$_3$), 3.44 and 3.78 (m, 2H, C(14)H$_2$), 6.94 and 7.29 (d, $^3J_{HH}$=8.1, 2H, C(11)H), 7.10 and 7.17 (d, $^3J_{HH}$=8.1, 2H, C(10)H), 7.01 and 7.37 (d, $^3J_{HH}$=7.6, 2H, C(18)H), 7.39 (m, 2H, C(4)H and C(6)H), 7.50 (m, 1H, C(5)H), 7.73 (m, 1H, C(7)H), 7.53 and 7.67 (d, $^3J_{HH}$=7.6, 2H, C(19)-H);

$^{19}$F NMR (376.46 MHz, CDCl$_3$): δ−97.7 and −97.6 (bs, 2F, CF$_2$), −84.8 and −84.7 (bt, 2F, CF$_2$);

$^{13}$C {$^1$H} NMR (100.62 MHz, CDCl$_3$): δ 30.9 (s, C(2)H$_3$), 32.6 and 33.6 (s, C(13)H$_2$), 32.9 and 37.9 (s, C(15)H$_3$), 48.9 and 52.5 (s, C(14)H$_2$), 76.4 (bs, C(1)), 110.9 (m, C(8)), 111.3 (m, CF$_2$), 113.0 and 113.3 (s, C(20)), 117.3 (m, CF$_2$), 118.0 (s, C(21)), 121.8 and 122.1 (s, C(10)H), 127.1 and 127.5 (s, C(18)H), 127.4 (s, C(4)H or C(6)H), 128.9 (bm, C(7)), 129.4 (s, C(4)H or C(6)H), 130.1 (s, C(11)H), 130.4 (s, C(5)H), 132.1 and 132.3 (s, C(19)H), 136.2 and 137.2 (s, C(12)), 140.5 and 140.7 (s, C(17)), 147.4 and 147.6 (m, C(9)), 149.8 (s, C(3)), 169.3 and 170.0 (s, C(16));

HRMS (m/z, ESI$^+$): [M+H]$^+$ calcd. for C$_{28}$H$_{26}$F$_4$IN$_2$O$_3$, 641.0919, found, 641.0923.

4-((4-(2-(3,3-Dimethyl-1λ³-benzo[d][1,2]iodaoxol-1(3H)-yl)-1,1,2,2-tetrafluoroethoxy)phenethyl)(methyl)carbamoyl)benzenesulfonyl fluoride (#) JV160-1

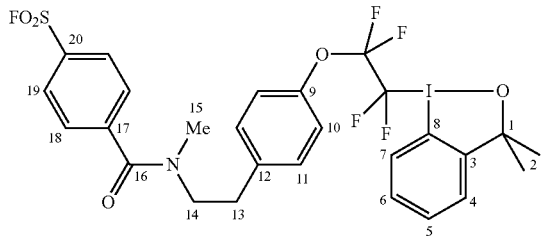

The title compound was prepared according to the general procedure starting from 4-(fluorosulfonyl)benzoic acid (0.12 mmol) using (i-Pr)$_2$EtN as the base. The reaction time was 1.5 h. The reaction mixture was directly concentrated on Celite, and the product was isolated by automated flash chromatography (12 g SiO$_2$ column, gradient elution from hexane to EtOAc) as a pale yellow oil.

Yield: 40 mg (57%); R$_f$=0.25 (EtOAc);

$^1$H NMR (500.13 MHz, CDCl$_3$): δ 1.50 (s, 6H, C(2)H$_3$), 2.81 and 3.02 (m, 2H, C(13)H$_2$), 2.81 and 3.18 (s, 3H, C(15)H$_3$), 3.46 and 3.80 (m, 2H, C(14)H$_2$), 6.95 and 7.30 (d, $^3J_{HH}$=8.4, 2H, C(11)H), 7.12 and 7.18 (d, $^3J_{HH}$=8.4, 2H, C(10)H), 7.12 and 7.51 (m, 2H, C(18)H), 7.40 (m, 2H, C(4)H and C(6)H), 7.50 (m, 1H, C(5)H), 7.74 (m, 1H, C(7)H), 7.89 and 8.04 (d, $^3J_{HH}$=8.0, 2H, C(19)H);

$^{19}$F NMR (470.58 MHz, CDCl$_3$): δ −97.7 and −97.6 (bs, 2F, CF$_2$), −84.8 and −84.7 (bt, 2F, CF$_2$), 65.5 and 65.5 (bs, 1F, SO$_2$F);

$^{13}$C {$^1$H} NMR (125.77 MHz, CDCl$_3$): δ 30.8 (s, C(2)H$_3$), 32.5 and 33.5 (s, C(13)H$_2$), 32.9 and 37.8 (s, C(15)H$_3$), 48.9 and 52.5 (s, C(14)H$_2$), 76.4 (bm, C(1)), 110.8 (m, C(8)), 111.3 (m, CF$_2$), 117.2 (m, CF$_2$), 121.8 and 122.2 (s, C(10)H), 127.6 and 127.9 (s, C(18)H), 127.4 (bs, C(4)H or C(6)H), 128.9 (bm, C(7)), 129.5 (bs, C(4)H or C(6)H), 130.1 and 130.2 (s, C(11)H), 130.4 (bs, C(5)H), 128.5 and 128.8 (s, C(19)H), 133.5 and 133.7 (d, $^2J_{CF}$=25.3, C(20)), 136.1 and 137.0 (s, C(12)), 143.3 and 143.5 (s, C(17)), 147.4 and 147.7 (m, C(9)), 149.8 (bs, C(3)), 168.7 and 169.3 (s, C(16));

HRMS (m/z, ESI$^+$): [M+H]$^+$ calcd. for C$_{27}$H$_{26}$F$_5$INO$_5$S, 698.0491, found, 698.0473.

N-(4-(2-(3,3-Dimethyl-1λ³-benzo[d][1,2]iodaoxol-1(3H)-yl)-1,1,2,2-tetrafluoroethoxy)phenethyl)-4-ethynyl-N-methylbenzamide (#) JV172-1

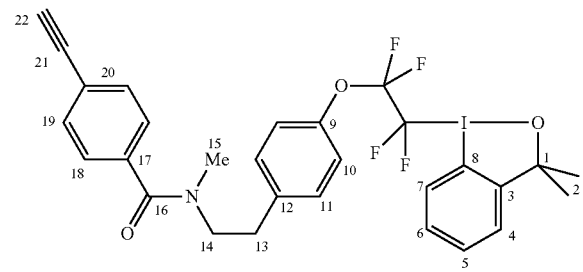 [SMILES: C#Cc1ccc(C(=O)N(C)CCc2ccc(OC(F)(F)C(F)(F)I3OC(C)(C)c4ccccc43)cc2)cc1]

The title compound was prepared according to the general procedure starting from 4-ethynylbenzoic acid (0.12 mmol) using (i-Pr)$_2$EtN as the base. The reaction time was 2 h. The reaction mixture was washed with buffer, aqueous NaHCO$_3$ and brine, concentrated on Celite, and the product was isolated by automated flash chromatography (12 g SiO$_2$ column, gradient elution from hexane to EtOAc) as a yellow waxy oil.

Yield: 47 mg (74%); R$_f$=0.38 (EtOAc);

$^1$H NMR (500.13 MHz, CDCl$_3$): δ 1.50 (s, 6H, C(2)H$_3$), 2.78 and 3.00 (m, 2H, C(13)H$_2$), 2.82 and 3.14 (s, 3H, C(15)H$_3$), 3.13 (s, 1H, C(22)H), 3.47 and 3.75 (m, 2H, C(14)H$_2$), 6.95 and 7.30 (bm, 2H, C(11)H), 6.98 and 7.27 (bm, 2H, C(18)H), 7.09 and 7.16 (bm, 2H, C(10)H), 7.39 (m, 2H, C(4)H and C(6)H), 7.41 and 7.49 (bm, 2H, C(19)H), 7.50 (m, 1H, C(5)H), 7.74 (m, 1H, C(7)H);

$^{19}$F NMR (470.55 MHz, CDCl$_3$): δ −97.6 (bs, 2F, CF$_2$), −84.8 and −84.7 (bs, 2F, CF$_2$);

$^{13}$C {$^1$H} NMR (125.77 MHz, CDCl$_3$): δ 30.9 (s, C(2)H$_3$), 32.7 and 33.8 (s, C(13)H$_2$), 33.0 and 38.1 (s, C(15)H$_3$), 49.1 and 52.7 (s, C(14)H$_2$), 76.3 (bs, C(1)), 78.5 (s, C(22)H), 82.8 (s, C(21)), 110.9 (bm, C(8)), 111.4 (m, CF$_2$), 117.2 (m, CF$_2$), 121.7 and 122.0 (s, C(10)H), 123.1 and 123.4 (s, C(20)), 126.4 and 126.9 (s, C(18)H), 127.4 (s, C(4)H or C(6)H), 128.9 (m, C(7)), 129.4 (s, C(4)H or C(6)H), 130.1 (s, C(11)H), 130.3 (s, C(5)H), 132.0 and 132.1 (s, C(19)H), 136.5 and 136.6 (s, C(17)), 136.5 and 137.5 (s, C(12)), 147.4 and 147.5 (m, C(9)), 149.8 (s, C(3)), 170.5 and 171.3 (s, C(16));

HRMS (m/z, ESI$^+$): [M+H]$^+$ calcd. for C$_{29}$H$_{27}$F$_4$INO$_3$, 640.0966, found, 640.0969.

N-(4-(2-(3,3-Dimethyl-1λ³-benzo[d][1,2]iodaoxol-1(3H)-yl)-1,1,2,2-tetrafluoroethoxy)phenethyl)-N-methyl-4-((trimethylsilyl)ethynyl)benzamide (#) JV164-1

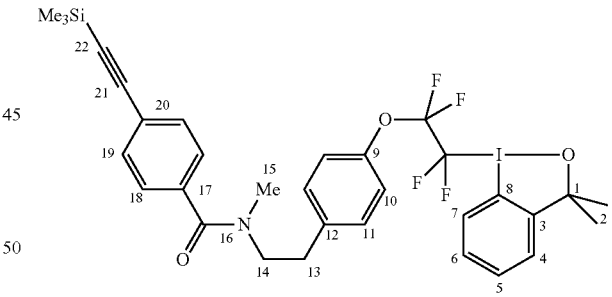

The title compound was prepared according to the general procedure starting from 4-[(Trimethylsilyl)ethynyl]benzoic acid (0.12 mmol) using (i-Pr)$_2$EtN as the base. The reaction time was 2 h. The reaction mixture was washed with buffer, aqueous NaHCO$_3$ and brine, concentrated on Celite, and the product was isolated by automated flash chromatography (12 g SiO$_2$ column, gradient elution from hexane to EtOAc) as a colourless oil.

Yield: 60 mg (84%); R$_f$=0.38 (EtOAc);

$^1$H NMR (500.13 MHz, CDCl$_3$): δ 0.25 (s, 9H, Si(CH$_3$)$_3$), 1.49 (s, 6H, C(2)H$_3$), 2.77 and 2.98 (m, 2H, C(13)H$_2$), 2.80 and 3.12 (s, 3H, C(15)H$_3$), 3.45 and 3.74 (m, 2H, C(14)H$_2$), 6.94 and 7.29 (bm, 2H, C(11)H), 6.97 and 7.24 (bm, 2H, C(18)H), 7.08 and 7.15 (bm, 2H, C(10)H), 7.38 and 7.46

(bm, 2H, C(19)H), 7.39 (m, 2H, C(4)H and C(6)H), 7.49 (m, 1H, C(5)H), 7.73 (m, 1H, C(7)H);

$^{19}$F NMR (470.55 MHz, CDCl$_3$): δ –97.6 (bs, 2F, CF$_2$), –84.8 and –84.7 (bs, 2F, CF$_2$);

$^{13}$C {$^1$H} NMR (125.77 MHz, CDCl$_3$): δ –0.2 (s, Si(CH$_3$)$_3$), 30.9 (s, C(2)H$_3$), 32.6 and 33.8 (s, C(13)H$_2$), 32.9 and 38.1 (s, C(15)H$_3$), 49.1 and 52.6 (s, C(14)H$_2$), 76.3 (bs, C(1)), 95.8 (bs, C(22)), 104.1 (s, C(21)), 110.9 (bm, C(8)), 111.4 (tt, $^1J_{CF}$=338, $^2J_{CF}$=39.2, CF$_2$), 117.2 (tt, $^1J_{CF}$=277, $^2J_{CF}$=26.0, CF$_2$), 121.7 and 121.9 (s, C(10)H), 124.2 and 124.4 (s, C(20)), 126.4 and 126.8 (s, C(18)H), 127.4 (s, C(4)H or C(6)H), 128.9 (bm, C(7)), 129.4 (s, C(4)H or C(6)H), 130.1 (s, C(11)H), 130.3 (s, C(5)H), 131.8 (s, C(19)H), 136.1 (s, C(17)), 136.4 and 137.5 (s, C(12)), 147.3 and 147.5 (m, C(9)), 149.8 (s, C(3)), 170.6 and 171.4 (s, C(16));

HRMS (m/z, ESI$^+$): [M+H]$^+$ calcd. for C$_{32}$H$_{35}$F$_4$INO$_3$Si, 712.1362, found, 712.1351.

N-(4-(2-(3,3-Dimethyl-1λ$^3$-benzo[d][1,2]iodaoxol-1 (3H)-yl)-1,1,2,2-tetrafluoroethoxy)phenethyl)-N-methyl-2-oxo-2H-chromene-3-carboxamide (#) JV144-1

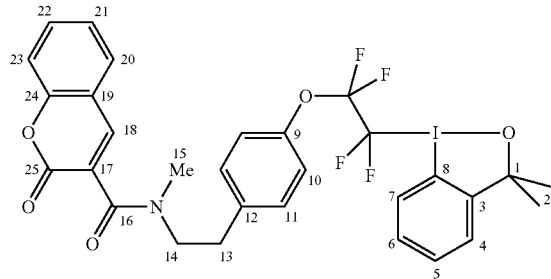 [SMILES: CN(CCc1ccc(OC(F)(F)C(F)(F)I2OC(C)(C)c3ccccc32)cc1)C(=O)c1cc2ccccc2oc1=O]

The title compound was prepared according to the general procedure starting from coumarin-3-carboxylic acid (0.12 mmol) using Et$_3$N as the base. The reaction time was 1 h. The reaction mixture was directly concentrated on Celite, and the product was isolated by automated flash chromatography (12 g SiO$_2$ column, gradient elution from hexane to EtOAc) as a colourless oil.

Yield: 57 mg (83%); R$_f$=0.36 (EtOAc);

$^1$H NMR (400.13 MHz, CDCl$_3$): δ 1.49 (s, 6H, C(2)H$_3$), 2.89 and 2.98 (m, 2H, C(13)H$_2$), 2.89 and 3.15 (s, 3H, C(15)H$_3$), 3.49 and 3.73 (m, 2H, C(14)H$_2$), 7.00 and 7.79 (s, 1H, C(18)H), 7.05 and 7.16 (m, 2H, C(10)H), 7.05 and 7.32 (m, 2H, C(11)H), 7.27 and 7.30 (m, 1H, C(21)H), 7.30 and 7.33 (m, 1H, C(23)H), 7.30 and 7.51 (m, 1H, C(20)H), 7.39 (m, 2H, C(4)H and C(6)H), 7.50 (m, 1H, C(5)-H) and 7.53 and 7.57 (m, 1H, C(22)-H), 7.74 (m, 1H, C(7)H);

$^{19}$F NMR (376.46 MHz, CDCl$_3$): δ –97.5 and –97.3 (bs, 2F, CF$_2$), –84.7 and –84.6 (bt, 2F, CF$_2$);

$^{13}$C {$^1$H} NMR (100.62 MHz, CDCl$_3$): δ 30.8 (s, C(2)H$_3$), 32.7 and 33.4 (s, C(13)H$_2$), 32.8 and 37.0 (s, C(15)H$_3$), 49.5 and 52.2 (s, C(14)H$_2$), 76.3 and 76.2 (bm, C(1)), 110.7 (m, C(8)), 111.2 and 111.3 (tt, $^1J_{CF}$=337, $^2J_{CF}$=37.8, CF$_2$), 117.2 and 117.3 (tt, $^1J_{CF}$=277, $^2J_{CF}$=25.8, CF$_2$), 116.6 and 116.7 (s, C(23)H), 118.1 and 118.2 (s, C(19)H), 121.6 and 121.7 (s, C(10)H), 124.8 and 124.9 (s, C(21)H), 125.1 and 125.8 (s, C(17)), 127.4 and 127.5 (bs, C(4)H or C(6)H), 128.4 and 128.5 (s, C(20)H), 129.0 (bm, C(7)), 129.5 (s, C(4)H or C(6)H), 130.2 and 130.3 (s, C(11)H), 130.4 (s, C(5)H), 132.6 and 132.7 (s, C(22)), 136.7 and 137.5 (s, C(12)), 142.5 (s, C(18)H), 147.3 and 147.5 (m, C(9)), 149.8 (s, C(3)), 153.7 and 154.0 (s, C(24)), 157.7 and 158.0 (s, C(25)), 164.9 and 165.0 (s, C(16)); HRMS (m/z, ESI$^+$): [M+H]$^+$ calcd. for C$_{30}$H$_{27}$F$_4$INO$_5$, 684.0865, found, 684.0854.

N-(4-(2-(3,3-dimethyl-1λ$^3$-benzo[d][1,2]iodaoxol-1 (3H)-yl)-1,1,2,2-tetrafluoroethoxy)phenethyl)-2-(6-methoxy-3-oxo-3H-xanthen-9-yl)-N-methylbenzamide (#) JV154-3

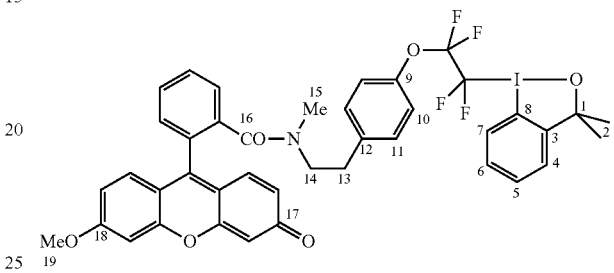

The title compound was prepared according to the general procedure starting from methylfluorescein (0.12 mmol) using (i-Pr)$_2$EtN as the base. The reaction time was 3.5 h. The reaction mixture was washed with buffer, aqueous NaHCO$_3$ (2×) and brine, concentrated on Celite, and the product was isolated by automated flash chromatography (12 g SiO$_2$ column, gradient elution from DCM to MeOH) as an orange solid.

Yield: 20 mg (24%); m.p. 88–90° C.; R$_f$=0.24 (EtOAc: MeOH 10:1);

$^1$H NMR (500.13 MHz, CD$_3$OD): δ 1.49 and 1.50 (s, 6H, C(2)H$_3$), 2.46 and 2.81 (m, 2H, C(13)H$_2$), 2.72 and 2.83 (s, 3H, C(15)H$_3$), 3.20 and 3.43 (m, 2H, C(14)H$_2$), 3.77 and 3.96 (s, 3H, C(19)H$_3$), 6.45-8.00 (m, 10H, C$_{Ar}$H),$^1$ 7.09 and 7.16 (m, 2H, C(11)H), 7.09 and 7.22 (m, 2H, C(10)H), 7.49 (m, 1H, C(6)H), 7.54 (m, 1H, C(4)H), 7.59 (m, 1H, C(5)H), 7.78 (m, 1H, C(7)H);

$^1$ These signals could not be assigned due to extensive overlap and the presence of rotamers.

$^{19}$F NMR (470.55 MHz, CD$_3$OD): δ –97.3 and –97.2 (bt, 2F, CF$_2$), –85.4 and –85.3 (bt, 2F, CF$_2$);

$^{13}$C NMR (125.77 MHz, CD$_3$OD): δ 31.0 (s, C(2)H$_3$), 32.9 and 34.2 (s, C(13)H$_2$), 32.7 and 38.4 (s, C(15)H$_3$), 49.6 and 54.1 (s, C(14)H$_2$), 56.1 and 57.0 (s, C(19)H$_3$), 77.5 (bm, C(1)), 101.4 (s, C$_{Ar}$H), 105.7 (s, C$_{Ar}$H) 111.2 (m, C(8)), 112.4 (m, CF$_2$), 115.3 and 115.4 (s, C$_{Ar}$H), 115.9 (s, C$_{Ar}$), 118.5 (s, C$_{Ar}$), 118.6 and 118.8 (m, CF$_2$), 122.7 and 123.1 and 123.2 (s, C(10)H), 128.6 and 128.7 (s, C$_{Ar}$H), 129.1 (s, C(4)H), 129.2 and 129.4 (s, C$_{Ar}$H), 130.2 (tm, J$_{CF}$=4.5, 1H, C(7)H), 130.8 and 130.9 (s, C$_{Ar}$H), 131.0 (s, C(6)H), 131.2 and 131.9 (s, C(11)H), 131.6 (s, C$_{Ar}$H), 131.8 (s, C$_{Ar}$H), 131.9 (s, C$_{Ar}$H), 132.1 (s, C(5)H), 132.2 (s, C$_{Ar}$), 133.3 and 133.3 (s, C$_{Ar}$H), 137.2 and 137.5 (s, C$_{Ar}$), 138.8 and 139.0 (s, C(12)), 148.5 and 148.8 and 149.0 (s, C(9)), 151.1 and 151.1 (s, C(3)), 152.7 and 153.1 (s, C$_{Ar}$), 156.4 (s, C$_{Ar}$), 161.2 (s, C$_{Ar}$), 167.2 (s, C(18)), 170.6 and 171.2 (s, C(16)), 187.2 and 187.3 (s, C(17));

HRMS (m/z, ESI/MALDI): [M+H]$^+$ calcd. for C$_{41}$H$_{35}$F$_4$INO$_6$, 840.1440; found, 840.1438.

(1S)—N-(4-(2-(3,3-Dimethyl-1λ³-benzo[d][1,2]
iodaoxol-1(3H)-yl)-1,1,2,2-tetrafluoroethoxy)phen-
ethyl)-N,4,7,7-tetramethyl-3-oxo-2-oxabicyclo
[2.2.1]heptane-1-carboxamide (#) JV142-1

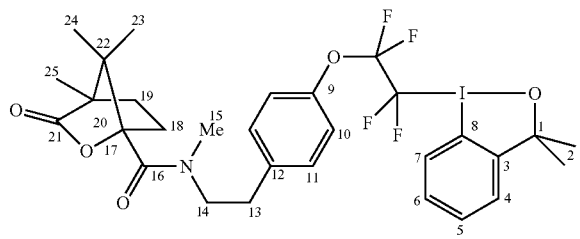 [SMILES: CN(CCc1ccc(OC(F)(F)C(F)(F)I2OC(C)(C)c3ccccc32)cc1)C(=O)C12CCC(C)(C(=O)O1)C2(C)C]

The title compound was prepared according to the general procedure starting from (1S)-(−)-camphanic acid (0.12 mmol) using Et₃N as the base. The reaction time was 1.5 h. The reaction mixture was directly concentrated on Celite, and the product was isolated by automated flash chromatography (12 g SiO₂ column, gradient elution from hexane to EtOAc) as a pale yellow oil.

Yield: 49 mg (71%); $R_f$=0.45 (EtOAc);

¹H NMR (400.13 MHz, CDCl₃): δ 0.89 and 0.96 (s, 3H, C(23)H₃ or C(24)H₃), 1.07 and 1.09 (s, 3H, C(25)H₃), 1.11 and 1.16 (s, 3H, C(23)H₃ Or C(24)H₃), 1.49 (s, 6H, C(2)H₃), 1.60-1.70 and 1.78-2.04 and 2.26-2.37 (m, 4H, C(18)H₂ and C(19)H₂), 2.86 and 2.93 (m, 2H, C(13)H₂), 3.00 and 3.14 (s, 3H, C(15)H₃), 3.54 and 3.60 and 3.68 and 3.77 (m, 2H, C(14)H₂),[2] 7.11 and 7.13 (m, 2H, C(10)H), 7.23 and 7.30 (m, 2H, C(11)H), 7.38 (m, 2H, C(4)H and C(6)H), 7.49 (m, 1H, C(5)H), 7.73 (m, 1H, C(7)H);

¹⁹F NMR (376.46 MHz, CDCl₃): δ −97.5 (bs, 2F, CF₂), −84.8 and −84.7 (bt, 2F, CF₂);

¹³C {¹H} NMR (125.77 MHz, CDCl₃): δ 9.6 (C(25)H₃), 16.6 and 16.7 (s, C(23)H₃ or C(24)H₃), 17.6 and 17.8 (s, C(23)H₃ or C(24)H₃), 29.2 and 29.3 (s, C(18)H₃ or C(19)H₃), 30.8 (s, C(2)H₃), 30.9 and 31.6 (s, C(18)H₃ or C(19)H₃), 32.5 and 35.1 (s, C(13)H₂), 35.3 and 36.5 (s, C(15)H₃), 50.8 and 52.0 (s, C(14)H₂), 53.8 and 53.8 (s, C(22) or C(20)), 55.1 and 55.3 (s, C(22) or C(20)), 76.2 (bs, C(1)), 92.7 and 92.8 (s, C(17)), 110.7 (m, C(8)), 111.3 (tt, $^1J_{CF}$=337, $^2J_{CF}$=38.2, CF₂), 117.1 (tt, $^1J_{CF}$=277, $^2J_{CF}$=26.2, CF₂), 121.6 and 121.8 (s, C(10)H), 127.5 (s, C(4)H or C(6)H), 129.1 (t, $J_{CF}$=5.3, C(7)), 129.5 (s, C(4)H or C(6)H), 130.1 and 130.4 (s, C(11)H), 130.4 (s, C(5)H), 137.0 and 137.4 (bs, C(12)), 147.3 and 147.4 (m, C(9)), 149.8 (s, C(3)), 166.7 and 167.2 (s, C(16)), 178.3 and 178.6 (s, C(21));

[2] The signals are diastereomers of rotamers.

HRMS (m/z, ESI⁺): [M+H]⁺ calcd. for C₃₀H₃₅F₄INO₅, 692.1491, found, 692.1481.

N-(4-(2-(3,3-dimethyl-1λ³-benzo[d][1,2]iodaoxol-1
(3H)-yl)-1,1,2,2-tetrafluoroethoxy)phenethyl)-N-
methyl-5-((3aS,4S,6aR)-2-oxohexahydro-1H-thieno
[3,4-d]imidazol-4-yl)pentanamide (#) JV132-7

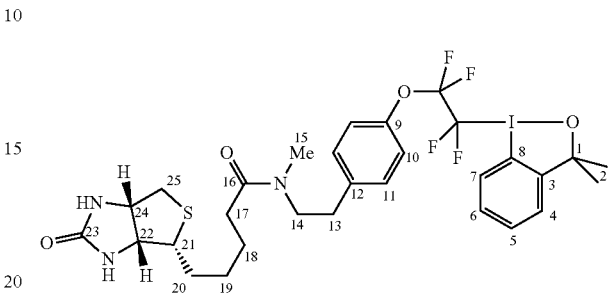

The title compound was prepared according to the general procedure starting from biotin (0.11 mmol, only 1.1 equiv.) using (i-Pr)₂EtN as the base. The coupling reaction was carried out in DMF for 3 h. The reaction mixture was diluted with chloroform, washed with brine, concentrated on Celite, and the product was isolated by automated flash chromatography (12 g SiO₂ column, gradient elution from DCM to DCM:MeOH 4:1) as a colourless waxy oil.

Yield: 31 mg (42%); $R_f$=0.46 (DCM:MeOH 9:1);

¹H NMR (500.26 MHz, CDCl₃): δ 1.48 (s, 6H, C(2)H₃), 1.30-1.77 (m, 6H, C(18)H₂, C(19)H₂, C(20)H₂), 2.07 and 2.29 (m, 2H, C(17)H₂), 2.72 and 2.87 (m, 2H, C(25)H₂), 2.81 and 2.83 (m, 2H, C(13)H₂), 2.87 and 2.92 (s, 3H, C(15)H₃), 3.14 (m, 1H, C(21)H), 3.49 and 3.55 (m, 2H, C(14)H₂), 4.28 (m, 1H, C(22)H), 4.47 (m, 1H, C(24)H), 5.61-6.07 (s, 2H, 2×NHbiotin), 7.11 and 7.15 (m, 2H, C(10)H), 7.16 and 7.21 (m, 2H, C(11)H), 7.37 (m, 2H, C(4)H and C(6)H), 7.49 (m, 1H, C(5)H), 7.72 (m, 1H, C(7)H);

¹⁹F NMR (470.67 MHz, CDCl₃): δ −97.5 (bs, 2F, CF₂), −84.7 and −84.7 (bt, $^3J_{FF}$=4.4, 2F, CF₂);

¹³C {¹H} NMR (125.80 MHz, CDCl₃): δ 24.7-25.0 and 28.2-28.4 (s, C(18)H₂, C(19)H₂, C(20)H₂), 30.9 (s, C(2)H₃), 32.2 and 33.0 (s, C(17)H₂), 33.0 and 34.2 (s, C(13)H₃), 33.5 and 36.0 (s, C(15)H₃), 40.4 and 40.5 (s, C(25)H₂), 49.6 and 51.4 (s, C(14)H₂), 55.4 (s, C(21)H), 60.1 (s, C(24)H), 61.8 and 61.8 (s, C(22)H), 76.3 (bs, C(1)), 110.9 (m, C(8)), 111.3 and 111.4 (tt, $^1J_{CF}$=338, $^2J_{CF}$=38.0, CF₂), 117.2 (tt, $^1J_{CF}$=277, $^2J_{CF}$=27.0, CF₂), 121.5 and 121.9 (s, C(10)H), 127.4 (bm, C(4) or C(6)), 129.0 (bm, C(7)), 129.4 (bm, C(4) or C(6)), 130.0 and 130.0 (s, C(11)H), 130.3 (bm, C(5)), 136.9 and 137.8 (s, C(12)), 147.2 and 147.5 (s, C(9)), 149.8 (m, C(3)), 163.7 (bs, C(23)), 172.8 and 172.8 (s, C(16));

HRMS (m/z, ESI/MALDI): [M+H]⁺ calcd. for C₃₀H₃₇F₄IN₃O₄S, 738.1480, found, 738.1482.

14-Azido-N-(4-(2-(3,3-dimethyl-1λ³-benzo[d][1,2]iodaoxol-1 (3H)-yl)-1,1,2,2-tetrafluoroethoxy)phenethyl)-N-methyl-3,6,9,12-tetraoxatetradecanamide (#) JV128-5

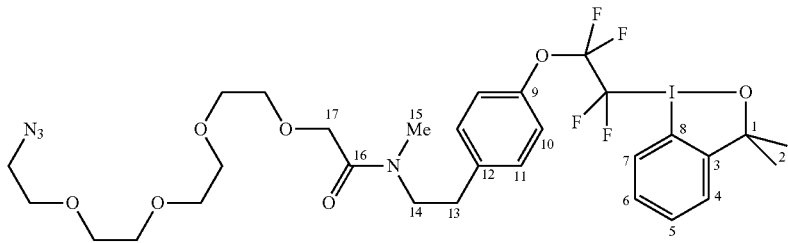 [SMILES: CN(CCc1ccc(OC(F)(F)C(F)(F)I2OC(C)(C)c3ccccc32)cc1)C(=O)COCCOCCOCCOCCN=[N+]=[N-]]

The title compound was prepared according to the general procedure starting from N₃-PEG acid (0.28 mmol) using (i-Pr)₂EtN as the base. The reaction time was 1.5 h. The reaction mixture was washed with buffer (2×), aqueous NaHCO₃ (2×) and brine, concentrated on Celite, and the product was isolated by automated flash chromatography (24 g SiO₂ column, gradient elution from hexane to EtOAc:MeOH 9:1) as a yellowish oil.

Yield: 136 mg (77%); $R_f$=0.13 (EtOAc:MeOH 10:1);

$^1$H NMR (500.13 MHz, CDCl₃): δ 1.47 (s, 6H, C(2)H₃), 2.84 and 2.86 (m, 2H, C(13)H₂), 2.87 and 2.94 (s, 3H, C(15)H₃), 3.35 (m, 2H, CH₂), 3.51 and 3.55 (m, 2H, C(14)H₂), 3.58-3.65 (m, 14H, 7×CH₂), 3.96 and 4.15 (s, 2H, C(17)H₂), 7.10 and 7.12 (d, $^3J_{HH}$=8.5, 2H, C(10)H), 7.18 and 7.21 (d, $^3J_{HH}$=8.5, 2H, C(11)H), 7.37 (m, 2H, C(4)H and C(6)H), 7.48 (m, 1H, C(5)H), 7.71 (m, 1H, C(7)H);

$^{19}$F NMR (470.55 MHz, CDCl₃): δ−97.7 and −97.6 (bs, 2F, CF₂), −84.8 and −84.8 (bt, 2F, CF₂);

$^{13}$C {$^1$H} NMR (125.77 MHz, CDCl₃): δ 30.8 (s, C(2)H₃), 32.8 and 34.0 (s, C(13)H₂), 33.4 and 34.9 (s, C(15)H₃), 49.6 and 50.7 (s, C(14)H₂), 50.6 (s, CH₂), 69.9 and 69.9 (s, CH₂), 70.2 and 70.3 (s, C(17)H₂), 70.4-70.6 (s, 6×CH₂), 76.3 (bs, C(1)), 110.9 (m, C(8)), 111.3 and 111.3 (tt, $^1J_{CF}$=337, $^2J_{CF}$=38.2, CF₂), 117.2 (tt, $^1J_{CF}$=277, $^2J_{CF}$=26.0, CF₂), 121.5 and 121.8 (s, C(10)H), 127.3 (s, C(4)H or C(6)H), 128.8 (bm, C(7)), 129.3 (s, C(4)H or C(6)H), 130.0 and 130.0 (s, C(11)H), 130.3 (s, C(5)H), 136.9 and 137.5 (s, C(12)), 147.2 and 147.4 (m, C(9)), 149.8 (s, C(3)), 169.0 and 169.1 (s, C(16));

HRMS (m/z, ESI⁺): [M+H]⁺ calcd. for C₃₀H₄₀F₄IN₄O₇, 771.1872, found, 771.1862.

N-(4-(2-(3,3-dimethyl-1λ³-benzo[d][1,2]iodaoxol-1 (3H)-yl)-1,1,2,2-tetrafluoroethoxy)phenethyl)-N-methyl-3,6,9,12,15-pentaoxaoctadec-17-ynamide (#) JV171-1

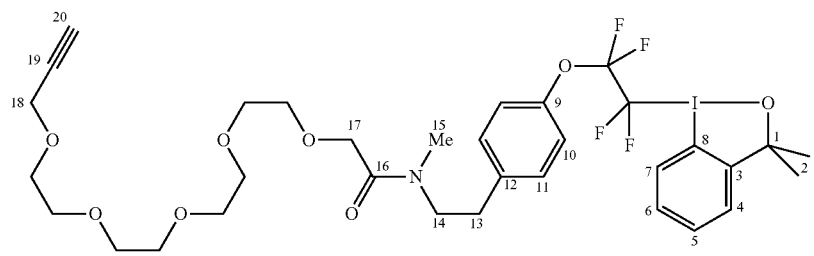 [SMILES: C#CCOCCOCCOCCOCCOCC(=O)N(C)CCc1ccc(OC(F)(F)C(F)(F)I2OC(C)(C)c3ccccc32)cc1]

The title compound was prepared according to the general procedure starting from propargyl-PEG acid (0.24 mmol) using (i-Pr)$_2$EtN as the base. The reaction time was 3 h. The reaction mixture was washed with buffer (2×), aqueous NaHCO$_3$ (2×) and brine, concentrated on Celite, and the product was isolated by automated flash chromatography (24 g SiO$_2$ column, gradient elution from hexane to EtOAc:MeOH 9:1) as a yellowish oil.

Yield: 102 mg (65%); R$_f$=0.07 (EtOAc:MeOH 10:1);

$^1$H NMR (500.13 MHz, CDCl$_3$): δ 1.49 (s, 6H, C(2)H$_3$), 2.42 (bt, 1H, C(20)H), 2.85 (m, 2H, C(13)H$_2$), 2.89 and 2.95 (s, 3H, C(15)H$_3$), 3.52 and 3.56 (m, 2H, C(14)H$_2$), 3.58-3.68 (m, 16H, 8×CH$_2$), 3.98 and 4.17 (s, 2H, C(17)H$_2$), 4.18 (t, $J_{HH}$=2.5, 2H, C(18)H$_2$), 7.12 and 7.14 (m, 2H, C(10)H), 7.19 and 7.23 (m, 2H, C(11)-H), 7.39 (m, 2H, C(4)H and C(6)H), 7.50 (m, 1H, C(5)-H), 7.73 (m, 1H, C(7)H);

$^{19}$F NMR (470.55 MHz, CDCl$_3$): δ −97.5 (bs, 2F, CF$_2$), −84.8 and −84.8 (bt, 2F, CF$_2$); $^{13}$C {$^1$H} NMR (125.77 MHz, CDCl$_3$): δ 30.9 (s, C(2)H$_3$), 32.8 and 34.1 (s, C(13)H$_2$), 33.4 and 35.0 (s, C(15)H$_3$), 49.7 and 50.7 (s, C(14)H$_2$), 58.4 (s, C(18)H$_2$), 69.1 (s, CH$_2$), 70.3-70.6 (s, 8×CH$_2$), 74.5 (s, C(20)H), 76.3 (bs, C(1)), 79.6 (s, C(19)), 110.8 (m, C(8)), 111.4 (tt, $^1J_{CF}$=337, $^2J_{CF}$=38.0, CF$_2$), 117.2 (tt, $^1J_{CF}$=277, $^2J_{CF}$=26.0, CF$_2$), 121.6 and 121.9 (s, C(10)H), 127.4 (s, C(4)H or C(6)H), 129.0 (bm, C(7)), 129.4 (s, C(4)H or C(6)H), 130.0 and 130.1 (s, C(11)H), 130.4 (s, C(5)H), 137.0 and 137.6 (s, C(12)H), 147.2 and 147.5 (m, C(9)), 149.8 (s, C(3)), 169.0 and 169.2 (s, C(16));

HRMS (m/z, ESI$^+$): [M+H]$^+$ calcd. for C$_{33}$H$_{43}$F$_4$INO$_8$, 784.1964, found, 784.1956.

N-(4-(2-(3,3-Dimethyl-1λ$^3$-benzo[d][1,2]iodaoxol-1 (3H)-yl)-1,1,2,2-tetrafluoroethoxy)phenethyl)-N-methyl-1-(pyren-1-yl)-2,5,8,11,14-pentaoxahexadecan-16-amide (#) JV124-4B

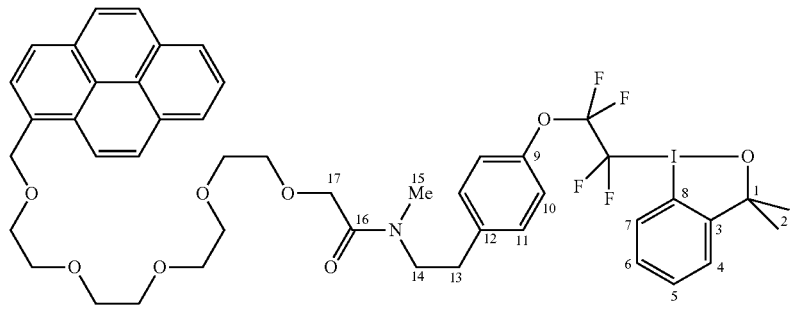 [SMILES: CN(CCc1ccc(OC(F)(F)C(F)(F)I2OC(C)(C)c3ccccc32)cc1)C(=O)COCCOCCOCCOCCOCc1ccc2ccc3cccc4ccc1c2c34]

The title compound was prepared according to the general procedure starting from pyrene-PEG acid (0.12 mmol) using (i-Pr)$_2$EtN as the base. The reaction time was 4.5 h. The reaction mixture was washed with buffer, aqueous NaHCO$_3$ and brine, concentrated on Celite, and the product was isolated by automated flash chromatography (12 g SiO$_2$ column, gradient elution from DCM to MeOH) as a yellowish oil.

Yield: 43 mg (48%); R$_f$=0.58 (DCM:MeOH 9:1);

$^1$H NMR (400.13 MHz, CDCl$_3$): δ 1.50 (s, 6H, C(2)H$_3$), 2.77 and 2.79 (m, 2H, C(13)H$_2$), 2.80 and 2.90 (s, 3H, C(15)H$_3$), 3.43 and 3.51 (m, 2H, C(14)H$_2$), 3.56-3.76 (m, 16H, 8×CH$_2$), 3.92 and 4.11 (s, 2H, C(17)H$_2$), 5.27 (m, 2H, OCH$_2$-pyrene), 7.10 (m, 2H, C(10)H), 7.11 and 7.18 (m, 2H, C(11)H), 7.37 (m, 2H, C(4)H and C(6)H), 7.48 (m, 1H, C(5)H), 7.74 (m, 1H, C(7)H), 7.97-8.04 (m, 4H, C$_{Ar}$H), 8.11-8.19 (m, 4H, C$_{Ar}$H), 8.39 (m, 1H, C$_{Ar}$H);

$^{19}$F NMR (376.46 MHz, CDCl$_3$): δ −97.3 (bs, 2F, CF$_2$), −84.7 and −84.7 (bt, 2F, CF$_2$);

$^{13}$C {$^1$H} NMR (100.62 MHz, CDCl$_3$): δ 30.9 (s, C(2)H$_3$), 32.8 and 34.0 (s, C(13)H$_2$), 33.4 and 34.8 (s, C(15)H$_3$), 49.6 and 50.6 (s, C(14)H$_2$), 69.5 (s, CH$_2$), 70.2-70.7 (s, 8×CH$_2$), 71.8 (s, OCH$_2$-pyrene), 76.2 and 76.3 (s, C(1)), 110.9 (m, C(8)), 111.3 and 111.4 (tt, $^1J_{CF}$=337, $^2J_{CF}$=37.0, CF$_2$), 117.2 (tt, $^1J_{CF}$=277, $^2J_{CF}$=26.0, CF$_2$), 121.8 (s, C(10)H), 123.5 (s, C$_{Ar}$H), 124.4 (s, C$_{Ar}$H), 124.6 (s, C$_{Ar}$), 124.9 (s, C$_{Ar}$), 125.1 (s, 2×C$_{Ar}$H), 125.9 (s, C$_{Ar}$H), 127.0 (s, C$_{Ar}$H), 127.3 (s, 2×C$_{Ar}$H), 127.4 (s, C(4)H or C(6)H), 127.6 (s, C$_{Ar}$H), 129.1 (bm, C(7)), 129.3 (s, C$_{Ar}$), 129.4 (bs, C(4)H or C(6)H), 130.0 (s, C(11)H), 130.4 (bs, C(5)H), 130.8 (s, C$_{Ar}$), 131.2 (s, 2×C$_{Ar}$), 131.4 (s, C$_{Ar}$), 136.9 and 137.5 (s, C(12)), 147.2 and 147.4 (m, C(9)), 149.7 (s, C(3)), 169.0 and 169.1 (s, C(16));

HRMS (m/z, ESI$^+$): [M+H]$^+$ calcd. for C$_{47}$H$_{51}$F$_4$INO$_8$, 960.2590, found, 960.2578.

N-(4-(2-(3,3-dimethyl-1λ³-benzo[d][1,2]iodaoxol-1 (3H)-yl)-1,1,2,2-tetrafluoroethoxy)phenethyl)-N-methyl-14-(4-((pyren-4-ylmethoxy)methyl)-1H-1,2,3-triazol-1-yl)-3,6,9,12-tetraoxatetradecanamide (#) JV155-1

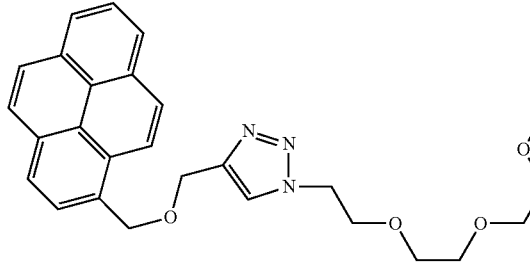

The title compound was prepared according to the general procedure starting from pyrene-triazole-PEG acid (0.12 mmol) using (i-Pr)$_2$EtN as the base. The reaction time was 2 h. The reaction mixture was washed with buffer, aqueous NaHCO$_3$ and brine, concentrated on Celite, and the product was isolated by automated flash chromatography (12 g SiO$_2$ column, gradient elution from DCM to MeOH) as a yellowish oil.

Yield: 32 mg (31%); Rt=0.44 (DCM:MeOH 9:1);

$^1$H NMR (500.13 MHz, CDCl$_3$): δ 1.49 (s, 6H, C(2)H$_3$), 2.76 and 2.78 (m, 2H, C(13)H$_2$), 2.76 and 2.89 (s, 3H, C(15)H$_3$), 3.38 and 3.50 (m, 2H, C(14)H$_2$), 3.48-3.55 (m, 12H, 6×CH$_2$), 3.82 (s, 2H, CH$_2$), 3.88 and 4.06 (s, 2H, C(17)H$_2$), 4.51 (m, 2H, CH$_2$), 4.81 (m, 2H, OCH$_2$-triazole), 5.31 (m, 2H, OCH$_2$-pyrene), 7.10 (m, 2H, C(10)H), 7.10 and 7.18 (m, 2H, C(11)H), 7.38 (m, 2H, C(4)H and C(6)H), 7.49 (m, 1H, C(5)H), 7.72 (m, 1H, C(7)H), 7.74 (m, 1H, C$_{triazole}$H), 7.98-8.05 (m, 4H, C$_{Ar}$H), 8.13 (m, 2H, C$_{Ar}$H), 8.18 (m, 2H, C$_{Ar}$H), 8.34 (m, 1H, C$_{Ar}$H);

$^{19}$F NMR (470.55 MHz, CDCl$_3$): δ −97.6 and −97.5 (bs, 2F, CF$_2$), −84.8 and −84.8 (bt, 2F, CF$_2$);

$^{13}$C {$^1$H} NMR (125.77 MHz, CDCl$_3$): δ 30.8 (bs, C(2)H$_3$), 32.8 and 34.0 (s, C(13)H$_2$), 33.4 and 34.8 (s, C(15)H$_3$), 49.7 and 50.6 (s, C(14)H$_2$), 50.2 (s, CH$_2$), 63.7 (s, OCH$_2$-triazole), 69.4 and 69.4 (s, CH$_2$), 70.1 and 70.2 (s, C(17)H$_2$), 70.3-70.5 (s, 6×CH$_2$), 70.9 (s, OCH$_2$-pyrene), 76.3 (bs, C(1)), 110.6 (m, C(8)), 111.3 (m, CF$_2$), 117.2 (m, CF$_2$), 121.6 and 121.8 (s, C(10)H), 123.4 (s, C$_{Ar}$H), 123.9 (s, C$_{triazole}$H), 124.5 (s, C$_{Ar}$H), 124.7 (s, C$_{Ar}$), 124.9 (s, C$_{Ar}$), 125.2 (s, 2×C$_{Ar}$H), 125.9 (s, C$_{Ar}$H), 127.2 (s, C$_{Ar}$H), 127.4 (s, 2×C$_{Ar}$H), 127.5 (bs, C(4)H or C(6)H), 127.7 (s, C$_{Ar}$H), 128.9 (bm, C(7)), 129.4 (s, C$_{Ar}$), 129.5 (bm, C(4)H or C(6)H), 130.0 (s, C(11)H), 130.5 (s, C(5)H), 130.8 (s, C$_{Ar}$), 131.1 (s, C$_{Ar}$), 131.2 (s, C$_{Ar}$), 131.3 (s, C$_{Ar}$), 136.9 and 137.6 (s, C(12)), 145.0 (s, C$_{triazole}$), 147.2 and 147.4 (m, C(9)), 149.7 (s, C(3)), 168.9 and 169.0 (s, C(16));

HRMS (m/z, ESI/MALDI): [M+Na]$^+$ calcd. for C$_{50}$H$_{53}$F$_4$IN$_4$NaO$_8$, 1063.2736, found, 1063.2738.

N-(4-(2-(3,3-Dimethyl-1λ³-benzo[d][1,2]iodaoxol-1 (3H)-yl)-1,1,2,2-tetrafluoroethoxy)phenethyl)-N-methyl-4-nitrobenzenesulfonamide (#) JV1 50-1

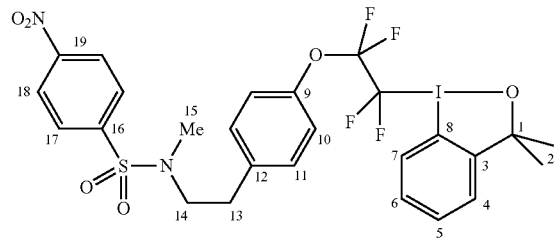 [SMILES: CN(CCc1ccc(OC(F)(F)C(F)(F)I2OC(C)(C)c3ccccc32)cc1)S(=O)(=O)c1ccc([N+](=O)[O-])cc1]

The NMT reagent (74 mg, 0.1 mmol, 1.0 equiv.) was dissolved in anhydrous DCM (1 mL) in an oven-dried Schlenk flask at −25° C., and Et$_3$N (140 µL, 1 mmol, 10 equiv.) was added. A solution of 4-nitrobenzenesulfonyl chloride (24 mg, 0.11 mmol, 1.08 equiv.) in DCM (2 mL) was added dropwise, and the yellow solution was stirred at −25° C. to rt for 30 min. The reaction mixture was directly concentrated onto Celite and the product was isolated by automated flash chromatography (12 g SiO$_2$ column, gradient elution from hexane to EtOAc) as a colourless oil.

Yield: 59 mg (85%); R$_f$=0.22 (EtOAc:hexane 1:1);

$^1$H NMR (400.13 MHz, CDCl$_3$): δ 1.49 (s, 6H, C(2)H$_3$), 2.80 (s, 3H, C(15)H$_3$), 2.90 (t, $^3J_{HH}$=7.6, 2H, C(13)H$_2$), 3.31 (t, $^3J_{HH}$=7.6, 2H, C(14)H$_2$), 7.13 (d, $^3J_{HH}$=8.3, 2H, C(10)H), 7.20 (d, $^3J_{HH}$=8.3, 2H, C(11)H), 7.39 (m, 2H, C(4)H and C(6)H), 7.50 (m, 1H, C(5)H), 7.73 (m, 1H, C(7)H), 7.92 (d, $^3J_{HH}$=8.6, 2H, C(17)H), 8.33 (d, $^3J_{HH}$=8.6, 2H, C(18)H);

$^{19}$F NMR (376.46 MHz, CDCl$_3$): δ−97.6 (bs, 2F, CF$_2$), −84.8 (t, $^3J_{FF}$=4.0, 2F, CF$_2$);

$^{13}$C {$^1$H} NMR (100.62 MHz, CDCl$_3$): δ 30.9 (s, C(2)H$_3$), 34.2 (s, C(13)H$_2$), 35.2 (s, C(15)H$_3$), 51.6 (s, C(14)H$_2$), 76.4 (s, C(1)), 111.0 (s, C(8)), 111.4 (tt, $^1J_{CF}$=337, $^2J_{CF}$=38.0, CF$_2$), 117.2 (tt, $^1J_{CF}$=278, $^2J_{CF}$=26.0, CF$_2$), 121.8 (s, C(10)H), 124.3 (s, C(18)H), 127.4 (s, C(4)H or C(6)H), 128.3 (s, C(17)H), 129.0 (t, J$_{CF}$=5.1, C(7)H), 129.4 (s, C(4)H or C(6)H), 130.0 (s, C(11)H), 130.3 (s, 1H, C(5)H), 136.6 (s, C(12)), 143.8 (s, C(16)), 147.6 (t, $^3J_{CF}$=1.6, C(9)), 149.8 (s, C(3)), 150.0 (s, C(19));

HRMS (m/z, ESI$^+$): [M+H]$^+$ calcd. for C$_{26}$H$_{26}$F$_4$IN$_2$O$_6$S, 697.0487, found, 697.0478.

1-(2-(4-(2-((5-(Dimethylammonio)-N-methylnaphthalene)-1-sulfonamido)ethyl)phenoxy)-1,1,2,2-tetrafluoroethyl)-3,3-dimethyl-2,3-dihydro-1H-1λ³-benzo[d][1,2]iodaoxol-2-ium chloride (#) IK2-46

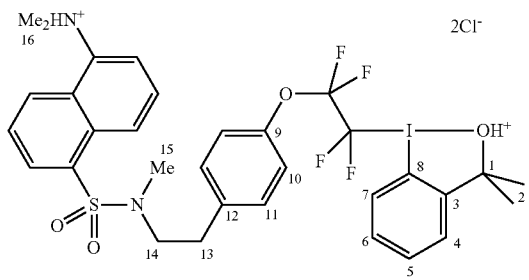

The NMT reagent (74 mg, 0.1 mmol, 1.0 equiv.) was dissolved in anhydrous DCM (1 mL) in an oven-dried Schlenk flask at −25° C., and Et₃N (140 μL, 1 mmol, 10 equiv.) was added. A solution of dansyl chloride (29 mg, 0.11 mmol, 1.08 equiv.) in DCM (2 mL) was added dropwise, and the yellow solution was stirred at −25° C. to −5° C. for 2 h. The reaction mixture was directly concentrated on silica gel (evaporation at 20° C.) and the product was isolated by automated flash chromatography (12 g SiO₂ column, gradient elution from cyclohexane to EtOAc) as a yellowish oil (70 mg). The oil was dissolved in diethyl ether (5 mL) at −5° C. and a 4M solution of HCl in dioxane (0.1 mL) was added, yielding a pale yellow solid.

Yield: 74 mg (90%); m.p. 85° C. (dec.); $R_f$=0.80 (EtOAc);

¹H NMR (400.13 MHz, CDCl₃): δ 1.74 (s, 6H, C(2)H₃), 2.87 (s, 3H, C(15)H₃), 2.90 (m, 2H, C(13)H₂), 3.40 (s, 6H, C(16)H₃), 3.49 (m, 2H, C(14)H₂), 7.07 (m, 2H, C(10)H), 7.13 (m, 2H, C(11)H), 7.31 (m, 1H, C(6)H), 7.61-7.68 (m, 3H, C(4)H, C(5)H, and $C_{Ar}$H), 7.83 (bm, 2H, $C_{Ar}$H), 8.17 (m, 1H, C(7)H), 8.26 (m, 1H, $C_{Ar}$H), 8.63 (m, 1H, $C_{Ar}$H), 9.31 (bm, 1H, $C_{Ar}$H);

¹⁹F NMR (376.46 MHz, CDCl₃): δ −84.5 (bt, $^3J_{FF}$=7.1, 2F, CF₂), −84.4 (bt, $^3J_{FF}$=7.1, 2F, CF₂);

¹³C {¹H} NMR (100.84 MHz, CDCl₃):[3] δ 31.6 (s, C(2)H₃), 33.4 (s, C(13)H₂), 34.2 (s, C(15)H₃), 47.3 (s, C(16)H₃), 50.6 (s, C(14)H₂), 74.2 (s, C(1)), 111.0 (tt, $^1J_{CF}$=341, $^2J_{CF}$=41.0, CF₂), 112.9 (s, C(8)), 115.9 (tt, $^1J_{CF}$=278, $^2J_{CF}$=26.0, CF₂), 121.5 (s, C(10)H), 126.2 (s, $C_{Ar}$), 126.7 (s, $C_{Ar}$H), 127.1 (s, $C_{Ar}$H), 127.4 (s, $C_{Ar}$H), 128.0 (s, $C_{Ar}$H), 129.5 (s, C(4)H), 129.7 (s, $C_{Ar}$), 130.0 (s, C(11)H), 130.2 (s, 1H, C(6)H), 130.8 (s, $C_{Ar}$H), 132.8 (s, 1H, C(5)H), 134.8 (s, $C_{Ar}$), 137.2 (s, C(12)), 138.5 (m, C(7)H), 139.2 (s, $C_{Ar}$), 146.5 (s, C(9)), 147.2 (s, C(3));

HRMS (m/z, ESI⁺): [M−HCl₂]+calcd. for C₃₂H₃₄F₄IN₂O₄S, 745.1215, found, 745.1216.

[3] One $C_{Ar}$H signal of the naphthyl moiety was not observed, presumably due to an overlap.

2-(6-(Diethylamino)-3-(diethyliminio)-3H-xanthen-9-yl)-5-(N-(4-(2-(3,3-dimethyl-1λ³-benzo[d][1,2]iodaoxol-1 (3H)-yl)-1,1,2,2-tetrafluoroethoxy)phenethyl)-N-methylsulfamoyl)benzenesulfonate (#) JV174-6

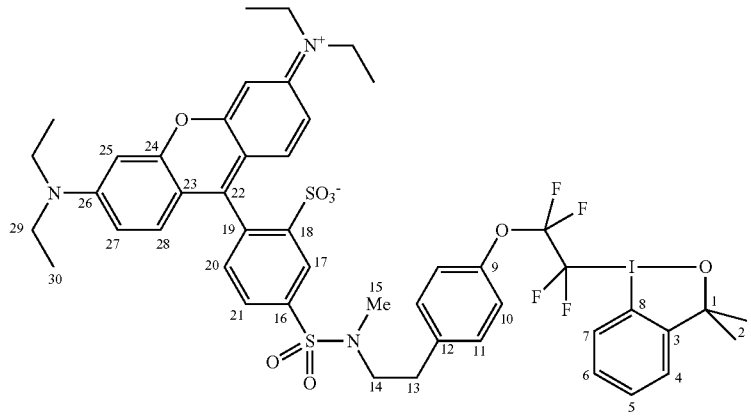

Lissamine™ Rhodamine B sulfonyl chloride (29 mg, 0.05 mmol, 1 equiv.) was dissolved in anhydrous DCM (20 mL) in an oven-dried Schlenk flask at 0° C., and Et₃N (70 μL, 0.5 mmol, 10 equiv.) was added. The NMT reagent (37 mg, 0.05 mmol, 1.0 equiv.) was added as solid, and the intense red-purple solution was stirred at 0° C. to rt for 2 h. The reaction mixture was washed with brine (50 mL), dried over Na₂SO₄, and concentrated onto Celite. The product was isolated by automated flash chromatography (24 g SiO₂ column, gradient elution from DCM to DCM:MeOH 4:1) deep purple solid.

Yield: 23 mg (46%); $R_f$=0.50 (DCM:MeOH 9:1);

¹H NMR (500.13 MHz, CD₃OD): δ1.29 (t, $^3J_{HH}$=7.2, 12H, C(30)H₃), 1.49 (s, 6H, C(2)H₃), 2.90 (s, 3H, C(15)H₃), 2.96 (m, 2H, C(13)H₂), 3.44 (m, 2H, C(14)H₂), 3.66 (q, $^3J_{HH}$=7.2, 8H, C(29)H₂), 6.93 (d, $^4J_{HH}$=2.5, 2H, C(25)H), 6.98 (dd, $^3J_{HH}$=9.5, $^4J_{HH}$=2.5, 2H, C(27)H), 7.09 (d, $^3J_{HH}$=9.5, 2H, C(28)H), 7.22 (d, $^3J_{HH}$=8.4, 1H, C(10)H), 7.38 (dm, $^3J_{HH}$=8.4, 2H, C(11)H), 7.50 (m, 2H, C(6)H), 7.51 (d, $^3J_{HH}$=8.0, 2H, C(20)H), 7.55 (m, 1H, C(4)H), 7.60 (m, 1H, C(5)H), 7.79 (m, 1H, C(7)H), 8.01 (dd, $^3J_{HH}$=8.0, $^4J_{HH}$=1.9, 1H, C(21)H), 8.58 (d, $^4J_{HH}$=1.9, 1H, C(17)H);

¹⁹F NMR (470.55 MHz, CD₃OD): δ −96.9 (bs, 2F, CF₂), −85.4 and −85.3 (bt, 2F, CF₂);

¹³C {¹H} NMR (150.93 MHz, CD₃OD): δ12.8 (s, C(30) H₃), 31.0 (s, C(2)H₃), 34.9 (s, C(13)H₂), 35.6 (s, C(15)H₃), 46.8 (s, C(29)H$_2$), 52.8 (s, C(14)H$_2$), 77.4 (s, C(1)), 97.0 (s, C(25)H), 111.1 (bm, C(8)), 112.3 (tt, $^1J_{CF}$=335, $^2J_{CF}$=39.0, CF$_2$), 115.1 (s, C(27)H), 115.2 (s, C(23)), 118.4 (tt, $^1J_{CF}$=276, $^2J_{CF}$=26.0, CF$_2$), 122.8 (s, C(10)H), 129.2 (s, C(4)H), 131.7 (s, C(11)H), 132.2 (s, 1H, C(5)H), 128.0 (s, C(17)H), 129.6 (s, C(21)H), 130.4 (m, C(7)H), 131.1 (bm, C(6)H), 132.7 (s, C(20)H), 133.6 (s, C(28)H), 135.8 (s, C(19)), 139.1 (s, C(12)), 141.2 (s, C(16) or C(18)), 147.3 (s, C(16) or C(18)), 148.7 (m, C(9)), 151.0 (s, C(3)), 157.2 (s, C(26)), 157.6 (s, C(22)), 159.4 (s, C(24));

HRMS (m/z, ESI/MALDI): [M+H]$^+$ calcd. for C$_{47}$H$_{51}$F$_4$IN$_3$O$_8$S$_2$, 1052.2093, found, 1052.2095.

1-(2-(4-(2-((2-((3',6'-Dihydroxy-3-oxo-3H-spiro [isobenzofuran-1,9'-xanthen]-6-yl)amino)-2-oxo-ethyl)(methyl)ammonio)ethyl)phenoxy)-1,1,2,2-tetrafluoroethyl)-3,3-dimethyl-2,3-dihydro-1H-1λ$^3$-benzo[d][1,2]iodaoxol-2-ium bis(trifluoroacetate) (#) AK10-15 and JV179-2

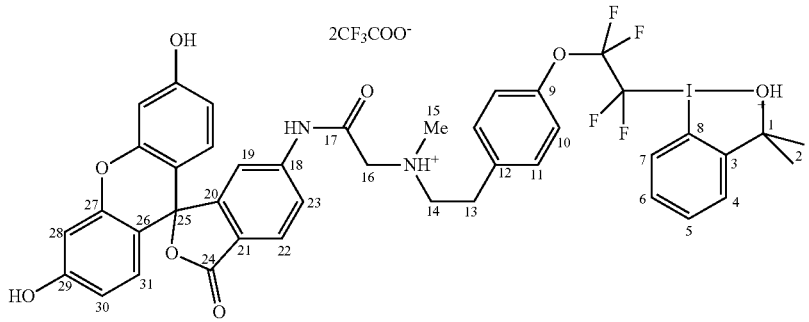 [SMILES: C[NH+](CCc1ccc(OC(F)(F)C(F)(F)I2OC(C)(C)c3ccccc32)cc1)CC(=O)Nc1ccc2c(c1)C1(OC2=O)c2ccc(O)cc2Oc2cc(O)ccc21]

6-(2-bromoacetamido)fluorescein (24 mg, 0.05 mmol, 0.5 equiv.) was dissolved in anhydrous DMF (350 µL) at 0° C. K$_2$CO$_3$ (69 mg, 0.50 mmol, 5 equiv.) was added, followed by a solution of the NMT reagent (74 mg, 0.1 mmol, 1.0 equiv.) in DMF (400 µL). The intense red reaction mixture was stirred at 0° C. to rt for 2 h. TFA (100 µL) was added and the mixture turned intense yellow. The solution was diluted with chloroform (15 mL), washed with brine brine (1×10 mL), dried over Na$_2$SO$_4$, and concentrated onto Celite. The crude product was isolated by automated flash chromatography (24 g SiO$_2$ column, gradient elution from DCM to DCM:MeOH 3:1) as a yellow solid.

Yield: 22 mg (39%); m.p. 125-130° C. (dec.); R$_f$=0.54 (DCM:MeOH 9:1);

$^1$H NMR (500.13 MHz, CD$_3$OD): δ1.69 (s, 6H, C(2)H$_3$), 3.02 (s, 3H, C(15)H$_3$), 3.12 (t, $^3J_{HH}$=8.3, 2H, C(13)H$_2$), 3.46 (bm, 2H, C(14)H$_2$), 4.20 (s, 2H, C(16)H$_2$), 6.55 (dd, $^3J_{HH}$=8.6, $^4J_{HH}$=2.4, 2H, C(30)H), 6.63 (d, $^3J_{HH}$=8.6, 2H, C(31)H), 6.70 (d, $^4J_{HH}$=2.4, 2H, C(28)H), 7.27 (m, 2H, C(10)H), 7.41 (m, 2H, C(11)H), 7.58 (m, 1H, C(6)H), 7.66 (d, $^4J_{HH}$=1.8, 1H, C(19)H), 7.73 (m, 1H, C(5)H), 7.75 (dd, $^3J_{HH}$=8.5, $^4J_{HH}$=1.8, 1H, C(23)H), 7.77 (m, 1H, C(4)H), 7.98 (d, $^3J_{HH}$=8.5, 1H, C(22)H), 8.00 (m, 1H, C(7)H);

$^{19}$F NMR (470.55 MHz, CDCl$_3$): δ−84.6 (bt, $^3J_{FF}$=5.5, 2F, CF$_2$), −80.8 and −80.7 (bs, 2F, CF$_2$), −77.1 and −77.1 (bm, 6F, CF$_3$);

$^{13}$C {$^1$H} NMR (125.77 MHz, CDCl$_3$):[4] δ 30.2 (s, C(2)H$_3$), 30.8 (s, C(13)H$_2$), 42.4 (s, C(15)H$_3$), 58.7 (s, C(16)H$_2$), 58.9 (s, C(14)H$_2$), 76.7 (s, C(1)), 103.5 (s, C(28)H), 110.3 (s, C(8)), 111.3 (s, C(26)), 113.7 (s, C(30)H), 110.5 (m, CF$_2$), 117.1 (m, CF$_2$), 115.4 (s, C(19)H), 117.8 (q, $^1J_{CF}$=292, CF$_3$COO—), 122.2 (s, C(23)H), 123.1 (s, C(10)H), 123.7 (s, C(21)), 127.1 (s, C(22)H), 130.2 (s, C(31)H), 130.7 (s, C(4)H), 131.8 (s, C(11)H), 132.4 (s, C(6)H), 133.8 (s, 1H, C(5)H), 134.2 (m, C(7)H), 137.3 (s, C(12)), 145.4 (s, C(18)), 148.7 (m, C(9)), 149.6 (s, C(3)), 154.1 (s, C(27) or C(29)), 156.0 (bs, C(20)), 161.5 (s, C(27) or C(29)), 162.3 (q, $^2J_{CF}$=35.5, CF$_3$COO—), 164.7 (s, C(17)), 170.9 (s, C(24));

HRMS (m/z, ESI$^+$): [M+H]$^+$ calcd. for C$_{42}$H$_{36}$F$_4$IN$_2$O$_8$, 899.1447, found, 899.1441.

[4] The signal of C(25) was not observed, presumably due to significant broadening. The chemical shifts of CF$_2$CF$_2$ were determined from a $^{19}$F-$^{13}$C HMBC experiment.

Example 11

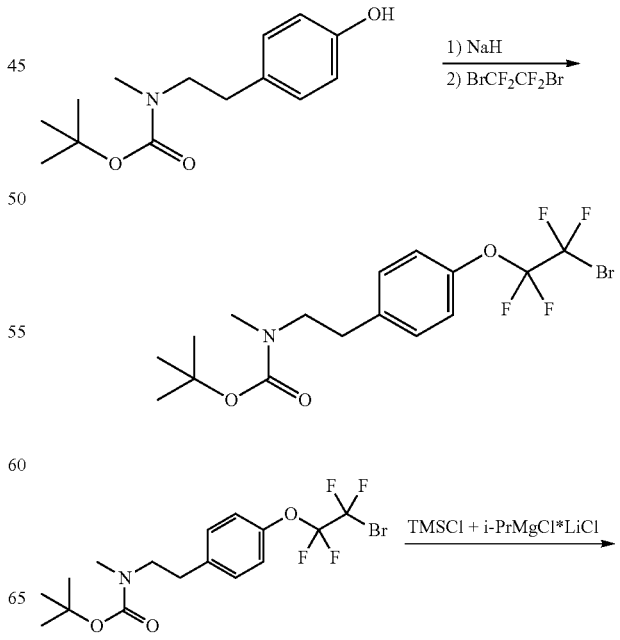

103
-continued
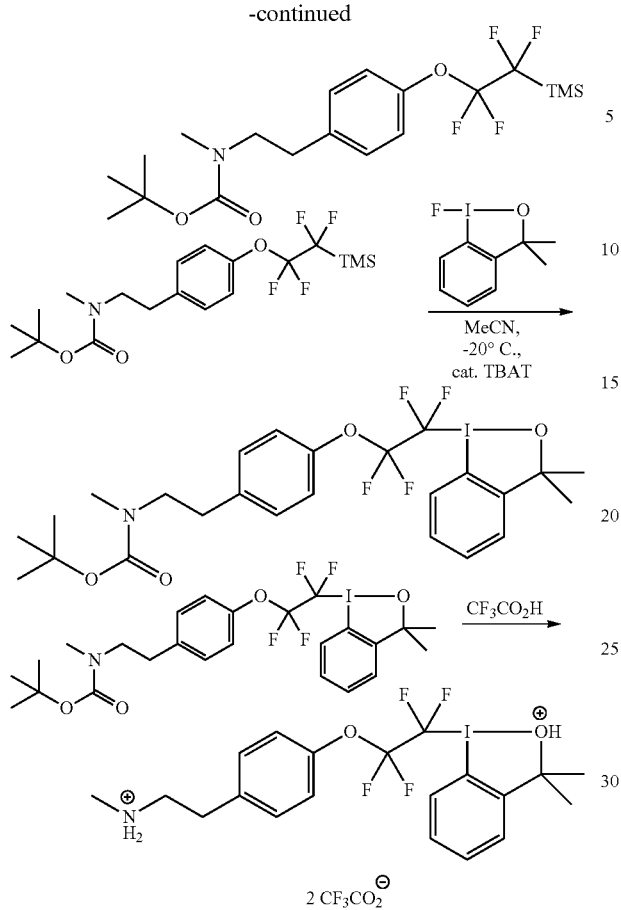
104
-continued
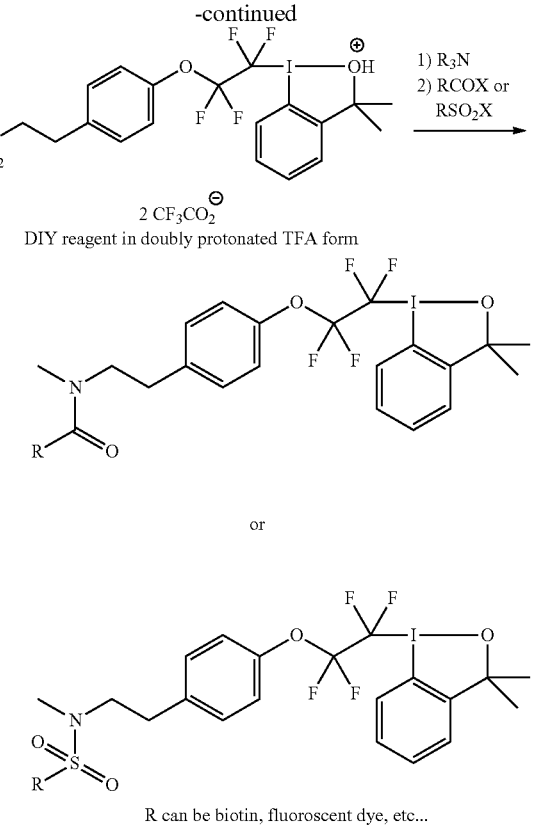
Example 12
| Reaction code | CFDM01_35 | Date | Jun. 19, 2018 |
|---|---|---|---|
| | Reaction scheme | | |
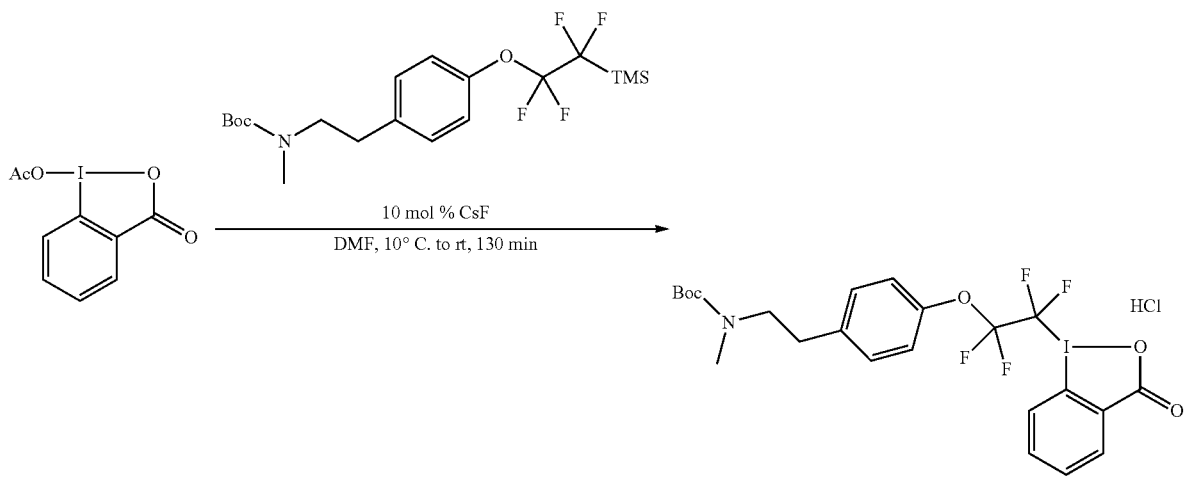
| Compound | w/% | c/mol L$^{-1}$ | M/g mol$^{-1}$ | eq | n/mmol | ρ/g mL$^{-1}$ | m/g | V/mL |
|---|---|---|---|---|---|---|---|---|
| AcO—I—O (structure) | — | — | 306.055 | 2.00 | 23.62 | — | 7.23 | |

| | | | | | | | |
|---|---|---|---|---|---|---|---|
| CsF | — | — | 151.904 | 0.100 | 1.181 | — | 0.179 |
| 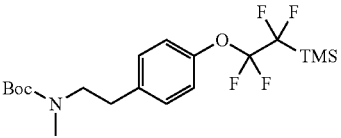 [SMILES: CN(CCc1ccc(OC(F)(F)C(F)(F)[Si](C)(C)C)cc1)C(=O)OC(C)(C)C] | — | — | 423.524 | 1.02 | 12.05 | — | 5.10 |
| 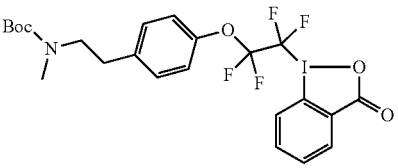 [SMILES: CN(CCc1ccc(OC(F)(F)C(F)(F)I2OC(=O)c3ccccc32)cc1)C(=O)OC(C)(C)C] | — | — | 597.345 | 1.00 | 11.81 | — | 7.06 |
| 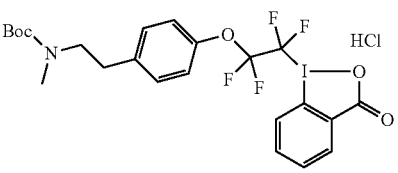 [SMILES: CN(CCc1ccc(OC(F)(F)C(F)(F)I2OC(=O)c3ccccc32)cc1)C(=O)OC(C)(C)C ; Cl] | — | — | 633.803 | 1.00 | 11.81 | — | 7.49 |
| | | | | | Yield: | 2.20 | 29.4% |

Literature Procedure: Matúš Chvojka-BP

Caesium fluoride (0.1 eq) was dried with a heat gun under vacuum and suspended together with acetoxyidodane (2.0 eq) in dry DMF (15 mL). The resulting mixture was cooled to 10° C. and solution of silane CFMA01_02 (1.0 eq) in dry DMF (10 mL) was gradually added over the course of 35 minutes. The resulting mixture was left to react while reaching the room temperature (95 min). Then it was diluted with water (600 mL) and stirred for 10 min. DCM (350 mL) was added, then biphasic mixture was thoroughly mixed and filtered. The organic phase was separated and the aqueous phase was extracted with additional DCM (200 mL). Combined organic phases were washed with dist. water (500 mL). The organic phase was dried over $Na_2SO_4$ and concentrated to near dryness. The residue was dissolved in EtOAc and extracted with dist water (250 mL). Organic layer was dried under anhydrous $Na_2SO_4$ and solvent evaporated. Yield yellow oil (~6 g). This was dissolved in dry $Et_2O$ (50 mL) and HCl in $Et_2O$ (3M, excess) was added to precipitate the HCl salt, which was filtered and washed with additional $Et_2O$.

| Chemical analysis | NMR | | HRMS | GC/HPLC | Melting point | Other |
|---|---|---|---|---|---|---|
| | $^1H$ | $^{13}C$ | | | | |
| | /1/19 | | | | | |

Example 13

| Reaction code | CFDM01_40 Date Jun. 25, 2018 |
|---|---|
| | Reaction scheme |

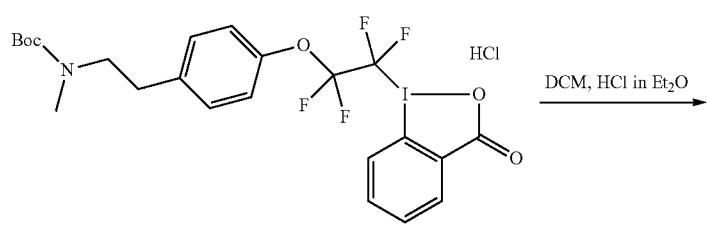 [SMILES: CN(CCc1ccc(OC(F)(F)C(F)(F)I2OC(=O)c3ccccc32)cc1)C(=O)OC(C)(C)C ; Cl]

-continued

| Compound | w/% | c/mol L$^{-1}$ | M/g mol$^{-1}$ | eq | n/ mmol | ρ/g mL$^{-1}$ | m/g | V/mL |
|---|---|---|---|---|---|---|---|---|
| Boc-protected compound | — | — | 633.803 | 1.00 | 9.309 | — | 5.90 | |
| HCl in Et2O | — | 3.00 | | 4.00 | 37.24 | — | | 12.4 |
| HCl product | — | — | 570.144 | 1.00 | 9.309 | — | 5.31 | |
| | | | | | Yield: | | 3.20 | 60.3% |

Literature Procedure: Matúš Chvojka-BP

HCl salt (5.90 g, 9.31 mmol) was dissolved in dichloromethane (25 mL) and MeOH (10 mL). HCl in diethyl ether (3.0 M, 12 mL, 37.2 mmol) was added. The reaction mixture was stirred overnight at rt. Reaction mixture was checked by TLC. Volume of the solution was reduced by evaporation to half of its original volume. Solution was seeded with crystals of title compound and Et$_2$O was added to start the precipitation. Suspension was stirred for several hours in ice bath to complete the precipitation. Suspension was filtered and solid washed with Et20 (2 × 20 mL). CFDM01_40_1 (3.2 g, off white fine powder). Addition of Et2O to filtrate led to separation of another layer with the rest of the product which did not want to crystallize as in the previous batch and was therefore discarded.

| Chemical analysis | NMR | | HRMS | GC/HPLC | Melting point | Other |
|---|---|---|---|---|---|---|
| | $^1$H | $^{13}$C | | | | |
| | /1/19 | | | | | |

Example 14

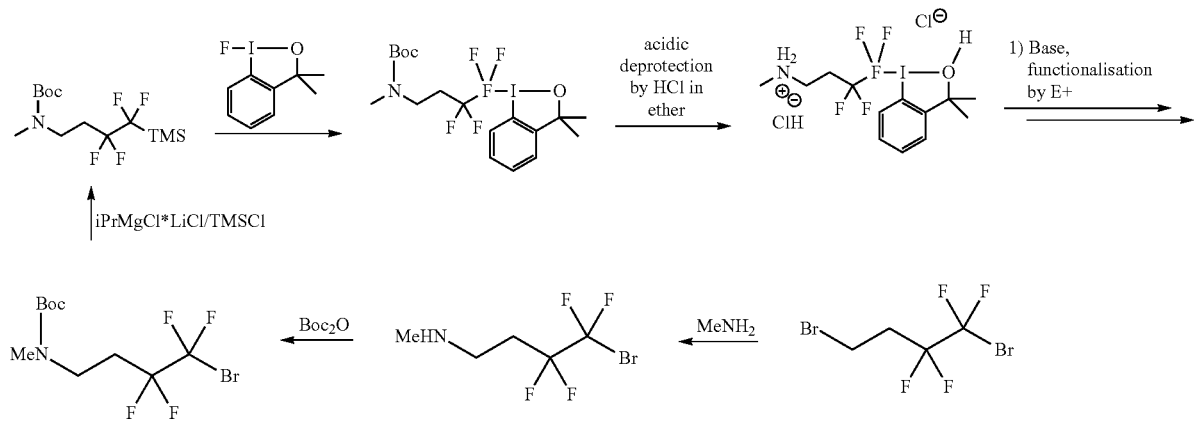

Example 15

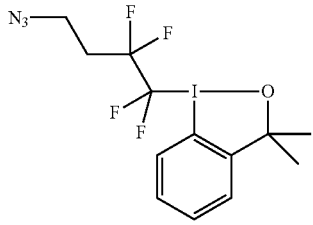 [SMILES: CC1(C)OI(C(F)(F)C(F)(F)CCN=[N+]=[N-])c2ccccc21]

This compound was synthesized based on the corresponding reaction sequence and tested in protein.

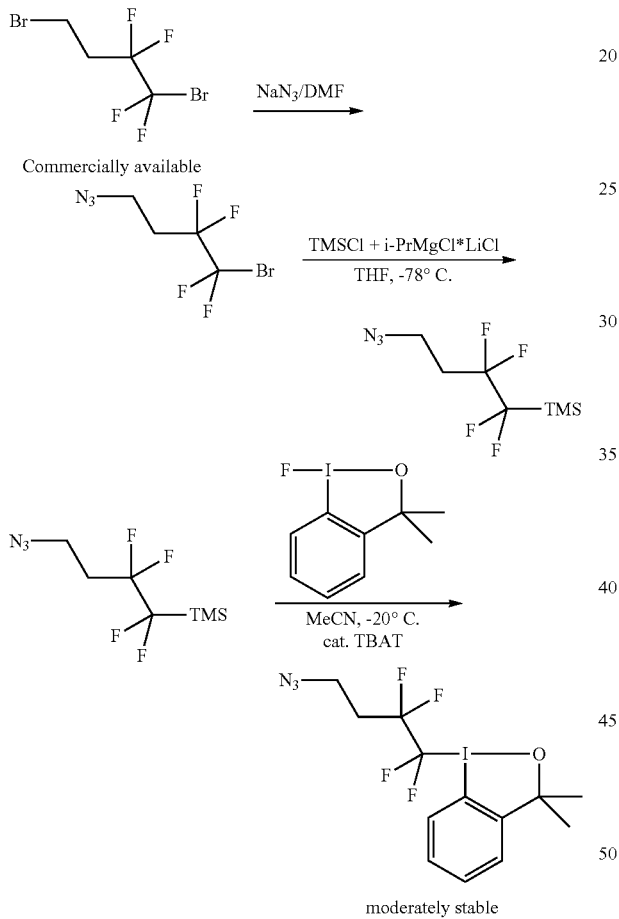

moderately stable

We claim:
1. A compound of formula (I) or formula (II), or a salt thereof,

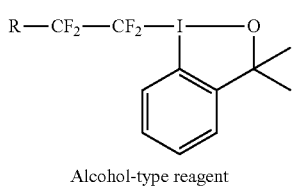

Alcohol-type reagent

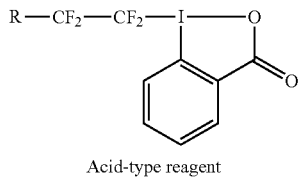

Acid-type reagent wherein
R is a nucleophile of formula III, -$L^1_a$-$R^1$-$L^2_c$-$R^2_d$-$L^3_e$-E (III), wherein
a is 0 or 1 and $L^1$ is selected from —O—, —S— or —$C_1$-alkyl,
$R^1$ is selected from imidazole, pyrazole, benzimidazole, phenyl and pyridine,
c is 0 or 1 and $L^2$ is a $C_{1-4}$-alkyl,
d is 0 or 1 and $R^2$ is selected from —C(=O)—O—, —O—(C=O)—, —N($R^5$)—, —N($R^5$)—C(=O)—, —C(=O)—N($R^5$)— and —N($R^5$)—$SO_2$—,
with $R^5$ being selected from —H, —$C_{1-4}$-alkyl, —$C_{2-4}$-alkene, —$C_{2-4}$-alkynyl, —$SO_2$F, —CHO, —C(=O)—O-tertbutyl (Boc), —C≡C—Si($CH_3$)$_3$, 3-Oxo-4,7,7-trimethyl-2-oxabicyclo[2.2.1]heptane-1-carbonyl (camphanic carbonyl), an affinity tag selected from the group consisting of a biotin tag and a Myc tag, or a fluorescent dye,
e is 0 or 1 and $L^3$ is selected from —$C_{1-8}$-alkyl-, -phenyl-, —[($CH_2$)$_{1-4}$—O—]$_{1-5}$—, —[($CH_2$)$_{1-4}$—O—]$_{1-4}$—($CH_2$)$_{1-4}$—, and —[($CH_2$)$_{1-4}$—O—]$_{1-4}$-triazole-[($CH_2$)$_{1-4}$—O—]$_{1-2}$—($CH_2$)$_{1-2}$—, and
E is selected from —H, —$C_{1-4}$-alkyl, —$C_{2-4}$-alkenyl, —$C_{2-4}$-alkynyl, —$NO_2$, halogen, —$NH_2$, —OH, —$C_{1-3}$—$N_3$, —$N_3$, —CN, —$SO_2$F, —CHO, —C(=O)—O-tertbutyl (Boc), —Si($CH_3$)$_3$(TMS), —Si($CH_2$—$CH_3$)$_3$, —O—Si($CH_3$)$_3$, —O—Si($CH_2CH_3$)$_3$, —C≡C—Si($CH_3$)$_3$, 3-Oxo-4,7,7-trimethyl-2-oxabicyclo[2.2.1]heptane-1-carbonyl (camphanic carbonyl), pinalcolyl boronate, dioxolanyl, a bioorthogonal group, an affinity tag selected from the groups consisting of a biotin tag and a Myc tag, or a fluorescent dye, or
R is a nucleophile of formula IV, -$L^4_f$-$R^6_g$-G (IV), wherein
f is 0 or 1 and $L^4$ is selected from $C_{1-2}$-alkyl,
g is 0 or 1 and $R^6$ is selected from —N($R^8$)—, —C(=O)—N($R^8$)—, —N($R^8$)—C(=O)—,
with $R^8$ being selected from —H, —$C_{1-4}$-alkyl, —$C_{2-4}$-alkene, —$C_{2-4}$-alkynyl, —$C_{1-3}$—$N_3$, —C(=O)—O-tertbutyl (Boc), an affinity tag selected from the group consisting of a biotin tag and a Myc tag, or a fluorescent dye,
in case of f is 0 and g is 0, G is selected from —$C_{1-4}$-alkyl, —$C_{2-4}$-alkene, —$C_{2-4}$-alkynyl, —$C_{1-3}$—$N_3$, —$N_3$, —C(=O)—O-tertbutyl (Boc), a bioorthogonal group, an affinity tag selected from the group consisting of a biotin tag and a Myc tag, or a fluorescent dye, in all other cases, G is selected from —H, —$C_{1-4}$-alkyl, —$C_{2-4}$-alkene, —$C_{2-4}$-alkynyl, —$C_{1-3}$—$N_3$, —$N_3$, —C(=O)—O-tertbutyl (Boc), a bioorthogonal group, an affinity tag selected from the group consisting of a biotin tag and a Myc tag, or a fluorescent dye.
2. The compound according to claim 1, wherein
R is a nucleophile of formula III, -$L^1_a$-$R^1$-$L^2_c$-$R^2_d$-$L^3_e$-E (III), wherein a is 0 or 1 and $L^1$ is selected from —O—, or —$C_1$-alkyl, $R^1$ is phenyl, c is 0 or 1 and $L^2$ is a $C_{1-4}$-alkyl, d is 0 or 1 and $R^2$ is selected from —C(=O)—O—, —N($R^5$)—, —N($R^5$)—C(=O)—, and —N($R^5$)—$SO_2$—, with $R^5$ being selected from —H, —$C_{1-4}$-alkyl, C(=O)—O-tertbutyl (Boc), e is 0 or 1 and $L^3$ is selected from —$C_{1-6}$-alkyl-, -phenyl-, —[($CH_2$)$_{1-4}$—O—]$_{1-5}$—, —[($CH_2$)$_{1-2}$—O—]$_{1-4}$—($CH_2$)$_{1-2}$—, and —[($CH_2$)$_{1-2}$—O—]$_{1-4}$-triazole-[($CH_2$)$_{1-2}$—O—]$_1$—($CH_2$)—, and E is selected from —H, —$C_{1-4}$-alkyl, —$C_{2-4}$-alkynyl, —$NO_2$, halogen, —$C_{1-3}$—$N_3$, —$N_3$, —CN, —$SO_2F$, —CHO, —C(=O)—O-tertbutyl (Boc), —C≡C—Si($CH_3$)$_3$, 3-Oxo-4,7,7-trimethyl-2-oxabicyclo[2.2.1]heptane-1-carbonyl (camphanic carbonyl), an affinity tag selected from the group consisting of a biotin tag and a Myc tag, or a fluorescent dye, or R is a nucleophile of formula IV, -$L^4_f$-$R^6_g$-G (IV), wherein f is 0 or 1 and $L^4$ is selected from $C_{1-2}$-alkyl, g is 0 or 1 and $R^6$ is selected from —N($R^8$)—, —C(=O)—N($R^8$)—, with $R^8$ being selected from —H, —$C_{1-4}$-alkyl, —$C_{2-4}$-alkenyl, —C(=O)—O-tertbutyl (Boc), G is selected from —H, —$C_{1-4}$-alkyl, —$C_{2-4}$-alkenyl, —$N_3$, —C(=O)—O-tertbutyl (Boc).

3. The compound according to claim 1, wherein the bioorthogonal group is azide, pikolyl azide or fluoralkyl azide.

4. The compound according to claim 1, wherein the fluorescent dye is selected from coumarin type dyes, rhodamine type dyes, pyrene and fluoresceine.

5. The compound according to claim 1, wherein the fluorescent dye is selected from

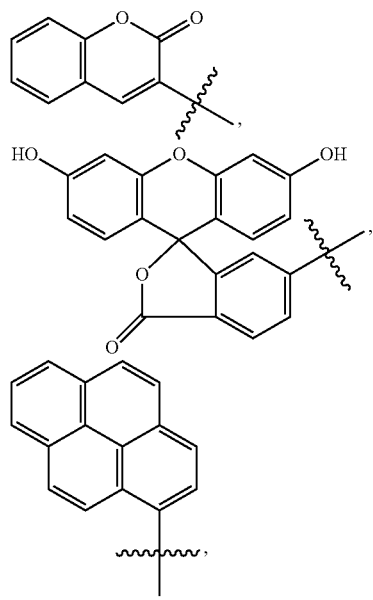

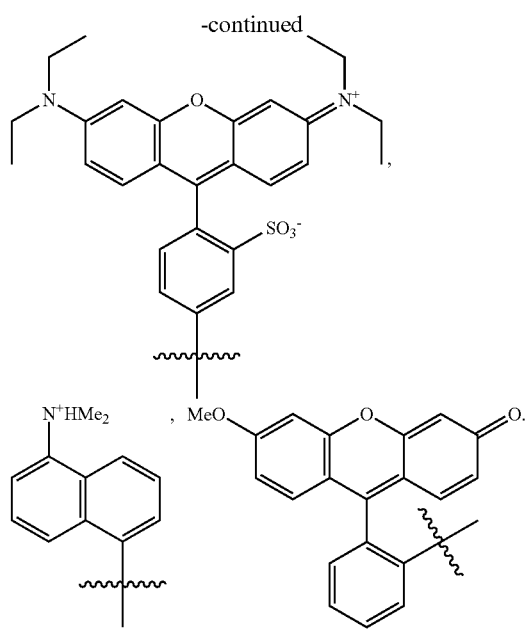

6. The compound according to claim 1, wherein $L^1$ is selected from —O— or $C_1$-alkyl.

7. The compound according to claim 1, wherein $R^1$ is phenyl.

8. The compound according to claim 1, wherein $L^2$ is $C_{1-4}$-alkyl.

9. The compound according to claim 1, wherein $R^2$ is selected from —C(=O)—O—, —N($R^5$)—, —N($R^5$)—C(=O)— with $R^5$ being $C_{1-4}$-alkyl.

10. The compound according to claim 1, wherein $L^3$ is —$C_{1-6}$-alkyl-.

11. The compound according to claim 1, wherein E is selected from —H, —$C_{1-2}$-alkyl, —$N_3$, —C(=O)—O-tertbutyl (Boc).

12. The compound according to claim 1, wherein

R in formula I is a nucleophile of formula III, -$L^1_a$-$R^1$-$L^2_c$-$R^2_d$-$L^3_e$-E (III), wherein a is 0 or 1 and $L^1$ is selected from —O—, or —$C_1$-alkyl, $R^1$ is selected from phenyl, and phenyl-dioxolane, c is 1 and $L^2$ is a $C_{1-4}$-alkyl, d is 1 and $R^2$ is selected from —C(=O)—O—, —N($R^5$)—, —N($R^5$)—C(=O)—, and —N($R^5$)—$SO_2$—, with $R^5$ being selected from —H, —$C_{1-4}$-alkyl, C(=O)—O-tertbutyl (Boc), e is 0 or 1 and $L^3$ is propyl, and E is selected from —H, —$C_{1-4}$-alkyl, —$C_{2-4}$-alkynyl, —$NO_2$, halogen, —$C_{1-3}$—$N_3$, —$N_3$, —CN, —$SO_2F$, —CHO, —C(=O)—O-tertbutyl (Boc), —C≡C—Si($CH_3$)$_3$, 3-Oxo-4,7,7-trimethyl-2-oxabicyclo[2.2.1]heptane-1-carbonyl (camphanic carbonyl), an affinity tag selected from the group consisting of a biotin tag and a Myc tag, or a fluorescent dye, or a is 0 or 1 and $L^1$ is selected from —O—, or —$C_1$-alkyl, $R^1$ is selected from phenyl, and phenyl-dioxolane, c is 1 and $L^2$ is a $C_{1-4}$-alkyl, d is 1 and $R^2$ is selected from —C(=O)—O—, —N($R^5$)—, —N($R^5$)—C(=O)—, and —N($R^5$)—$SO_2$—, with $R^5$ being selected from —H, —$C_{1-4}$-alkyl, C(=O)—O-tertbutyl (Boc), e is 0 or 1 and $L^3$ is selected from —$C_{1-6}$-alkyl-, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, and E is —N$_3$.

13. The compound according to claim 1, wherein R in formula I or II, is of formula III, wherein a is 0 and $L^1$ is selected from —O—, or —$C_1$-alkyl, $R^1$ is selected from phenyl, and phenyl-dioxolane, c is 0 or 1 and $L^2$ is a $C_{1-4}$-alkyl, d is 0 or 1 and $R^2$ is selected from —C(=O)—O—, —N($R^5$)—, —N($R^5$)—C(=O)—, and —N($R^5$)—SO$_2$—, with $R^5$ being selected from —H, —$C_{1-4}$-alkyl, C(=O)—O-tertbutyl (Boc), e is 0 or 1 and $L^3$ is selected from —$C_{1-6}$-alkyl-, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, and E is selected from —H, —$C_{1-4}$-alkyl, —$C_{2-4}$-alkynyl, —NO$_2$, halogen, —$C_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag selected from the group consisting of a biotin tag and a Myc tag, or a fluorescent dye.

14. The compound according to claim 1, wherein R in formula II is of formula III, wherein R is a nucleophile of formula III, -$L^1_a$-$R^1$-$L^2_c$-$R^2_d$-$L^3_e$-E (III), wherein a is 0 or 1 and $L^1$ is selected from —O—, or —$C_1$-alkyl, $R^1$ is selected from phenyl, and phenyl-dioxolane, c is 1 and $L^2$ is a $C_{1-4}$-alkyl, d is 0 or 1 and $R^2$ is selected from —C(=O)—O—, —N($R^5$)—, —N($R^5$)—C(=O)—, and —N($R^5$)—SO$_2$—, with $R^5$ being selected from —H, —$C_{1-4}$-alkyl, C(=O)—O-tertbutyl (Boc), e is 0 or 1 and $L^3$ is selected from —$C_{1-6}$-alkyl-, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, and E is selected from —H, —$C_{1-4}$-alkyl, —$C_{2-4}$-alkynyl, —NO$_2$, halogen, —$C_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag selected from the group consisting of a biotin tag and a Myc tag, or a fluorescent dye, or R is a nucleophile of formula III, -$L^1_a$-$R^1$-$L^2_c$-$R^2_d$-$L^3_e$-E (III), wherein a is 0 or 1 and $L^1$ is selected from —O—, or —$C_1$-alkyl, $R^1$ is selected from phenyl, and phenyl-dioxolane, c is 0 or 1 and $L^2$ is a C14-alkyl, d is 0 or 1 and $R^2$ is selected from —C(=O)—O—, —N($R^5$)—, —N($R^5$)—C(=O)—, and —N($R^5$)—SO$_2$—, with $R^5$ being selected from —H, —$C_{1-4}$-alkyl, C(=O)—O-tertbutyl (Boc), e is 0 or 1 and $L^3$ is selected from —$C_{1-6}$-alkyl-, -phenyl-, —[(CH$_2$)$_{1-4}$—O—]$_{1-5}$—, —[(CH$_2$)$_{1-2}$—O—]$_{1-4}$—(CH$_2$)$_{1-2}$—, and —[(CH$_2$)$_{1-2}$—O—]$_{1-4}$-triazole-[(CH$_2$)$_{1-2}$—O—]$_1$—(CH$_2$)—, and E is selected from —$C_{1-4}$-alkyl, —$C_{2-4}$-alkynyl, —NO$_2$, halogen, —$C_{1-3}$—N$_3$, —N$_3$, —CN, —SO$_2$F, —CHO, —C(=O)—O-tertbutyl (Boc), —C≡C—Si(CH$_3$)$_3$, 3-Oxo-4,7,7-trimethyl-2-oxabicyclo[2.2.1]heptane-1-carbonyl (camphanic carbonyl), an affinity tag selected from the group consisting of a biotin tag and a Myc tag, or a fluorescent dye.

15. The compound according to claim 1, wherein R is a nucleophile of formula IV.

16. The compound according to claim 1, wherein R in formula I or II, is a nucleophile of formula IV, -$L^4_f$-$R^6_g$-G (IV), wherein f is 0 or 1, and $L^4$ is $C_{1-2}$-alkyl, g is 0 or 1 and $R^6$ is selected from —N($R^8$)—, —C(=O)—N($R^8$)—, with $R^8$ being selected from —$C_{1-4}$-alkyl, —C(=O)—O-tertbutyl (Boc), G is selected from —H, —$C_{1-4}$-alkyl, $C_2$-alkenyl, —N$_3$, —C(=O)—O-tertbutyl (Boc).

17. The salt according to claim 1, wherein the salt is an acid addition salt between a compound according to formula I or compound according to formula II and a Brønsted-Lowry acid, wherein the proton is bound to the oxygen in ortho position in the benzoiodoxol scaffold of formula I or II.

18. The compound according to claim 1, wherein the salt is an acid addition salt with the addition being selected from HCl or CF$_3$COOH.

* * * * *